(12) United States Patent
June et al.

(10) Patent No.: US 11,795,240 B2
(45) Date of Patent: *Oct. 24, 2023

(54) ENHANCING ACTIVITY OF CAR T CELLS BY CO-INTRODUCING A BISPECIFIC ANTIBODY

(71) Applicant: The Trustees of the University of Pennsylvania, Philadelphia, PA (US)

(72) Inventors: Carl H. June, Merion Station, PA (US); Yangbing Zhao, Lumberton, NJ (US); Xiaojun Liu, Wallingford, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 319 days.

This patent is subject to a terminal disclaimer.

(21) Appl. No.: 16/910,837

(22) Filed: Jun. 24, 2020

(65) Prior Publication Data

US 2021/0040234 A1 Feb. 11, 2021

Related U.S. Application Data

(60) Continuation of application No. 15/690,383, filed on Aug. 30, 2017, now Pat. No. 10,696,749, which is a division of application No. 14/410,427, filed as application No. PCT/US2013/050275 on Jul. 12, 2013, now Pat. No. 9,765,156.

(60) Provisional application No. 61/671,535, filed on Jul. 13, 2012.

(51) Int. Cl.
| | |
|---|---|
| *C07K 16/16* | (2006.01) |
| *C07K 16/28* | (2006.01) |
| *A61K 35/17* | (2015.01) |
| *A61K 47/68* | (2017.01) |
| *C07K 16/46* | (2006.01) |
| *A61K 39/00* | (2006.01) |
| *C12N 5/16* | (2006.01) |
| *C12N 15/62* | (2006.01) |

(52) U.S. Cl.
CPC ............ *C07K 16/468* (2013.01); *A61K 35/17* (2013.01); *A61K 47/6879* (2017.08); *C07K 16/2803* (2013.01); *C07K 16/2809* (2013.01); *A61K 2039/505* (2013.01); *C07K 2317/21* (2013.01); *C07K 2317/24* (2013.01); *C07K 2317/31* (2013.01); *C07K 2317/622* (2013.01); *C07K 2319/00* (2013.01); *C12N 5/16* (2013.01); *C12N 15/62* (2013.01); *C12N 2510/00* (2013.01)

(58) Field of Classification Search
CPC .............. C07K 16/468; C07K 16/2809; C07K 2317/21; C07K 2317/24; C07K 2317/31; C07K 2317/622; C07K 2319/00; A61K 35/17; A61K 47/6879; A61K 2039/505; A61K 2039/5156; C12N 15/62; C12N 2510/00

See application file for complete search history.

(56) References Cited

U.S. PATENT DOCUMENTS

| | | |
|---|---|---|
| 4,444,887 A | 4/1984 | Hoffmann |
| 4,676,980 A | 6/1987 | Segal et al. |
| 4,716,111 A | 12/1987 | Osband et al. |
| 4,816,567 A | 3/1989 | Cabilly et al. |
| 5,199,942 A | 4/1993 | Gillis et al. |
| 5,225,539 A | 7/1993 | Winter |
| 5,229,275 A | 7/1993 | Goroff et al. |
| 5,350,674 A | 9/1994 | Boenisch et al. |
| 5,399,346 A | 3/1995 | Anderson et al. |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,573,905 A | 11/1996 | Lerner et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,731,168 A | 3/1998 | Carter et al. |
| 5,766,886 A | 6/1998 | Studnicka et al. |
| 5,814,318 A | 9/1998 | Lonberg et al. |
| 5,858,358 A | 1/1999 | June et al. |
| 5,883,223 A | 3/1999 | Gray |
| 5,939,598 A | 8/1999 | Kucherlapati et al. |
| 5,993,434 A | 11/1999 | Dev et al. |
| 6,120,766 A | 9/2000 | Hale et al. |

(Continued)

FOREIGN PATENT DOCUMENTS

| | | |
|---|---|---|
| EP | 239400 A2 | 9/1987 |
| EP | 592106 B1 | 11/2004 |

(Continued)

OTHER PUBLICATIONS

Tammana, Human Gene Therapy, 21:75-86 (Year: 2010).*

(Continued)

*Primary Examiner* — Hong Sang
(74) *Attorney, Agent, or Firm* — Saul Ewing LLP; Kathryn Doyle

(57) ABSTRACT

The present invention provides compositions and methods for treating cancer in a human. The invention includes administering a T cell, genetically modified to express a chimeric antigen receptor (CAR), a bispecific antibody, or a combination thereof to a subject. The CAR and bispecific antibody of the invention can comprise a human antibody, a humanized antibody, or antigen-binding fragments thereof.

16 Claims, 13 Drawing Sheets

Specification includes a Sequence Listing.

(56) References Cited

U.S. PATENT DOCUMENTS

| | | |
|---|---|---|
| 6,181,964 B1 | 1/2001 | Hofmann et al. |
| 6,233,482 B1 | 5/2001 | Hofmann et al. |
| 6,241,701 B1 | 6/2001 | Hofmann et al. |
| 6,326,193 B1 | 12/2001 | Liu et al. |
| 6,331,415 B1 | 12/2001 | Cabilly et al. |
| 6,352,694 B1 | 3/2002 | June et al. |
| 6,407,213 B1 | 6/2002 | Carter et al. |
| 6,516,223 B2 | 2/2003 | Hofmann et al. |
| 6,534,055 B1 | 3/2003 | June et al. |
| 6,548,640 B1 | 4/2003 | Winter |
| 6,567,694 B2 | 5/2003 | Hayakawa et al. |
| 6,678,556 B1 | 1/2004 | Nolan et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,171,264 B1 | 1/2007 | Hofmann et al. |
| 7,172,869 B2 | 2/2007 | June et al. |
| 7,173,116 B2 | 2/2007 | Fewell et al. |
| 7,175,843 B2 | 2/2007 | June et al. |
| 7,232,566 B2 | 6/2007 | June et al. |
| 7,262,276 B2 | 8/2007 | Huang et al. |
| 7,575,923 B2 | 8/2009 | Dorken et al. |
| 2004/0014645 A1 | 1/2004 | Draghia-Akli et al. |
| 2004/0059285 A1 | 3/2004 | Mathiesen et al. |
| 2004/0092907 A1 | 5/2004 | Mathiesen et al. |
| 2004/0101519 A1 | 5/2004 | June et al. |
| 2005/0042664 A1 | 2/2005 | Wu et al. |
| 2005/0048617 A1 | 3/2005 | Wu et al. |
| 2005/0052630 A1 | 3/2005 | Smith et al. |
| 2005/0070841 A1 | 3/2005 | Mathiesen et al. |
| 2006/0025576 A1 | 2/2006 | Miller et al. |
| 2006/0034810 A1 | 2/2006 | Riley et al. |
| 2006/0121005 A1 | 6/2006 | Berenson et al. |
| 2007/0128708 A1 | 6/2007 | Gamelin et al. |
| 2008/0138336 A1 | 6/2008 | Damschroder et al. |
| 2010/0104509 A1 | 4/2010 | King et al. |
| 2013/0216528 A1* | 8/2013 | Cheung .................. A61P 35/02 435/7.1 |
| 2015/0038684 A1 | 2/2015 | Jensen |

FOREIGN PATENT DOCUMENTS

| | | |
|---|---|---|
| EP | 519596 B1 | 2/2005 |
| WO | 9109967 A1 | 7/1991 |
| WO | 9110741 A1 | 7/1991 |
| WO | 9308829 A1 | 5/1993 |
| WO | 9317105 A1 | 9/1993 |
| WO | 9625953 A1 | 8/1996 |
| WO | 9633735 A1 | 10/1996 |
| WO | 9634096 A1 | 10/1996 |
| WO | 9816654 A1 | 4/1998 |
| WO | 9824893 A2 | 6/1998 |
| WO | 9846645 A2 | 10/1998 |
| WO | 9850433 A2 | 11/1998 |
| WO | 0129058 A1 | 4/2001 |
| WO | 0196584 A2 | 12/2001 |
| WO | 2004106381 A1 | 12/2004 |
| WO | 2006130458 A2 | 12/2006 |
| WO | 2009089004 A1 | 7/2009 |
| WO | 2011057124 A1 | 5/2011 |
| WO | 2012025530 A1 | 3/2012 |
| WO | 2012079000 A1 | 6/2012 |
| WO | 2013026839 A1 | 2/2013 |

OTHER PUBLICATIONS

Cancer information from National Institute of Cancer, Apr. 29, 2010, pp. 1-2.
European Patent Application No. 13817144.2—European Search Report dated Feb. 22, 2016.
International Search Report for PCT/US2013/050275 dated Dec. 17, 2013.
Singapore Patent Application No. 11201408787P—Search report dated Oct. 15, 2015.
Baca, et al., "Antibody Humanization Using Monovalent Phage Display", J. Biol. Chem., 272(16):10678-84 (1997).
Bargou, et al., "Tumor Regression in Cancer Patients by Very Low Doses of a T Cell-Engaging Antibody", Science 321, 974-77 (2008).
Barrett, et al., "Treatment of Advanced Leukemia in Mice with mRNA Engineered T Cells", Human Gene Therapy, Dec. 22, 2011, 1575-1586.
Berg, et al., "Selective expansion of a peripheral blood CD8+ memory T cell subset expressing both granzyme B and L-selectin during primary viral infection in renal allograft recipients", Transplant Proc. 30(8), 1998, 3975-3977.
Bierer, et al., "Cyclosporin A and FK506: molecular mechanisms of immunosuppression and probes for transplantation biology", 1993, Curr. Opin. Immun. 5:763-773.
Bird, et al., "Single-chain antigen-binding proteins", 1988, Science 242:423-426.
Brennan, et al., "Preparation of bispecific antibodies by chemical recombination of monoclonal immunoglobulin G1 fragments.", Science. Jul. 5, 1985;229(4708):81-3 (Abstract).
Caldas, et al., "Design and synthesis of germline-based hemi-humanized single-chain Fv against the CD18 surface antigen", Protein Eng., 13(5):353-60 (2000).
Carter, et al., "Humanization of an anti-p185HER2 antibody for human cancer therapy.", Proc. Natl. Acad. Sci. USA, 89:4285-89 (1992).
Choi, et al., "Bispecific antibodies engage T cells for antitumor immunotherapy", Expert Opin Biol Ther, 11:843-853 (2011).
Chothia, et al., "Canonical structures for the hypervariable regions of immunoglobulins.", J Mol Biol. Aug. 20, 1987;196(4):901-17. (Abstract).
Clackson, et al., "Making antibody fragments using phage display libraries", Nature, 352:624-628 (1991) (abstract).
Cougot, et al., "'Cap-tabolism'", Trends in Biochem. Sci. 29, 2001, 436-444 (abstract only).
Couto, et al., "Anti-BA46 Monoclonal Antibody Mc3: Humanization Using a Novel Positional Consensus and in Vivo and in Vibro Characterization.", 1995, Cancer Research 55:1717-1722.
Couto, et al., "Designing Human Consensus Antibodies with Minimal Positional Templates", Cancer Res., 55 (23 Supp):5973s-5977s (1995).
Curran, et al., "Chimeric Antigen receptors for T cell immunotherapy: current understanding and future directions." 2012, The Journal of Gene Medicine 14(6):405-415.
Duchosal, et al., "Immunization of hu-PBL-SCID mice and the rescue of human monoclonal Fab fragments through combinatorial libraries", Nature, 355:258-262 (1992).
Elango, et al., "Optimized transfection of mRNA transcribed from a d(A/T)100 tail-containing vector", Biochim. Biophys. Res. Commun., 330:958-966 (2005) (abstract).
Garland, et al.,"The use of Teflon cell culture bags to expand functionally active CD8+ cytotoxic T lymphocytes", J. Immunol Meth. 227(1-2):53-63, 1999.
Grada, et al., "A chimieric antigen receptor molecule mediates bispecific activation and targeting of T lymphocytes.", Molecular Therapy, 2011, May 19 (Suppl 1), pp. S11, Abstract No. 27.
Griffith, et al., "Human anti-self antibodies with high specificity from phage display libraries", EMBO J., 12:725-734 (1993).
Gruber, et al., "Efficient tumor cell lysis mediated by a bispecific single chain antibody expressed in *Escherichia Coli.*", J. Immunol., 152:5368-74 (1994) (abstract).
Haanen, et al., "Selective Expansion of Cross-reactive CD8+ Memory T Cells by Viral Variants", 1999, J. Exp. Med. 190(9):1319-1328.
Henderson, et al., "Comparison of the effects of FK-506, cyclosporin A and rapamycin on IL-2 production", Immun. 73:316-321, 1991.

(56) References Cited

OTHER PUBLICATIONS

Hollinger, et al., "'Diabodies': Small bivalent and bispecific antibody fragments.", Proc. Natl. Acad. Sci. USA, 90:6444-6448 (1993).
Hoogenboom, et al., "By-passing immunisation. Human antibodies from synthetic repertoires of germline VH gene segments arranged in vitro.", J Mol Biol Sep. 20, 1992;227(2):381-8. (Abstract).
Houbedine, "Production of pharmaceutical proteins from transgenic animals.", 1994, J Biotech 34:269-287.
Hunder, et al., "Treatment of Metastatic Melanoma with Autologous CD4+ T Cells against NY-ESO-1", 2008, New England Journal of Medicine 358:2698-2703.
Huston, et al., "Protein engineering of antibody binding sites: Recovery of sepcific activity in an anti-digoxin single-chain Fv analogue produced in *Escherichia coli*.", 1988, Proc Natl Acad Sci USA 85:5879-5883.
Jakobovits, et al., "Analysis of homozygous mutant chimeric mice: Deletion of the immunoglobulin heavy-chain joining region blocks B-cell development and antibody production", Proc. Natl. Acad Sci. 90, 1993, 2551-2555.
Jakobovits, et al., "Germ-line transmission and expression of a human-derived yeast artificial chromosome", Nature, 362:255-258 (1993).
Johnson, et al., "Human antibody engineering", Current Opinion in Structural Biology 3:564-571 (1993).
Jones, et al., "Replacing the complementarity-determining regions in a human antibody with those from a mouse", Nature, 321:522-525 (1986).
Kalos, et al., "T Cells with Chimeric Antigen Receptors Have Potent Antitumor Effects and Can Establish Memory in Patients with Advanced Leukemia.", Sci Transl Med 3(95):, 2011, 95ra73.
Kappell, et al., "Regulating gene expressio in transgenic animals.", Current Opinion in Biotechnology 1992, 3:548-553.
Kochenderfer, et al., "A Phase I Clinical Trial of Treatment of B-Cell Malignancies with Autologous Anti-CD19-CAR-Transduced T Cells", 2010 ASH Meeting Abstract No. 2865, presented Dec. 5, 2010 (poster abstract), 2010.
Kochenderfer, et al., "B-cell depletion and remissions of malignancy along with cytokine-associated", Blood, Mar. 2012, vol. 119, No. 12, p. 2709-2720.
Kostelny, et al., "Formation of a bispecific antibody by the use of leucine zippers", "Formation of a bispecific antibody by the use of leucine zippers," J. Immunol., vol. 148, No. 5, pp. 1547-1553 (1992), 1992, 1547-1553.
Liu, et al., "Calcineurin is a common target of cyclophilin-cyclosporin A and FKBP-FK506 complexes", Cell 66:807-815, 1991.
Lonberg, et al., "Human Antibodies from Transgenic Mice", Intern. Rev. Immunol. 13, 1995, 65-93.
Marks, et al., "By-passing immunization. Human antibodies from V-gene libraries displayed on phage", J. Mol. Biol. 222:581-597 (1991).
Mccafferty, et al., "Phage antibodies: filamentous phage displaying antibody variable domains", Nature, 348:552-553 (1990).
Mccormack, et al., "Bi-specific TCR-anti CD3 redirected T-cell targeting of NY-ESO-1- and LAGE-1-positive tumors", 2012, Cancer Immunol Immunother 62:773-785.
Milone, et al., "Chimeric receptors containing CD137 signal transduction domains mediate enhanced survival of T cells and increased antileukemic efficacy in vivo", Mol Ther 17(8):, 2009, 1453-64.
Milstein, et al., "Hybrid hybridomas and their use in immunohistochemistry", (1983) Nature 305: 537-39. (abstract).
Morea, et al., "Antibody modeling: implications for engineering and design", Methods, 20(3):267-79 (2000).
Mumtaz, "Design of liposomes for circumventing the reticuloendothelial cells", 1991 Glycobiology 5: 505-10.
Nacheva, et al., "Preventing nondesired RNA-primed RNA extension catalyzed by T7 RNA polymerase", Eur. J. Biochem. 270, 2003, 1485-1465.
Nagorsen, et al., "Immunomodulatory therapy of cancer with T cell-engaging BiTE antibody blinatumomab", 2011, Experimental Cell Research 317(9):1255-60 (Abstract).
Nishikawa, et al., "Nonviral vectors in the new millennium: delivery barriers in gene transfer", Hum. Gene Ther. 12 (8), 2001, 861-870 (abstract only).
Overbeek, "Factors affecting transgenic animal production", Transgenic Animal Technology pp. 96-98 (year 1994).
Padlan, "A possible procedure for reducing the immunogenicity of antibody variable domains while preserving their ligand-binding properties", 1991, Molecular Immunology, 28(4/5):489-498.
Pedersen, et al., "Comparison of surface accessible residues in human and murine immunoglobulin Fv domains. Implication for humanization of murine antibodies.", J. Mol. Biol., 235(3):959-73 (1994).
Presta, et al., "Humanization of an antibody directed against IgE", J. Immunol., 151:2623-32 (1993).
Riechmann, et al., "Reshaping human antibodies for therapy", Nature, 332:323-327 (1988).
Roder, et al., "The EBV-hybridoma technique", Methods Enzymol., 121:140-167 (1986).
Roguska, et al., "A comparison of two murine monoclonal antibodies humanized by CDR-grafting and variable domain resurfacing", Protein Eng., 9(10):895-904 (1996).
Roguska, et al., "Humanization of murine monoclonal antibodies through variable domain resurfacing", PNAS, 91:969-973 (1994).
Rosenberg, et al., "Use of Tumor-Infiltrating Lymphocytes and Interleukin-2 in the Immunotherapy of Patients with Metastatic Melanoma", New Eng. J. of Med. 319:1676-1680, 1988.
Sadelain, et al., "The promise and potential pitfalls of chimeric antigen receptors." 2009 Curr. Opin. Immunol. 21:215-223.
Sandhu, "A rapid procedure for the humanization of monoclonal antibodies.", Gene, 150(2):409-10(1994).
Schenborn, et al., "A novel transcription property of SP6 and T7 RNA polymerases: dependence on template structure", Nuc. Acids Res. 13, 1985, 6223-6236.
Shibaguchi, et al., "A fully human chimeric immune receptor for retargeting T-cells to CEA-expressing tumor cells.", Anticancer Research 26:4067-4072 (2006).
Sims, et al., "A humanized CD18 antibody can block function without cell destruction", J. Immunol., 151:2296-2308 (1993).
Stepinski, et al., "Synthesis and properties of mRNAs containing the novel 'anti-reverse' cap analogs 7-methyl(3'-0-methyl)GpppG and 7-methyl(3'-deoxy)GpppG", RNA 7, 2001, 1468-1495.
Studnicka, et al., "Human-engineered monoclonal antibodies retain full specific binding activity by preserving non-CDR complementarity-modulating residues", Protein Engineering, 7(6):805-814 (1994).
Tan, et al., "'Superhumanized' antibodies: reduction of immunogenic potential by complementarity-determining region grafting with human germline sequences: application to an anti-CD28", J. Immunol., 169:1119-25 (2002).
Traunecker, et al., "Bispecific single chain molecules (Janusins) target cytotoxic lymphocytes on HIV infected cells", EMBO J. 10: 3655-9 (1991).
Tutt, et al., "Trispecific F(ab')3 derivatives that use cooperative signaling via the TCR/CD3 complex and CD2 to activate and redirect resting cytotoxic T cells", J. Immunol. 147: 60-9 (1991) (abstract).
Ui-Tei, et al., "Sensitive assay of RNA interference in *Drosophila* and Chinese hamster cultured cells using firefly luciferase gene as target", 2000 FEBS Letters 479: 79-82.
Vaughan, et al., "Human antibodies with sub-nanomolar affinities isolated from a large non-immunized phage display library", Nature Biotech., 14:309-14 (1996) (abstract).
Verhoeyen, et al., "Reshaping human antibodies: grafting an antilysozyme activity", Science, 239:1534-1536 (1988).
Wall, "Transgenic Livestock: Progress and Prospects for the Future", Theriogenology vol. 45, pp. 57-68 (year 1996).
Weijtens, et al., "Immuno-gene therapy for renal cancer chimeric receptor-mediated lysis of tumor cells", Thesis. pp. 1-128, Oct. 17, 2001.

(56) References Cited

OTHER PUBLICATIONS

Westwood, et al., "Adoptive transfer of T cells modified with a humanized chimeric receptor gene inhibits growth of Lewis-Y-expressing tumors in mice.", PNAS, Dec. 27, 2005, 102(52):19051-19056.

Wu, et al., "Humanization of a murine monoclonal antibody by simultaneous optimization of framework and CDR residues.", J. Mol. Biol., 294:151-162 (1999).

Zhao, et al., "A Herceptin-Based Chimeric Antigen Receptor with Modified Signaling domains Leads to Enhanced Survival of Transduced T Lymphocytes and Antitumor Activity.", J Immunol 183(9), 2009, 5563-5574.

Zhong, et al., "Chimeric antigen receptors combining 4-1BB and CD28 signaling domains augment PI3kinase/AKT/Bcl-XL activation and CD8+ T cell-mediated tumor eradication", Mol Ther, 18:413-420 (2009).

\* cited by examiner

Testing Blina Expression and Function

EP #     RNA
1. CD19-CAR    10ug
2. CD19-CAR    5ug
3. CD19-CAR    5ug + Blina 10ug
4. Blina    10ug
5. GFP    5ug After EP, mix immediately, culture overnight 6. CD19 5ug/GFP (mixture of 1ml EP 2 + 1ml EP 5)
7. CD19 5ug+ Blina 10ug/GFP(mixture of 1ml EP 3 + 1ml EP 5)
8. Blina 10ug/GFP (mixture of 1ml EP 4 + 1ml EP 5)

Mix before CAR staining and CD107a assay

9. CD19 5ug/GFP 2hr (mixture of 1ml EP 2 + 1ml EP 5)
10. CD19 5ug+ Blina 10ug/GFP 2hr(mixture of 1ml EP 3 + 1ml EP 5)
11. Blina 10ug/GFP 2hr(mixture of 1ml EP 4 + 1ml EP 5)
12. NO EP 1. T cell: ND230 OKT stim
2. 100ul EPed T cell in 3ml pre-warmed R10 medium/well
3. EP Condition: 500V, 700us

Figure 2

ENHANCING ACTIVITY OF CAR T CELLS BY CO-INTRODUCING A BISPECIFIC ANTIBODY

CROSS-REFERENCE TO RELATED APPLICATION

This application is a continuation of U.S. patent application Ser. No. 15/690,383, issued as U.S. Pat. No. 10,696,749, a divisional of U.S. patent application Ser. No. 14/410,427, filed Dec. 22, 2014, issued as U.S. Pat. No. 9,765,156, a U.S. national phase application filed under 35 U.S.C. § 371 claiming benefit to International Patent Application No. PCT/US2013/050275 filed on Jul. 12, 2013, which is entitled to priority under 35 U.S.C. § 119(e) to U.S. Provisional Application No. 61/671,535, filed Jul. 13, 2012, each of which is hereby incorporated by reference in its entirety.

BACKGROUND OF THE INVENTION

The development of T cells which are genetically modified to express a chimeric antigen receptor (CAR) has opened the door for many new potential therapies for cancers and other disorders. Generally, CARs comprise an extracellular antigen recognition domain and an intracellular domain.

Some CARs utilize a non-human extracellular antigen recognition domain, which can introduce an unwanted immune response that can jeopardize the therapeutic benefits of CAR mediated tumor recognition and tumor lysis. For example, patients can react to mouse-derived antibodies and create antibodies that are specific to the foreign mouse-derived antibody. This response, termed the human anti-mouse antibody (HAMA) response, can generate symptoms similar to an allergic reaction that ranges from a mild rash to life-threatening complications. Therefore, CARs that comprise an antigen recognition domain derived from human or humanized antibodies may be beneficial because they would not stimulate such a hazardous immune response.

Bispecific T-cell engagers (BiTEs) are bispecific antibodies that bind to a T cell antigen (e.g. CD3) and a tumor antigen. BiTEs have been shown to induce directed lysis of target tumor cells and thus also provide great potential therapies for cancers and other disorders. However, systemic delivery of BiTEs can result in toxicity, and therefore more directed delivery of BiTEs to a specific tumor environment may be desirable.

Thus, there is an urgent need in the art for compositions and methods for treatment of cancer using human or humanized CARs and for the directed delivery of therapeutic bispecific antibodies. The present invention satisfies this unmet need.

SUMMARY OF THE INVENTION

The invention provides an isolated nucleic acid sequence comprising a sequence encoding a chimeric antigen receptor (CAR), wherein the CAR comprises an antigen binding domain derived from a bispecific antibody, a transmembrane domain, and a CD3 zeta signaling domain, further wherein the antigen binding domain is selected from the group consisting of a human antibody, a humanized antibody, an antigen binding fragment thereof, and any combination thereof.

In one embodiment, the isolated nucleic acid sequence encoding a CAR comprises the nucleic acid sequence selected from the group consisting of SEQ ID NO: 20, SEQ ID NO: 21, and SEQ ID NO: 22.

In one embodiment, the antigen-binding fragment is a Fab or a scFv.

In one embodiment, the antigen binding domain binds to a tumor antigen.

In one embodiment, the tumor antigen is associated with a hematologic malignancy.

In one embodiment, the tumor antigen is associated with a solid tumor.

In one embodiment, the tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1 TCR, MAGE A3 TCR, and any combination thereof.

In one embodiment, the CAR further comprises a costimulatory signaling region comprising the intracellular domain of a costimulatory molecule selected from the group consisting of CD27, CD28, 4-1BB, OX40, CD30, CD40, PD-1, lymphocyte function-associated antigen-1 (LFA-1), CD2, CD7, LIGHT, NKG2C, B7-H3, a ligand that specifically binds with CD83, and any combination thereof.

In one embodiment, the isolated nucleic acid sequence encoding a CAR comprises a sequence encoding a bispecific antibody.

In one embodiment, the nucleic acid sequence encoding the bispecific antibody comprises the nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and any combination thereof.

In one embodiment, the bispecific antibody comprises a human antibody, or an antigen-binding fragment thereof.

In one embodiment, the bispecific antibody comprises a humanized antibody, or an antigen-binding fragment thereof.

The invention provides a cell comprising a nucleic acid sequence comprising a sequence encoding a chimeric antigen receptor (CAR), wherein the CAR comprises an antigen binding domain derived from a bispecific antibody, a transmembrane domain, and a CD3 zeta signaling domain, further wherein the antigen binding domain is selected from the group consisting of a human antibody, a humanized antibody, an antigen binding fragment thereof, and any combination thereof.

In one embodiment, the cell is a T cell.

In one embodiment, the cell exhibits an anti-tumor immunity when the antigen binding domain binds to its corresponding antigen.

The invention provides a method for stimulating a T cell-mediated immune response to a target cell population or tissue in a mammal, the method comprising administering to a mammal an effective amount of a cell genetically modified to express a CAR and a bispecific antibody, wherein the CAR comprises an antigen binding domain, a transmembrane domain, and a CD3 zeta signaling domain, further wherein the antigen binding domain is selected from the group consisting of a human antibody, a humanized antibody, an antigen binding fragment thereof, and any combination thereof, thereby stimulating a T cell-mediated immune response to a target cell population or tissue in the mammal.

The invention provides a method for stimulating a T cell-mediated immune response to a target cell population or tissue in a mammal, the method comprising administering to a mammal an effective amount of a cell genetically modified to express a CAR, wherein the CAR comprises an antigen binding domain derived from a bispecific antibody, a transmembrane domain, and a CD3 zeta signaling domain, further wherein the antigen binding domain is selected from a human antibody, a humanized antibody, an antigen binding fragment thereof, and any combination thereof, thereby stimulating a T cell-mediated immune response to a target cell population or tissue in the mammal.

The invention provides a method of providing an anti-tumor immunity in a mammal, the method comprising administering to the mammal an effective amount of a cell genetically modified to express a CAR and a bispecific antibody, wherein the CAR comprises an antigen binding domain, a transmembrane domain, and a CD3 zeta signaling domain, further wherein the antigen binding domain is selected from a human antibody, a humanized antibody, an antigen binding fragment thereof, and any combination thereof, thereby providing an anti-tumor immunity in the mammal.

The invention provides a method of providing an anti-tumor immunity in a mammal, the method comprising administering to the mammal an effective amount of a cell genetically modified to express a CAR, wherein the CAR comprises an antigen binding domain derived from a bispecific antibody, a transmembrane domain, and a CD3 zeta signaling domain, further wherein the antigen binding domain is selected from a human antibody, a humanized antibody, an antigen binding fragment thereof, and any combination thereof, thereby providing an anti-tumor immunity in the mammal.

The invention provides a method of treating a mammal having a disease, disorder or condition associated with an elevated expression of a tumor antigen, the method comprising administering to the mammal an effective amount of a cell genetically modified to express a CAR and a bispecific antibody, wherein the CAR comprises an antigen binding domain, a transmembrane domain, and a CD3 zeta signaling domain, further wherein the antigen binding domain is selected from a human antibody, a humanized antibody, an antigen binding fragment thereof, and any combination thereof, thereby treating the mammal.

The invention provides a method of treating a mammal having a disease, disorder or condition associated with an elevated expression of a tumor antigen, the method comprising administering to the mammal an effective amount of a cell genetically modified to express a CAR, wherein the CAR comprises an antigen binding domain derived from a bispecific antibody, a transmembrane domain, and a CD3 zeta signaling domain, further wherein the antigen binding domain is selected from a human antibody, a humanized antibody, an antigen binding fragment thereof, and any combination thereof, thereby treating the mammal.

The invention provides a method of treating a human with cancer, the method comprising administering to the human a cell genetically engineered to express a CAR and a bispecific antibody, wherein the CAR comprises an antigen binding domain, a transmembrane domain, and a CD3 zeta signaling domain, further wherein the antigen binding domain is selected from a human antibody, a humanized antibody, an antigen binding fragment thereof, and any combination thereof, wherein the cell is a T cell.

The invention provides a method of treating a human with cancer, the method comprising administering to the human a cell genetically engineered to express a CAR, wherein the CAR comprises an antigen binding domain derived from a bispecific antibody, a transmembrane domain, and a CD3 zeta signaling domain, further wherein the antigen binding domain is selected from a human antibody, a humanized antibody, an antigen binding fragment thereof, and any combination thereof, wherein the cell is a T cell.

The invention provides an isolated nucleic acid sequence encoding a bispecific antibody, wherein the nucleic acid sequence comprises the nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

The invention provides a cell comprising a nucleic acid sequence encoding a bispecific antibody, wherein the nucleic acid sequence comprises the nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

The invention provides a method for stimulating a T cell-mediated immune response to a target cell population or tissue in a mammal, the method comprising administering to a mammal an effective amount of a cell genetically modified to express a bispecific antibody.

The invention provides a method of providing an anti-tumor immunity in a mammal, the method comprising administering to the mammal an effective amount of a cell genetically modified to express a bispecific antibody.

The invention provides a method of treating a mammal having a disease, disorder or condition associated with an elevated expression of a tumor antigen, the method comprising administering to the mammal an effective amount of a cell genetically modified to express a bispecific antibody.

The invention provides a method of treating a human with cancer, the method comprising administering to the human a cell genetically engineered to express a bispecific antibody.

In one embodiment, the cell genetically engineered is an autologous T cell.

In one embodiment, the cell secretes the bispecific antibody.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2 is a chart depicting the experimental design for testing Blina RNA electroporated CD19 CART cells. Day 10 stimulated T cells (from ND200) were electroporated as indicated. EP #1 with 10 μg FCM63 CD19 BBZ RNA, EP #2 with 5 μg FCM63 CD19 BBZ RNA, EP #3 with 5 μg FCM63 CD19 BBZ plus 10 µg Blina RNA, EP #4 with 10 µg Blina RNA and EP #5 with 5 µg GFP RNA. #12 was T cell without electroporation. Immediately after electroporation, an aliquot of equal volume (1 ml) of the electroporated T cells were pooled as indicated for #6 to #8. Fifteen hours post electroporation, another aliquot (1 ml) of electroporated cells were pooled as indicated for #9 to #11 and subsequently, the cells were subjected to FACS staining for CAR detection, CD107a assay and cytotoxic T lymphocyte (CTL) assay.

FIG. 9, comprising FIG. 9A shows CD107a expression at day 3, 8 and 12 respectively. FIG. 9B shows both Mean Fluorescence Intensity (MFI) and percentage expression of CD107a at different days post electroporation. FIG. 9B demonstrates higher sensitivity and longer in vitro functional persistence of CD19-CD3 (Blina) RNA electroporated T cells, comparing with CAR RNA T cells.

FIG. 11, comprising FIG. 11A depicts results of CAR staining (Anti-mouse IgG Fab) of cells 1 day post electroporation (note that cMet CAR is a human origin scFv). FIG. 11B depicts results of Cd107a staining (CD8+ gated).

DETAILED DESCRIPTION

Figure 1:
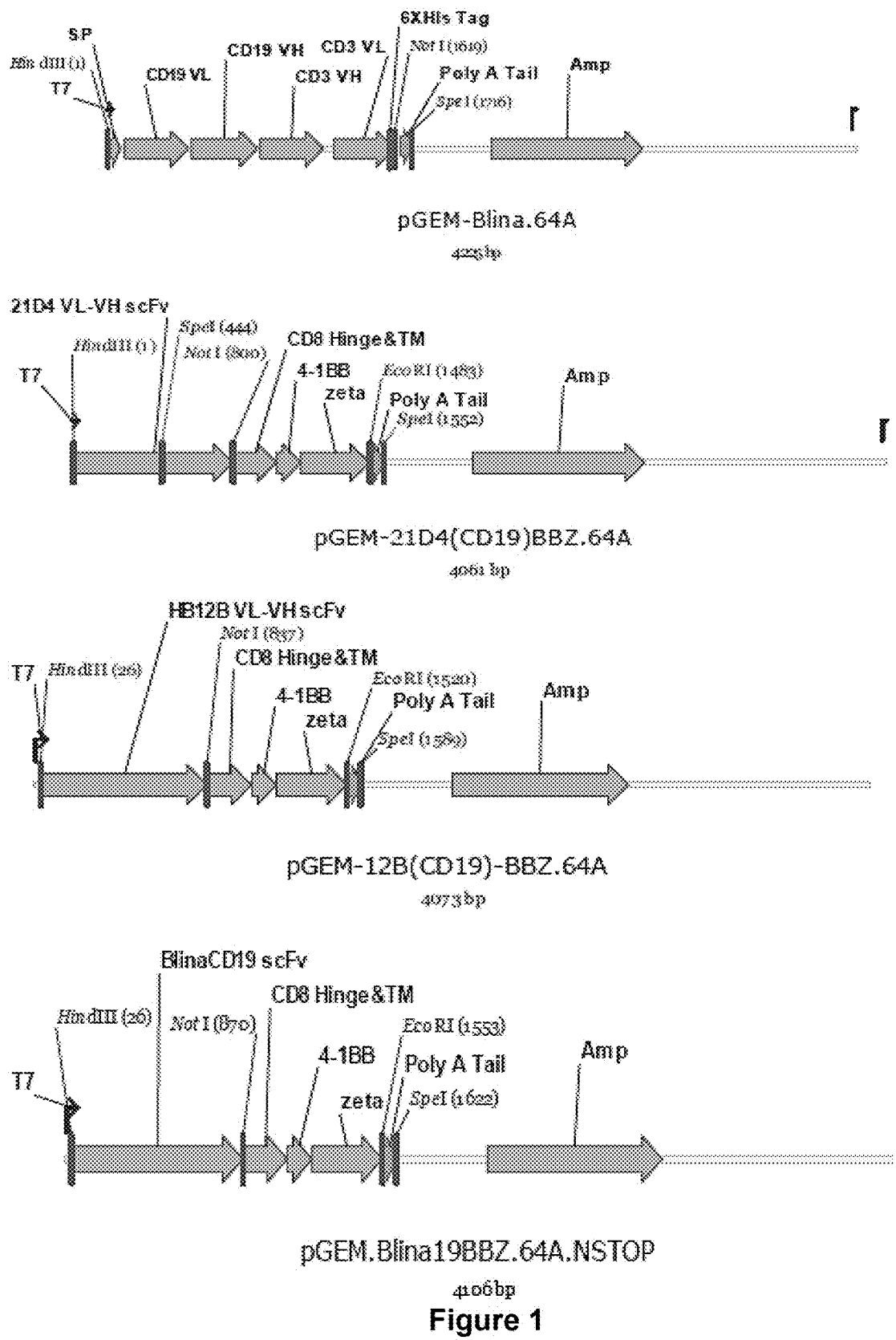
FIG. 1 depicts vector maps of RNA constructs. In vitro transcription (IVT) vector maps for Blinatumomab (pGEM-Blina.64A), CARs with 4-1BB-zeta signaling domains against human CD19 fully human Ab 21D4 (pGEM.D4 (CD19).BBZ.64A), humanized HB12B (pGEM.12B(CD19).BBZ.64A) and mouse origin CD19 scFv from Blinatumomab (pGEM.Blina.19BBZ.64A).

The invention relates to compositions and methods for treating cancer, including, but not limited to, hematologic malignancies and solid tumors. The present invention relates to a strategy of adoptive cell transfer of T cells modified to express a bispecific antibody. In another embodiment, the invention relates to adoptive cell transfer of T cells modified to express a chimeric antigen receptor (CAR).

In one embodiment, the T cells are modified to express a bispecific antibody. A bispecific antibody comprises two different binding specificities and thus binds to two different antigens. In one embodiment, the bispecific antibody comprises a first antigen recognition domain that binds to a first antigen and a second antigen recognition domain that binds to a second antigen. In one embodiment, the first antigen recognition domain binds to a tumor associated antigen. In one embodiment, the second antigen recognition region binds to an antigen on T cells. In a particular embodiment, the second antigen recognition region binds to CD3 on T cells. In one embodiment, the invention relates to adoptive cell transfer of T cells modified to express a human or humanized bispecific antibody.

In one embodiment, the T cells are modified to express a CAR. CARs are molecules that combine antibody-based specificity for a desired antigen (e.g., tumor antigen) with a T cell receptor-activating intracellular domain to generate a chimeric protein that exhibits a specific anti-tumor cellular immune activity. In one embodiment, the invention relates to adoptive cell transfer of T cells modified to express a human or humanized CAR.

In another embodiment, the invention relates to adoptive cell transfer of T cells modified to express a bispecific antibody and a chimeric antigen receptor (CAR).

The present invention relates generally to the use of T cells genetically modified to express a desired CAR, as well as to the use of T cells genetically modified to express a desired CAR in combination with a desired bispecific antibody. T cells expressing a CAR are referred to herein as CAR T cells or CAR modified T cells. Preferably, the cell can be genetically modified to express an antibody binding domain on its surface, conferring novel antigen specificity that is MHC independent. In some instances, the T cell is genetically modified to express a CAR that combines an antigen recognition domain of a specific antibody with an intracellular domain of the CD3-zeta chain or FcγRI protein into a single chimeric protein. In some instances, the CAR T cell is genetically modified to express a CAR that combines an antigen recognition domain of a specific antibody with an intracellular domain of the CD3-zeta chain or FcγRI protein into a single chimeric protein, as well as a bispecific antibody.

In one embodiment, the CAR of the invention comprises an extracellular domain having an antigen recognition domain, a transmembrane domain, and a cytoplasmic domain. In one embodiment, the CAR can comprise a humanized antibody, or fragment thereof. In one embodiment, the CAR can comprise a human antibody, or fragment thereof. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In some embodiments, the extracellular domain also comprises a hinge domain. Preferably, the hinge domain comprises the CD8α hinge domain.

With respect to the cytoplasmic domain, the CAR of the invention can be designed to comprise any desired cytoplasmic domain(s) useful in the context of the CAR of the invention. In one embodiment, the cytoplasmic domain of the CAR can be designed to further comprise the signaling domains of CD3-zeta, 4-1BB, and/or CD28. For example, the cytoplasmic domain of the CAR can include but is not limited to CD3-zeta, 4-1BB and CD28 signaling modules and combinations thereof. Accordingly, the invention provides CART cells and methods of their use for adoptive therapy.

In one embodiment, the T cells are modified to express a bispecific antibody, in combination with a CAR. In one embodiment co-expression of the bispecific antibody and the CAR improves tumor recognition and tumor lysis.

In one embodiment, the modified T cells of the invention can be generated by introducing a lentiviral vector comprising a desired bispecific antibody into a T cell. In one embodiment, the modified T cells of the invention can be generated by introducing a lentiviral vector comprising a desired CAR, for example a CAR comprising anti-CD19, CD8α hinge, and CD3zeta signaling domains into a T cell. In one embodiment, the modified T cells of the invention can be generated by introducing a lentiviral vector comprising a desired bispecific antibody in combination with a lentivirus vector comprising a desired CAR into a T cell. In another embodiment, the modified T cells of the invention can be generated by introducing a lentiviral vector comprising a desired CAR, for example a CAR comprising anti-CD19, CD8α hinge, and CD3zeta signaling domains, and a desired bispecific antibody into a T cell. In one embodiment, the modified T cells of the invention are able to replicate in vivo resulting in long-term persistence that can lead to sustained tumor control.

In one embodiment, the modified T cells of the invention can be generated by transfecting an RNA encoding a desired bispecific antibody into a T cell. In one embodiment, the modified T cells of the invention can be generated by transfecting an RNA encoding a desired CAR, for example a CAR comprising anti-CD19, CD8α hinge, and CD3zeta signaling domains into a T cell. In one embodiment, the modified T cells of the invention can be generated by transfecting an RNA encoding a desired bispecific antibody in combination with an RNA encoding the desired CAR into a T cell. In another embodiment, the modified T cells of the invention can be generated by transfecting an RNA encoding the desired CAR, for example a CAR comprising anti-CD19, CD8α hinge, and CD3zeta signaling domains, and further encoding a desired bispecific antibody into the cells. In one embodiment, both the CAR and the bispecific antibody are transiently expressed in the genetically modified T cells.

In one embodiment, the modified T cells of the invention can be generated by transfecting an RNA encoding the desired CAR, for example a CAR comprising anti-CD19, CD8α hinge, and CD3zeta signaling domains into a T cell, and introducing a lentiviral vector comprising the desired bispecific antibody. In another embodiment, the modified T cells of the invention can be generated by introducing a lentiviral vector comprising a desired CAR, for example a CAR comprising anti-CD19, CD8α hinge, and CD3zeta signaling domains into a T cell, and transfecting an RNA encoding a desired bispecific antibody into the cell.

In one embodiment the invention relates to administering a genetically modified T cell expressing a humanized bispecific antibody, a humanized CAR, or combination thereof for the treatment of a patient having cancer or at risk of having cancer using lymphocyte infusion. In another embodiment the invention relates to administering a genetically modified T cell expressing a bispecific antibody, a CAR, or combination thereof for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

In one embodiment, the invention relates to a CAR comprising human or humanized antibodies, or fragments thereof. In one embodiment, the invention relates to a bispecific antibody comprising human or humanized antibodies, or fragments thereof. The invention is based upon the discovery that constructs derived from human or humanized antibodies specifically recognize tumor antigens. Therefore, such human or humanized constructs can be used to treat cancers and other disorders and avoid the risk of inducing an immune response.

In one embodiment, the invention relates to genetically modified T cells expressing a CAR and a bispecific antibody. The present invention is based upon the finding that co-expression of a CAR and a bispecific antibody significantly enhanced tumor reactivity and tumor lysis. Further, induction of T cells to produce a CAR and a bispecific antibody recruits non-reactive T cells to become tumor reactive. This allows a method to localize the delivery of anti-tumor agents to the specific tumor microenvironment using T cells. In one embodiment, CAR T cells traffic the bispecific antibody to the site of the tumor, thereby reducing the toxicity associated with systemic delivery of bispecific antibodies.

In one embodiment, the invention relates to genetically modified T cells expressing a bispecific antibody. The present invention is partly based on the finding that a T cell modified to express a bispecific antibody performs equally as well as a T cell modified to express a CAR.

In yet another embodiment, the invention relates generally to the treatment of a patient at risk of developing cancer. The invention also includes treating a malignancy or an autoimmune disease in which chemotherapy and/or immunotherapy in a patient results in significant immunosuppression in the patient, thereby increasing the risk of the patient of developing cancer.

The invention includes using T cells expressing an anti-CD19 CAR and a bispecific antibody. In one embodiment, T cells expressing the anti-CD19 CAR and bispecific antibody of the invention display enhanced tumor recognition and tumor lytic activity compared to T cells expressing anti-CD19 CAR alone. In some instances, the modified T cells of the invention infused into a patient can eliminate cancerous cells in vivo in patients with cancer. However, the invention is not limited to CAR-expressing T cells. Rather, the invention includes any antigen binding domain fused with one or more intracellular domains selected from the group of a CD137 (4-1BB) signaling domain, a CD28 signaling domain, a CD3zeta signal domain, and any combination thereof.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

A "bispecific antibody," as used herein, refers to an antibody having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) Nature 305: 537-39. Alternatively, bispecific antibodies can be prepared using chemical linkage. See, e.g., Brennan et al. (1985) Science 229:81. Bispecific antibodies include bispecific antibody fragments. See, e.g., Holliger et al. (1993) Proc. Natl. Acad. Sci. U.S.A. 90:6444-48, Gruber et al. (1994) J. Immunol. 152:5368.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject," "patient" and "individual" are used interchangeably herein and are intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for treating cancer as well as other diseases. The cancer may be a hematological malignancy, a solid tumor, a primary or a metastasizing tumor. Other diseases treatable using the compositions and methods of the invention include viral, bacterial and parasitic infections as well as autoimmune diseases.

In one embodiment, the invention provides a cell (e.g., T cell) engineered to express a CAR wherein the CAR T cell exhibits an antitumor property. In a preferred embodiment, the CAR is a humanized CAR. The CAR of the invention can be engineered to comprise an extracellular domain having an antigen binding domain fused to an intracellular signaling domain of the T cell antigen receptor complex zeta chain (e.g., CD3 zeta). The CAR of the invention when expressed in a T cell is able to redirect antigen recognition based on the antigen binding specificity. An exemplary antigen is CD19 because this antigen is expressed on B cell lymphomas. However, the invention is not limited to targeting CD19. Rather, the invention includes any antigen binding domain that when bound to its cognate antigen, affects a tumor cell so that the tumor cell fails to grow, is prompted to die, or otherwise is affected so that the tumor burden in a patient is diminished or eliminated. The antigen binding domain is preferably fused with an intracellular domain from one or more of a costimulatory molecule and a zeta chain. Preferably, the antigen binding domain is fused with one or more intracellular domains selected from the group of a CD137 (4-1BB) signaling domain, a CD28 signaling domain, a CD3zeta signal domain, and any combination thereof.

In one embodiment, the invention provides a T cell engineered to express a bispecific antibody. In one embodiment, the bispecific antibody comprises a human antibody, or fragment thereof. In one embodiment, the bispecific antibody comprises a humanized antibody, or fragment thereof. The bispecific antibody comprises two different binding specificities. In one embodiment, the bispecific antibody comprises a region that binds to a tumor antigen. In one embodiment, the bispecific antibody comprises a region that binds to a T cell antigen. For example, in one embodiment, the bispecific antibody binds to CD3.

In one embodiment, the invention provides a T cell engineered to express a CAR and a bispecific antibody. In some embodiments, the CAR is a humanized CAR. In some embodiments, the bispecific antibody recognizes the same antigen as recognized by the CAR. In other embodiments, the bispecific antibody recognizes a different antigen. The present invention is based upon the discovery that T cells modified to express both a CAR and a bispecific antibody display enhanced tumor recognition and tumor lytic activity. Further, co-expression or co-introduction of a CAR and a bispecific antibody allows non-reactive T cells to become tumor reactive. Thus, the present invention provides the specific delivery of the bispecific antibody to a tumor microenvironment, thereby alleviating toxicity associated with systemic delivery of bispecific antibodies.

In some embodiments, the present invention is directed to retroviral or lentiviral vectors encoding a CAR and/or bispecific antibody that is stably integrated into a T cell and stably expressed therein. In other embodiments, the present invention is directed to RNA encoding a CAR and/or a bispecific antibody that is transfected into a T cell and transiently expressed therein. Transient, non-integrated expression of the CAR and bispecific antibody in a cell mitigates concerns associated with permanent and integrated expression in a cell.

In some embodiment, the present invention includes introducing a bispecific antibody along with a CD19 CAR in order to enhance the anti-tumor activity of the CAR engineered T cell. In one embodiment, the bispecific antibody is in the form of RNA. In another embodiment, the CD19 CAR is in the form of RNA. In yet another embodiment, the bispecific antibody and CD19 CAR are in the form of RNA.

In one embodiment, introducing bispecific antibody RNA along with CD19 CARs enhances the anti-tumor activity of CAR engineered T cells. Further, introduction of bispecific antibody RNA into T cells recruits non-tumor reactive T cells to become tumor reactive, which provides a novel way of delivering and trafficking an antitumor drug into cancer patients by using T cells. This reduces the toxicity of systemic BiTEs, by focusing the delivery of the bispecific antibody to the tumor microenvironment by virtue of the CAR T cell that carries the cargo (BiTE) to the site of the tumor.

Compositions

The present invention provides a chimeric antigen receptor (CAR) comprising an extracellular and intracellular domain. In some embodiments, the CAR of the invention is humanized. The extracellular domain comprises a target-specific binding element otherwise referred to as an antigen binding domain. In some embodiments, the extracellular domain also comprises a hinge domain. The intracellular domain or otherwise the cytoplasmic domain comprises a costimulatory signaling region and a zeta chain portion. The costimulatory signaling region refers to a portion of the CAR comprising the intracellular domain of a costimulatory molecule. Costimulatory molecules are cell surface molecules other than antigen receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The present invention includes retroviral and lentiviral vector constructs expressing a CAR that can be directly transduced into a cell. The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the CAR.

Preferably, the CAR comprises an extracellular domain, a transmembrane domain and a cytoplasmic domain. The extracellular domain and transmembrane domain can be derived from any desired source of such domains. In some instances, the hinge domain of the CAR of the invention comprises the CD8α hinge domain. In one embodiment, the CAR comprises the nucleic acid sequence of any one of SEQ ID NOs: 20-23. In one embodiment, the CAR comprises the amino acid sequence encoded by the nucleic acid sequence of any one of SEQ ID NOs: 20-23.

Antigen Binding Domain

In one embodiment, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR of the invention can be engineered to target a tumor antigen of interest by way of engineering a desired antigen binding domain that specifically binds to an antigen on a tumor cell. In the context of the present invention, "tumor antigen" or "hyperporoliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding domain of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding domain portion of the CAR targets an antigen that includes but is not limited to CD19, CD20, CD22, ROR1, Mesothelin, CD33/IL3Ra, c-Met, PSMA, Glycolipid F77, EGFRvIII, GD-2, MY-ESO-1 TCR, MAGE A3 TCR, and the like.

Depending on the desired antigen to be targeted, the CAR of the invention can be engineered to include the appropriate antigen bind moiety that is specific to the desired antigen target. For example, if CD19 is the desired antigen that is to be targeted, an antibody for CD19 can be used as the antigen bind moiety for incorporation into the CAR of the invention. In one embodiment, the antigen binding domain portion of the CAR of the invention targets CD19.

The antigen binding domain can be any domain that binds to the antigen including but not limited to monoclonal antibodies, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or fragment thereof. Thus, in one embodiment, the antigen biding domain portion comprises a human antibody or a fragment thereof. For example, the antigen binding domain of SEQ ID NO: 20 is fully human in origin.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-CD19 antibodies directed against the human CD19 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Alternatively, in some embodiments, a non-human antibody is humanized, where specific sequences or regions of the antibody are modified to increase similarity to an antibody naturally produced in a human. In one embodiment, the antigen binding domain portion is humanized. For example, the antigen binding domain of SEQ ID NO: 21 is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A "humanized" antibody retains a similar antigenic specificity as the original antibody, i.e., in the present invention, the ability to bind human CD19 antigen. However, using certain methods of humanization, the affinity and/or specificity of binding of the antibody for human CD19 antigen may be increased using methods of "directed evolution," as described by Wu et al., J. Mol. Biol., 294:151 (1999), the contents of which are incorporated herein by reference herein in their entirety.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, ICOS. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3-zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention is exemplified primarily with 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta. In another embodiment, the cytoplasmic domain is designed to comprise the signaling domain of CD3-zeta and the signaling domain of 4-1BB.

Bispecific Antibodies

The present invention also provides a bispecific antibody. A bispecific antibody comprises two different binding specificities and thus binds to two different antigens. In one embodiment, the bispecific antibody comprises a first antigen recognition domain that binds to a first antigen and a second antigen recognition domain that binds to a second antigen. In one embodiment, the first antigen recognition domain binds to a tumor associated antigen. As described elsewhere herein, the bispecific antibody can recognize the same or different tumor antigen recognized by the CAR of the invention. In one embodiment, the second antigen recognition region binds to a T cell antigen. For example, the bispecific antibody can recognize CD3. In some instances, a bispecific antibody that recognizes a T cell antigen is referred to as a Bispecific T Cell Engager (BiTE). An exemplary BiTE is Blinatumomab (obtainable from Amgen) which comprises an anti-CD19 domain and an anti-CD3 domain. Blinatumomab (Blina) is encoded by the nucleic acid sequence of SEQ ID NO: 1. However, the present invention is not limited by the use of any particular bispecific antibody. Rather, any bispecific antibody or BiTE can be used. Examples of tumor associated antigens are described elsewhere herein, all of which may be targeted by the bispecific antibody of the present invention. In one embodiment, the bispecific antibody comprises a human antibody, a humanized antibody, or fragments thereof. Techniques for making human and humanized antibodies are described elsewhere herein.

Techniques for making bispecific antibodies include, but are not limited to, recombinant co-expression of two immunoglobulin heavy chain-light chain pairs having different specificities (see Milstein and Cuello, Nature 305: 537 (1983), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science 229:81 (1985)); using leucine zippers to produce bispecific antibodies (see, e.g., Kostelny et al., J. Immunol. 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991). Engineered antibodies with three or more functional antigen binding sites, including "Octopus antibodies," are also included herein (see, e.g. US 2006/0025576A1). Bispecific antibodies can be constructed by linking two different antibodies, or portions thereof. For example, a bispecific antibody can comprise Fab, F(ab')$_2$, Fab', scFv, and sdAb from two different antibodies.

Vectors

The present invention encompasses a nucleic acid construct comprising sequences of a CAR, wherein the sequence comprises the nucleic acid sequence of an antigen binding domain operably linked to the nucleic acid sequence of an intracellular domain. An exemplary intracellular domain that can be used in the CAR of the invention includes but is not limited to the intracellular domain of CD3-zeta, CD28, 4-1BB, and the like. In some instances, the CAR can comprise any combination of CD3-zeta, CD28, 4-1BB, and the like. The present invention also encompasses a nucleic acid construct comprising sequences of bispecific antibody. The present invention further encompasses a nucleic acid construct comprising sequences of a CAR, wherein the sequence comprises the nucleic acid sequence of an antigen binding domain operably linked to the nucleic acid sequence of an intracellular domain, and wherein the nucleic acid construct also comprises the nucleic acid sequence of a bispecific antibody.

In one embodiment, the CAR of the invention comprises anti-CD19 antigen binding domain, human CD8 hinge, and CD3zeta signaling domains. In one embodiment, the CAR of the invention comprises the nucleic acid sequence set forth in one of SEQ ID NOs: 20-23.

In one embodiment, the bispecific antibody of the antibody comprises the nucleic acid sequence set forth in one of SEQ ID NOs: 1-19.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a nucleic acid of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the nucleic acid has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In one embodiment, the genetically modified T cells of the invention are modified through the introduction of RNA. In one embodiment, an in vitro transcribed RNA CAR can be introduced to a cell as a form of transient transfection. In another embodiment, the RNA CAR is introduced along with an in vitro transcribed RNA encoding a bispecific antibody. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR and/or bispecific antibody of the present invention. By way of example, the template comprises an extracellular domain comprising a single chain variable domain of an anti-tumor antibody; a transmembrane domain comprising the hinge and transmembrane domain of CD8a; and a cytoplasmic domain comprises the signaling domain of CD3-zeta. By way of another example, the template comprises a bispecific antibody. By way of another example, the template comprises an extracellular domain comprising a single chain variable domain of an anti-tumor antibody; a transmembrane domain comprising the hinge and transmembrane domain of CD8a; and a cytoplasmic domain comprises the signaling domain of CD3-zeta, and a bispecific antibody. In one embodiment, the template for the RNA-CAR is one of SEQ ID NO: 20-23. In one embodiment, the template for an RNA encoding a bispecific antibody is one of SEQ ID NO: 1-19.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, it is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified T Cells

In some embodiments, the CAR sequences and/or bispecific antibody sequences are delivered into cells using a retroviral or lentiviral vector. CAR-expressing and/or bispecific antibody expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences and/or bispecific antibody sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rittman.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) modified to express a bispecific antibody, a CAR, or a combination thereof, where the CAR combines an antigen recognition domain of a specific antibody with an intracellular domain of CD3-zeta, CD28, 4-1BB, or any combinations thereof. Therefore, in some instances, the transduced T cell can elicit a CAR-mediated T-cell response.

In one embodiment, the invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3-zeta, and a costimulatory signaling region.

In one embodiment, the present invention includes a type of cellular therapy where T cells are genetically modified to express a bispecific antibody, a CAR, or combination thereof, and the T cell is infused to a recipient in need thereof. The infused cell is able to kill tumor cells in the recipient. Unlike antibody therapies, in some embodiments the modified T cells are able to replicate in vivo resulting in long-term persistence that can lead to sustained tumor control.

In one embodiment, the T cells of the invention can undergo robust in vivo T cell expansion and can persist for an extended amount of time. In another embodiment, the T cells of the invention evolve into specific memory T cells that can be reactivated to inhibit any additional tumor formation or growth.

Without wishing to be bound by any particular theory, the anti-tumor immunity response elicited by the—modified T cells may be an active or a passive immune response. In addition, the mediated immune response may be part of an adoptive immunotherapy approach in which—modified T cells induce an immune response specific to the targeted antigen recognized by the CAR and/or bispecific antibody.

In one embodiment, modified T cells of the invention secrete the bispecific antibody into the extracellular space of the tumor microenvironment. This effective delivery method reduces the toxicity associated with systemic delivery of bispecific antibodies.

In one embodiment, the present invention provides the use of a modified T cell to effectively deliver a bispecific antibody to a particular region (i.e. a tumor microenvironment). In one embodiment, T cells modified to express a CAR and a bispecific antibody target a specific tumor microenvironment through the antigen binding domain of the CAR expressed on the surface of the CAR. Further, in one embodiment, the CAR-mediated delivery of bispecific antibodies arms non-modified T cells of the tumor microenvironment with the therapeutic bispecific antibody. In one embodiment, the bispecific antibody binds to a T cell and a tumor antigen. This form of bispecific antibody, known as a BiTE, works together with the CAR to specifically recognize and kill tumors. In one embodiment, the methods of the present invention comprise administering T cells modified to express both a CAR and a bispecific antibody to a subject to enhance tumor recognition, immune response, and tumor lysis, compared to delivery of T cells modified with only a CAR.

While the data disclosed herein specifically described IVT RNA CAR comprising an anti-CD19 region, a human CD8α hinge and transmembrane region, and 4-1BB and CD3zeta signaling domains, the invention should be construed to include any number of variations for each of the components of the construct as described elsewhere herein. That is, the invention includes the use of any antigen binding domain in the CAR to generate a CAR-mediated T-cell response specific to the antigen binding domain. For example, the antigen binding domain in the CAR of the invention can target a tumor antigen for the purposes of treat cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, meningioma, neuroblastoma, retinoblastoma and brain metastases).

In one embodiment, the CAR and bispecific antibody of the invention are designed to treat a particular cancer. For example, the CAR and bispecific antibody designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In another embodiment, the CAR and bispecific antibody can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, the CAR and bispecific antibody can be designed to target mesothelin to treat mesothelioma, pancreatic cancer, ovarian cancer, and the like. In another embodiment, the CAR and bispecific antibody can be designed to target CD33/IL3Ra to treat acute myelogenous leukemia and the like. In a further embodiment, the CAR and bispecific antibody can be designed to target c-Met to treat triple negative breast cancer, non-small cell lung cancer, and the like.

In one embodiment, the CAR and bispecific antibody can be designed to target PSMA to treat prostate cancer and the like. In another embodiment, the CAR and bispecific antibody can be designed to target Glycolipid F77 to treat prostate cancer and the like. In a further embodiment, the CAR and bispecific antibody can be designed to target EGFRvIII to treat gliobastoma and the like.

In one embodiment, the CAR and bispecific antibody can be designed to target GD-2 to treat neuroblastoma, melanoma, and the like. In another embodiment, the CAR and bispecific antibody can be designed to target NY-ESO-1 TCR to treat myeloma, sarcoma, melanoma, and the like. In a further embodiment, the CAR and bispecific antibody can be designed to target MAGE A3 TCR to treat myeloma, sarcoma, melanoma, and the like.

However, the invention should not be construed to be limited to solely to the antigen targets and diseases disclosed herein. Rather, the invention should be construed to include any antigenic target that is associated with a disease where a CAR and/or bispecific antibody can be used to treat the disease.

The modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR and/or bispecific antibody to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing compositions disclosed herein. The modified cell can be administered to a mammalian recipient to provide a therapeutic benefit. The mammalian recipient may be a human and the modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as Flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the modified T cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the modified T cells of the invention.

The modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients.

Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i. v.) injection, or intraperitoneally. In one embodiment, the T cell compositions of the present invention are administered to a patient by intradermal or subcutaneous injection. In another embodiment, the T cell compositions of the present invention are preferably administered by i. v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Enhancing Anti-Tumor Activity of RNA CAR T Cells by Co-Introducing Bispecific Antibody RNA (Bis-RNA)

Treating cancer patients with adoptive transfer of CAR re-directed T cells has shown promising results. Electroporation of RNA encoding CARs into T cells provides a safer, easier and probably more efficient alternative way to currently commonly used lenti- or retro-viral based gene deliver based therapies. The findings from recent clinical trials demonstrated that CARs derived from mouse Abs showed evidence of human anti-mouse antibody (HAMA) response, which potentially jeopardized the therapy. Thus, CARs derived from human or humanized Abs provide a desirable alternative to mouse derived sequences, especially when repeated infusions are needed by using RNA electroporated T cells to treat cancer patients.

The studies disclosed herein describe: 1) the generation of anti-human CD19 CARs derived from human origin that eliminate potential HAMA when using CARs by either lentiviral transduction or RNA electroporation; 2) the co-introduction of a gene (or mRNA) encoding a bispecific Ab derived from human (or humanized) Abs. Here exemplary CARs were constructed (FIG. 1) with 4-1BB-zeta signaling domains against human CD19 from anti-CD19 Abs that is either fully human in origin (clone 21D4; U.S. Pat. App. No.: 2010/0104509 A1), or humanized (clone HB12B; U.S. Pat. App. No.: US2008/0138336 A1) or mouse origin (CD19 scFv) from Blinatumomab (anti-CD19/anti-CD3 bispecific Ab); U.S. Pat. No. 7,575,923 B2). In addition to testing CD19-CD3 bispecific Ab RNA (Bis-RNA), mesothelin (ss1)-CD3 (ss1HL-Blina and ss1-BlinaLH), cMet-CD3 (cMet-Blina), PSCA-CD3 (PSCA-Blina) and GD2-CD3 (Gd2-Blina) Bis-RNAs were constructed. To humanize Blina Bis-RNA, constructs were made and both murine CD19 and CD3 scFv were replaced by human or humanized scFv against CD19 (21D4) and CD3 (27H5 VL1, 27H5 VL2, 28F11, DIVHv5, DIVHv6 and DIVHv7) respectively, which resulted 13 constructs: D4-Blina, D4-VL1, D4-VL2, D4-F11, D4-Hv5, D4-Hv6, D4-Hv7, Blina-VL1, Blina-VL2, Blina-F11, Blina-Hv5, Blina-Hv6 and Blina-Hv7.

IVT RNA generated from the constructs encoding these CD19 CARs was electroporated into T cells. CAR expression and anti-tumor activity were compared with CD19 CAR derived from FMC63 (currently used for CART19 trials). The experimental design for the results presented herein is shown in FIG. 2. The results showed that all the new CD19 CARs could be efficiently expressed. In spite of the slightly reduced expression as compared with the FMC63 CAR, their anti-tumor activity assayed by CD107a detection was comparable to the control FMC63 CAR.

Figure 3:
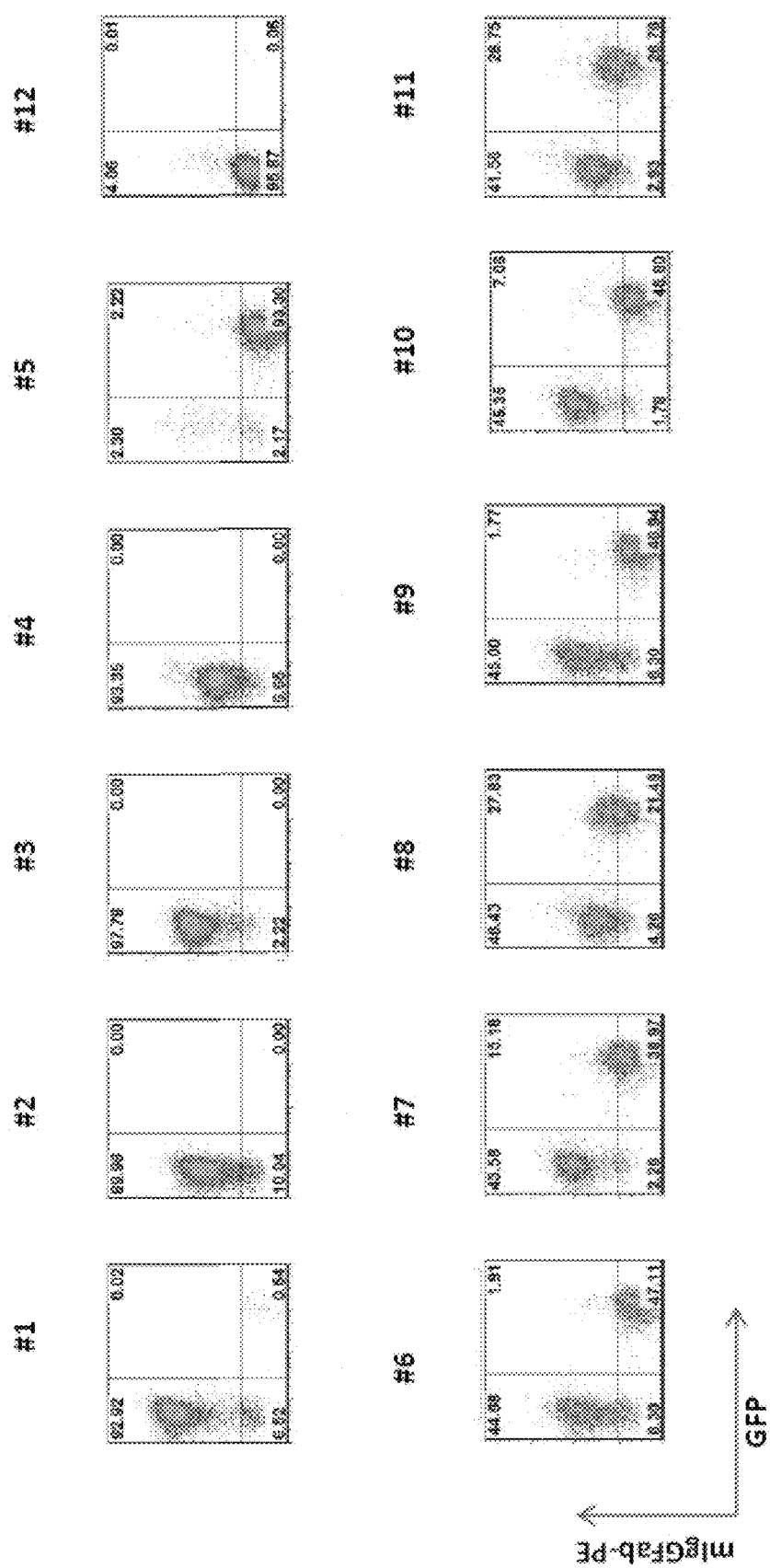
FIG. 3 is a series of graphs depicting CAR staining of CD19 CAR, Blina RNA electroporated T cells and GFP RNA electroporated T cells incubated with Blina RNA electroporated T cells. Fifteen hours after electroporation, the T cells for all the treatments as shown in FIG. 2 were stained with a goat anti-mouse Fab. The number shown above each plot refers to the conditions listed in FIG. 2. The results show that not only could CD19 CAR RNA electroporated T cells be stained for CAR expression, but the Blina bis-RNA alone (#4) electroporated, and the GFP RNA electroporated T cells that were co-incubated with T cells that had been electroporated with Blina bis-RNA (#7, #8, #10, #11) could also be stained. This demonstrates that the CD19-CD3 bispecific Ab secreted by Blina electroporated T cells could bind to CD3 of GFP electroporated T cells.

To examine whether co-introduction of a gene (or mRNA) encoding anti-CD19/anti-CD3 bispecific Ab further enhanced anti-tumor activity of CAR engineered T cells, the gene encoding Blinatumomab (Blina) was synthesized by PCR, which was then constructed into IVT vector pGEM.64A to generate pGEM-Blina.64A. T cells were co-electroporated with the RNA encoding Blinatumomab (Blina) and with CD19 CAR RNA (FCM63 CAR), or alternatively were electroporated with Blina RNA alone, and were compared with T cells electroporated with FCM63 CD19 CAR RNA alone. Cells were stained for the presence of mouse IgG, which showed that not only did CD19 CAR RNA electroporated cells stain positive for CAR expression, but also the co-incubation of Blina Bis-RNA electroporated cells with GFP-RNA electroporated cells resulted in positive staining in a majority of cells (FIG. 3). This data is consistent with the explanation that the CD19-CD3 bispecific Ab secreted by Blina electroporated T cells could bind to CD3 of GFP electroporated T cells.

Figure 4:
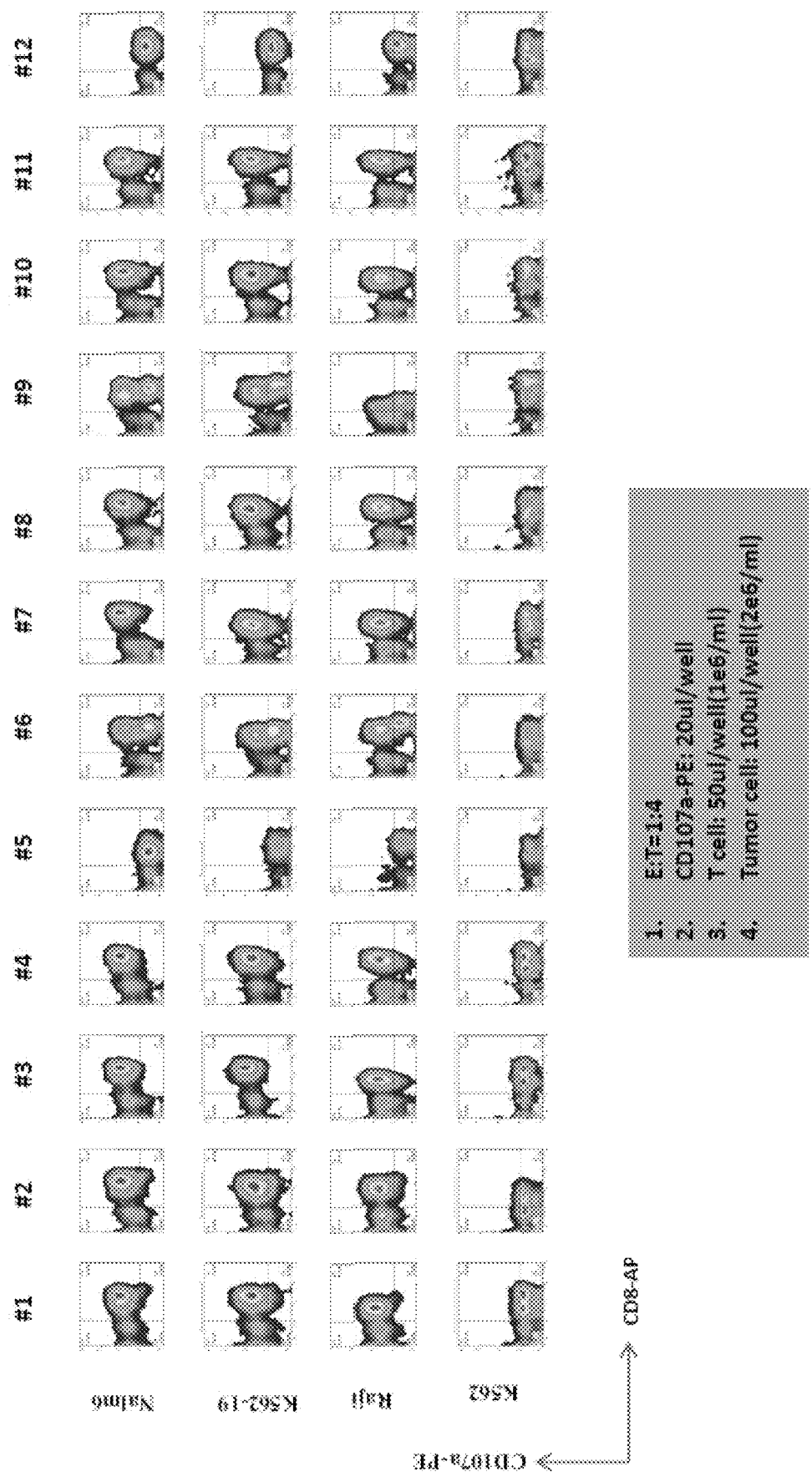
FIG. 4 is a series of graphs depicting the results of experiments illustrating that T cells electroporated with Blina bis-RNA "BITE" could specifically recognize tumors. Fifteen hours after electroporation, T cells were subjected to a CD107a degranulation assay. Fifteen hours after electroporation, the T cells for all the conditions shown in FIG. 2 were co-cultured with different types of cells that express CD19 (Nalm6, K562-CD19 and Raji) or the CD19 negative tumor K562. The number shown above each plot are the conditions listed in FIG. 2. The results demonstrate that T cells electroporated with Blina bis-RNA specifically recognized CD19 positive tumors.

Electroporated cells were co-cultured with CD19 expressing cells (Nalm6, K562-CD19, and Raji) or with the CD19 negative cells (K562). A CD107a degranulation assay was performed, which showed that that Blina Bis-RNA alone could enable electroporated T cells to specifically detect tumor as efficiently as FMC63 CD19 RNA electroporated T cells (FIG. 4). Co-electroporation of Blina RNA with CD19 CAR RNA could further enhance tumor reactivity, as evidenced by the CD107a assay (FIG. 4).

Figure 5:
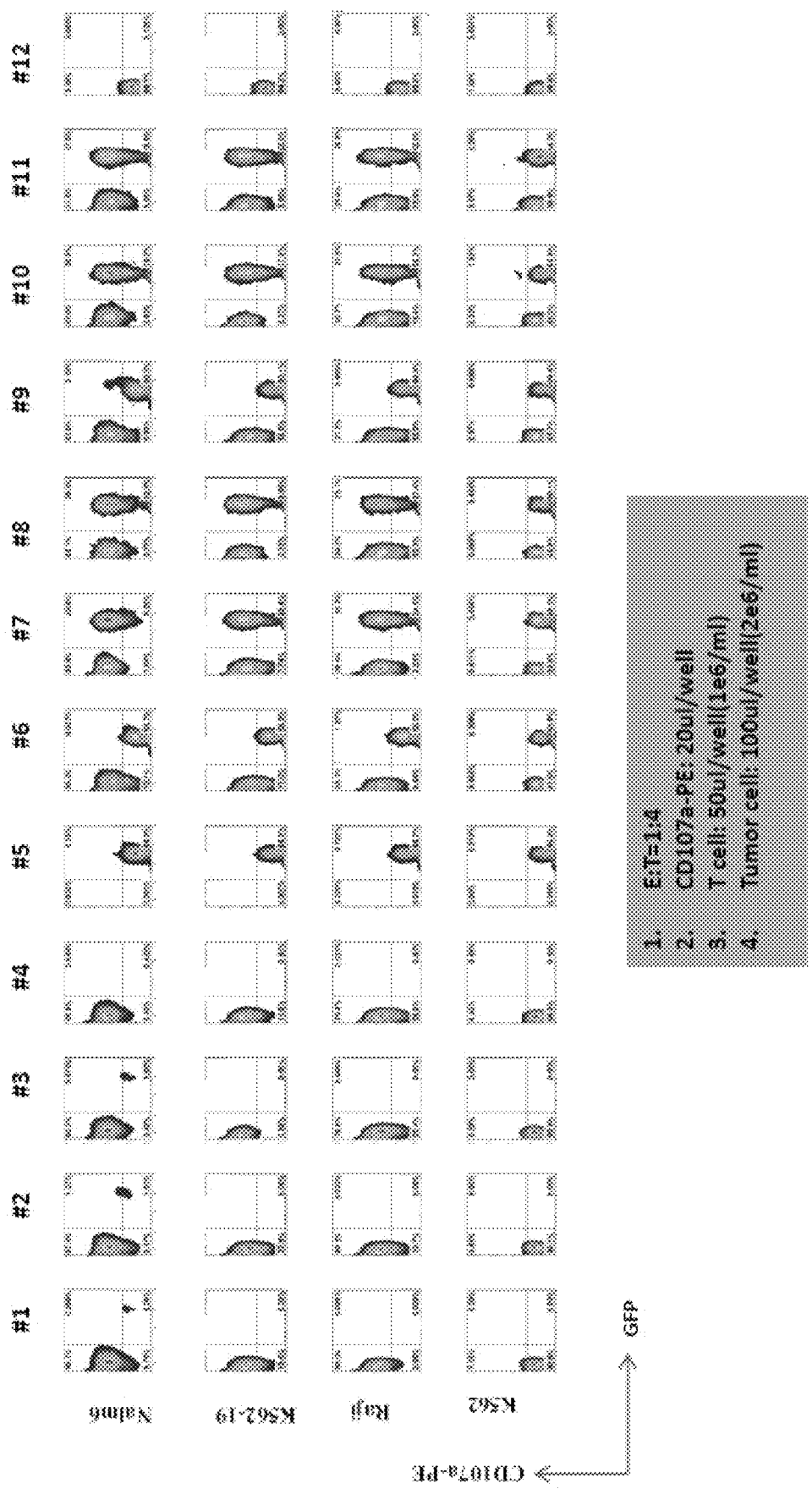
FIG. 5 is a series of graphs depicting the results of experiments demonstrating that T cells electroporated with Blina "BITE" bispecific anti-CD19/CD3 RNA could enable non-tumor reactive, GFP RNA electroporated T cells to specifically recognize tumors. Fifteen hours after electroporation, the T cells for all the conditions shown in FIG. 2 were co-cultured with different cells that express CD19 (Nalm6, K562-CD19 and Raji) or the CD19 negative tumor K562 for CD107a degranulation assay. The number shown above each plot are the conditions listed in FIG. 2. The results show that T cells electroporated with Blina bis-RNA specifically recognized tumors. The results show that T cells electroporated with Blina bis-RNA could enable non-tumor reactive, GFP RNA electroporated "bystander" T cells to specifically recognize tumors (#7, #8, #10, #11). CD8+ T cells were gated.

Furthermore, when mixing T cells co-electroporated with both CD19 CAR RNA and Blina RNA or Blina RNA alone with T cells electroporated with only GFP, it was found that bispecific Ab secreted from Blina RNA electroporated T cells could arm non-tumor recognizing GFP+ T cells to efficiently recognize CD19+ tumors (FIG. 5).

Figure 6:
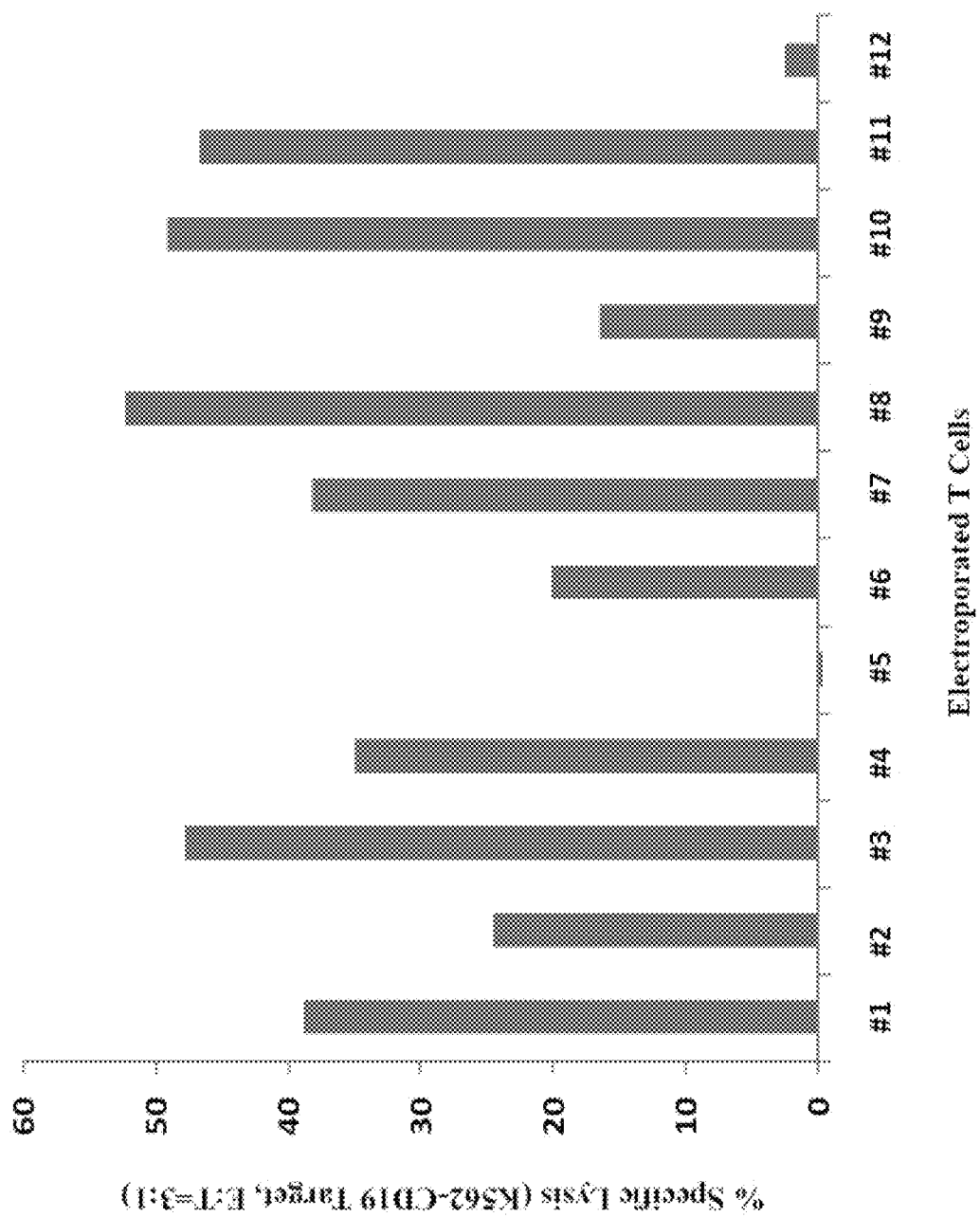
FIG. 6 is a graph depicting the results of experiments illustrating that T cells electroporated with Blina bis-RNA specifically kill CD19 antigen expressing cells. Fifteen hours after electroporation, the T cells for all the conditions shown in FIG. 2 were tested for their lytic activity in a flow based CTL assay using K562-CD19-CFSE/K562-meso-CMRA as target cells. The number shown for each condition of electroporated T cells are the numbers listed in FIG. 2. The results show that co-electroporation of Blina bispecific anti-CD19/anti-CD3 RNA with CD19 CAR RNA could further enhance the killing activity of the T cells (#3 versus #2). Adding an equal number of non-tumor reactive, GFP electroporated T cells to CD19 CAR RNA electroporated T cells reduced the killing ability of CD19 CAR expressing T cells by reducing E:T ratio, while adding an equal number of non-tumor reactive, GFP electroporated T cells to Blina bis-RNA electroporated T Cells (#7, #8, #10, #11) could maintain T cell killing activity equivalent to their non-diluted groups (#3 and #4), indicating that anti-CD19/anti-CD3 bispecific Ab secreted by Blina bis-RNA electroporated T cells could bind to GFP RNA electroporated T cells and efficiently kill the target cells, thus effectively maintaining the E:T ratio.

Electroporated cells were examined for their lytic activity in a flow-based CTL assay using K562-CD19-CFSE/K562-meso-CMRA as target cells. Co-electroporation of Blina RNA with CD19 CAR RNA could further enhance killing activity of the T-cells (FIG. 6). Further, co-incubation of Blina RNA electroporated cells with non-tumor recognizing GFP+ cells maintained killing activity compared to the non-diluted counterparts, demonstrating that secreted bis-RNA could bind to GFP-RNA electroporated T cells to efficiently kill CD19+ tumors, in an antigen specific way (FIG. 6).

Figure 7:
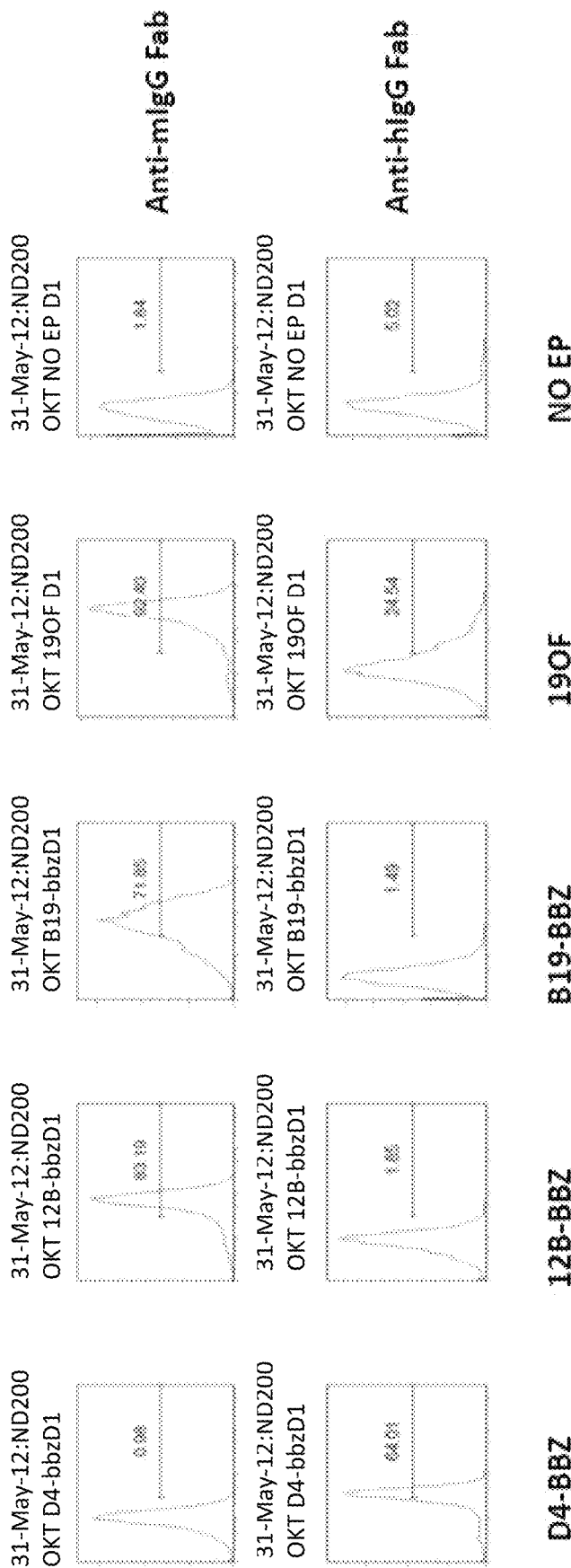
FIG. 7 is a series of graphs depicting the staining of CAR expression of new CD19 CAR RNA electroporated RNAs. The expression of the newly constructed CD19 CARs is shown fifteen hours after electroporation of T cells as indicated. Two different anti-IgG Fab were used: Anti-mIgG Fab was used to stain mouse derived CAR, and anti-hIgG Fab was used to stain human derived CARs.
Figure 8:
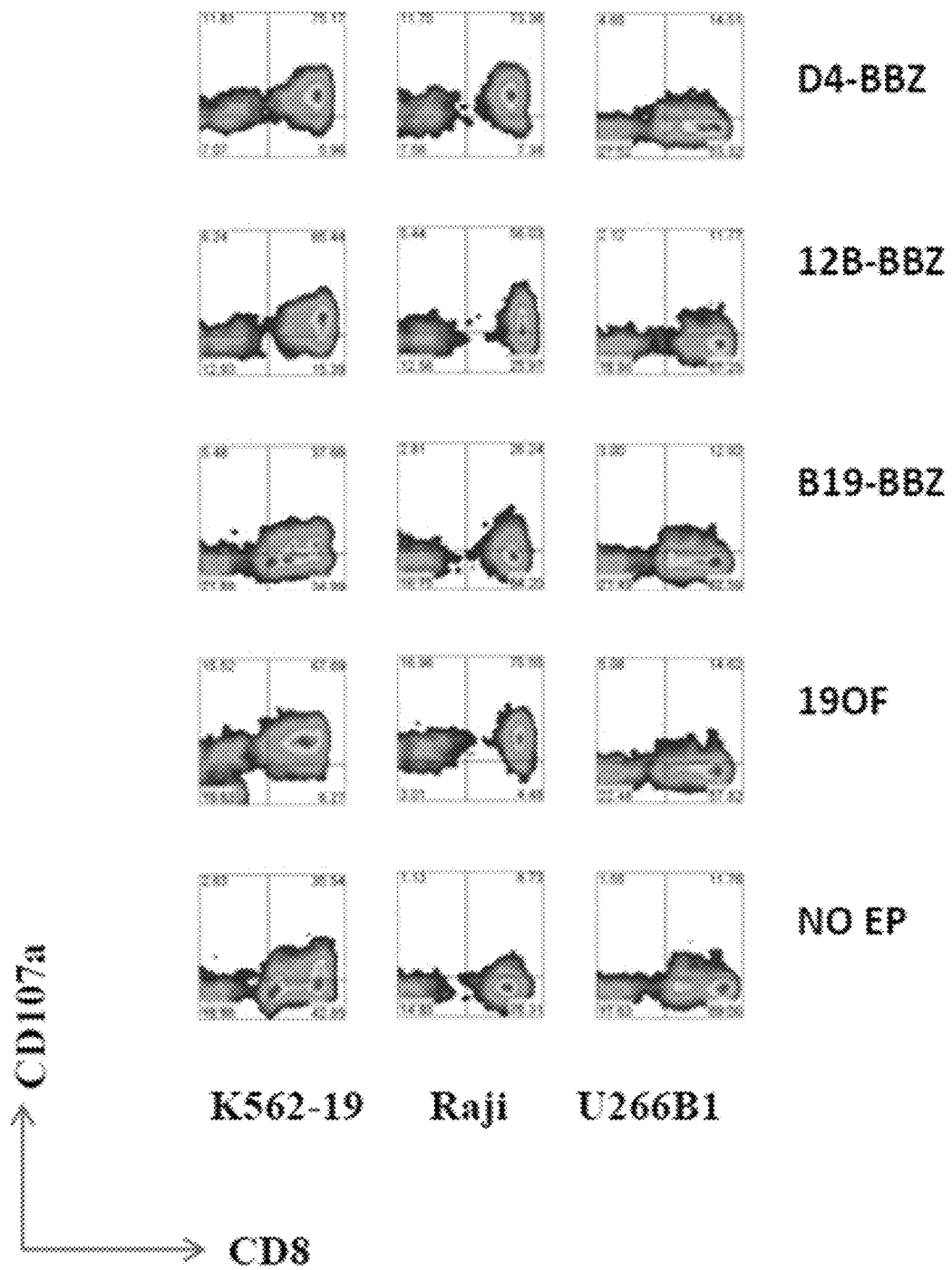
FIG. 8 is a series of graphs depicting the results of experiments illustrating that both CD19 CARs from fully human Ab 12D4 and humanized HB12B specifically recognize CD19 positive tumors. Fifteen hours after electroporation, the electroporated T cells as indicated were co-cultured with two CD19 positive tumor lines (K562-CD19 or Raji) and one CD19 negative line U266B1 for a CD107a degranulation assay. Compared with currently used FMC63 CD19 CAR (10OF), both CD19 CARs from fully human Ab 12D4 and humanized HB12B specifically recognized CD19 positive tumors.

The new CD19 CAR RNA constructs were evaluated by examining their expression 15 hours post electroporation by staining for either mouse IgG or human IgG, which showed that all constructs induced CAR expression (FIG. 7). When co-cultured with CD19+ tumor lines (K562-CD19 or Raji) or with a CD negative line (U266B1), T cells electroporated with the new constructs displayed ability to specifically recognize CD19 positive tumors, as evidenced by the CD107a assay (FIG. 8).

Figure 9A:
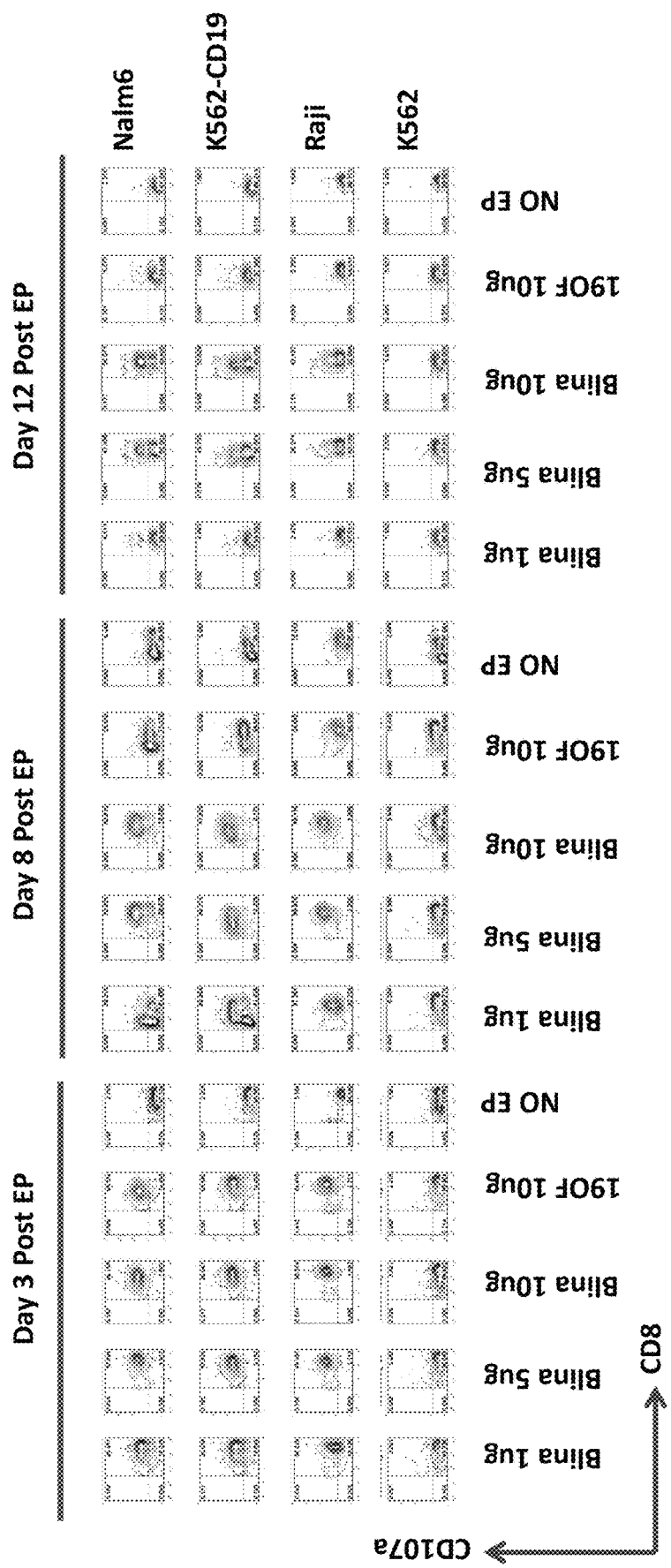
FIG. 9A and FIG. 9B, are a series of graphs depicting the results of experiments illustrating that T cells electroporated with Blina Bis-RNA alone were more sensitive and displayed longer persistence of anti-tumor activity than T cells electroporated with CD19 CAR RNA. T cells electroporated with Blina Bis-RNA at 1 µg, 5 µg or 10 µg were compared with the T cells electroporated with CD19BBZ (19OF) RNA at 10 µg. On multiple days post electroporation, CD107a assay was conducted after those T cells were stimulated with CD19+ cell lines (Naln6, K562-CD19 or Raji), or with CD19 negative cell line K562 as control.
Figure 9B:
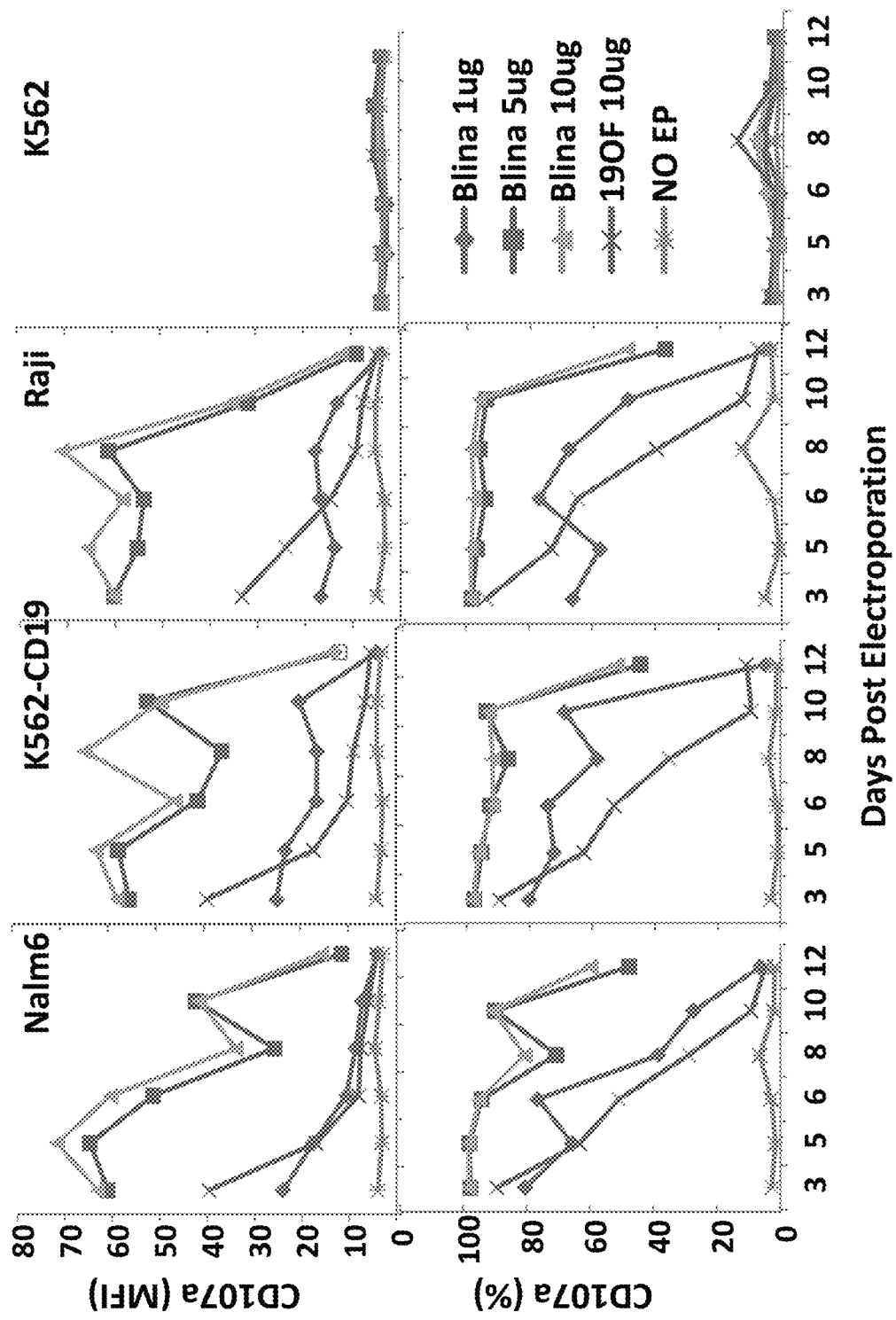

T cells were electroporated with Blina Bis-RNA at 1 μg, 5 μg or 10 μg and were compared with the T cells electroporated with FCM63 CD19 CAR RNA at 10 μg. A CD107a assay was performed after, electroporated cells were stimulated with CD19+ cells (Naln6, K562-CD19, or Raji), or with CD19− cell line (K562). It was found that T cells with 1 μg Blina Bis-RNA functioned nearly as well as T cells with 10 μg CD19 CAR RNA. T cells with 10 μg CD19 CAR RNA lost their function at day 8-10 after electroporation, which is similar as the T cells with 1 μg Blina Bis-RNA, while the T cells with 5 μg or 10 μg Blina Bis-RNA continued to function up to day 14 post electroporation (FIG. 9B).

Figure 10:
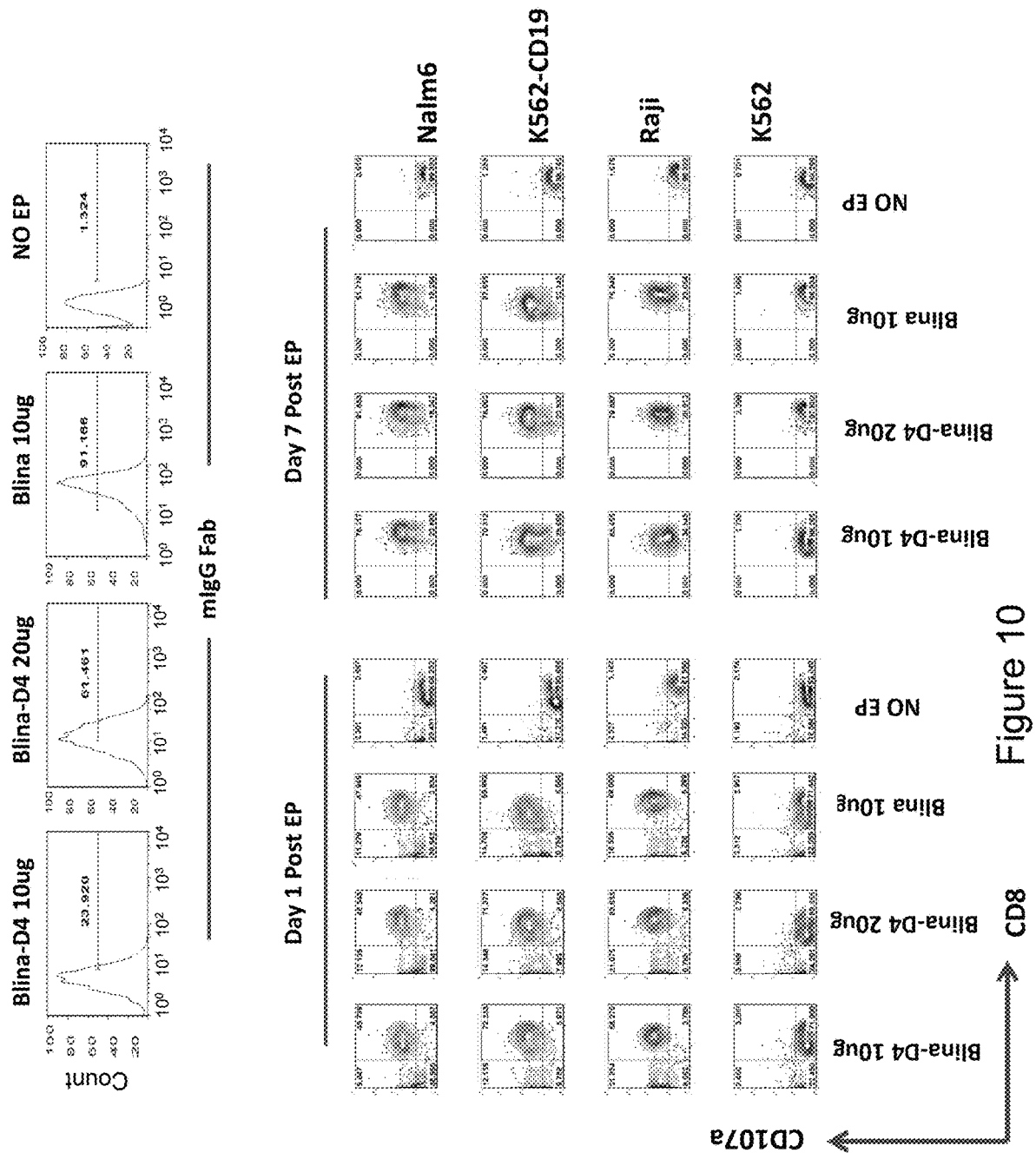
FIG. 10 is a series of graphs depicting the results of experiments illustrating that T cells electroporated with a Bis-RNA containing human CD19 scFv (Blina-D4) function equally as well as T cells with Blina Bis-RNA. T cells electroporated with Blina-D4 Bis-RNA at 10 µg or 20 µg, or with 10 µg Blina Bis-RNA and subjected to CAR staining (Anti-mouse IgG Fab), upper panel (day 1 post electroporation) and Cd107a staining (lower panel).

To assess the functionality of human and humanized forms of Bis-RNA, T cells were electroporated with Blina-D4 Bis-RNA, in which CD19 scFv from Blina was replaced with 21D4 scFv. Cells were subjected to CAR staining and CD107a staining, which demonstrated that cells electroporated with Blina-D4 functioned equally well as T cells with Blina Bis-RNA (FIG. 10).

Figure 11A:
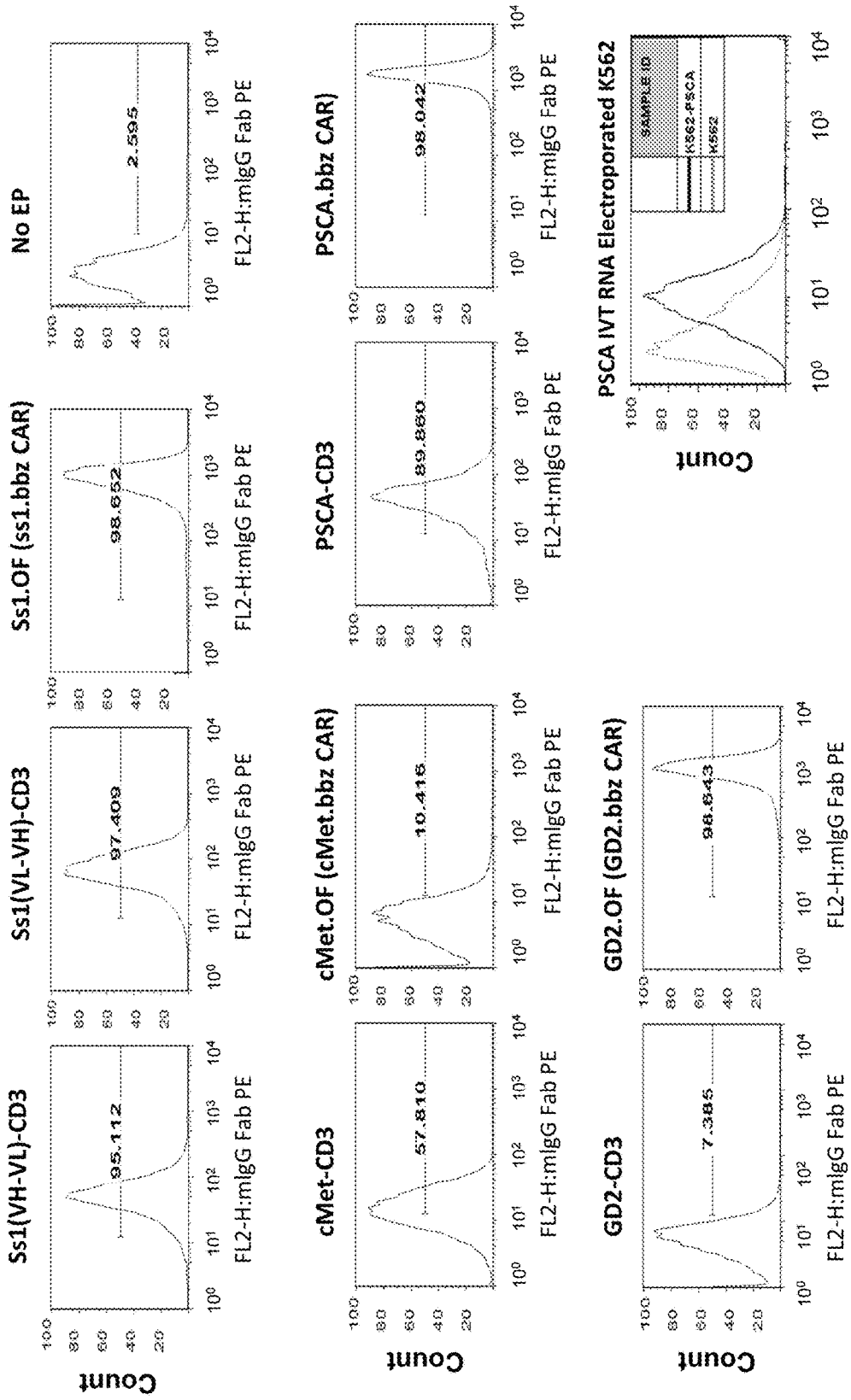
FIG. 11A and FIG. 11B, are a series of graphs depicting the results of experiments illustrating that T cells electroporated with Bis-RNAs against mesothelin, cMet or PSCA functioned equally as well as T cells electroporated with CAR RNA. T cells electroporated with 10 µg Bis-RNA of ss1HL-Blina, or ss1LH-Blina, or cMet-Blina, or PSCA-Blina or GD2-Blina, were compared to T cells electroporated with 10 µg ss1BBZ (ss1.OF), or cMetBBZ, or PSCA.BBZ or GD2.BBZ CAR RNA.
Figure 11B:
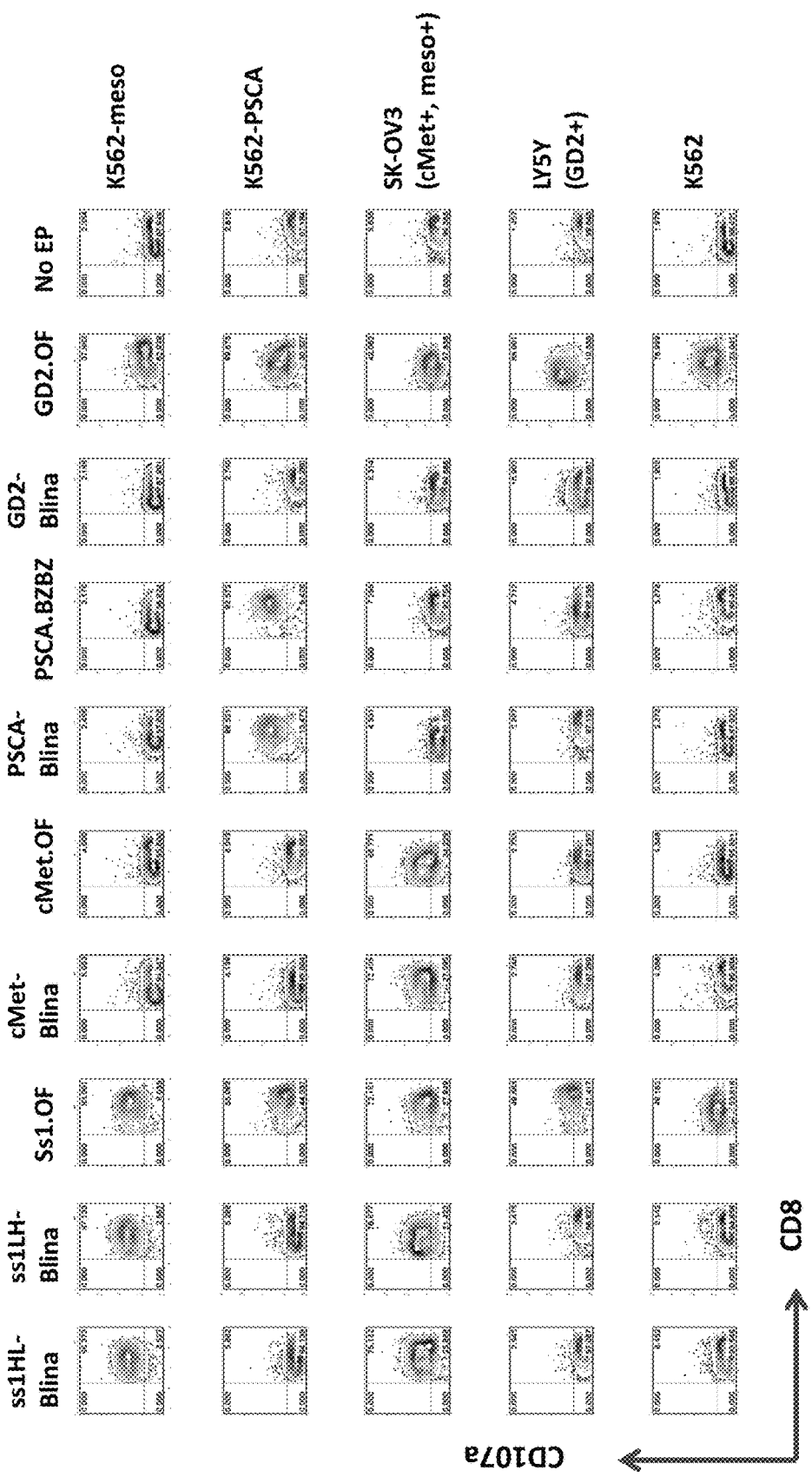

Bis-RNA constructs specific for other antigen markers were designed and constructed. Comparing with T cells expressing CAR RNA for mesothelin (ss1), cMet or PSCA, it was found that the T cells expressing ss1-Blina, cMet-Blina, or PSCA-Blina Bis-RNA alone could function equally as well as T cells with CAR RNA. Moreover, T cells with ss1-Blina Bis-RNAs showed more antigen specific T cell activation than T cells with ss1 CAR RNA (FIG. 11).

The results presented herein demonstrate that introducing bispecific antibody RNA along with CD19 CARs enhances the anti-tumor activity of CAR engineered T cells. Further, introduction of bispecific antibody RNA into T cells recruits non-tumor reactive T cells to become tumor reactive, which provides a novel way of delivering and trafficking an anti-tumor drug into cancer patients by using T cells. This could reduce the toxicity of systemic BiTEs, by focusing the delivery of the bispecific antibody to the tumor microenvironment by virtue of the CAR T cell that will carry the cargo (BiTE) to the site of the tumor.

```
Blinatumomab ORF (SEQ ID NO: 1)
atgggatggagctgtatcatcctcttcttggtagcaacagctacaggtgtccactccgactacaaagatgatgacgataagg atatccagctgacccagtctccagcttctttggctgtgtctctagggcagagggccaccatctcctgcaaggccagccaaag tgttgattatgatggtgatagttatttgaactggtaccaacagattccaggacagccacccaaactcctcatctatgatgcatcc aatctagtttctgggatcccacccaggtttagtggcagtgggtctgggacagacttcaccctcaacatccatcctgtggagaa ggtggatgctgcaacctatcactgtcagcaaagtactgaggatccgtggacgttcggtggagggaccaagctcgagatca aaggtggtggtggttctggcggcggcggctccggtggtggtggttctcaggtgcagctgcagcagtctggggctgagctg gtgaggcctgggtcctcagtgaagatttcctgcaaggcttctggctatgcattcagtagctactggatgaactgggtgaagc agaggcctggacagggtcttgagtggattggacagatttggcctggagatggtgatactaactacaatggaaagttcaagg gtaaagccactctgactgcagacgaatcctccagcacagcctacatgcaactcagcagcctagcatctgaggactctgcg gtctatttctgtgcaagacgggagactacgacggtaggccgttattactatgctatggactactggggccaagggaccacg gtcaccgtctcctccggaggtggtggatccgatatcaaactgcagcagtcaggggctgaactggcaagacctggggcctc agtgaagatgtcctgcaagacttctggctacacctnactaggtacacgatgcactgggtaaaacagaggcctggacaggg tctggaatggattggatacattaatcctagccgtggttatactaattacaatcagaagttcaaggacaaggccacattgactac agacaaatcctccagcacagcctacatgcaactgagcagcctgacatctgaggactctgcagtctattactgtgcaagatatt atgatgatcattactgccttgactactggggccaaggcaccactctcacagtctcctcagtcgaaggtggaagtggaggttct ggtggaagtggaggttcaggtggagtcgacgacgccgccattcagctgacccagtctccagcaatcatgtctgcatctcca ggggagaaggtcaccatgacctgcagagccagttcaagtgtaagttacatgaactggtaccagcagaagtcaggcacctc ccccaaaagatggatttatgacacatccaaagtggcttctggagtcccttatcgcttcagtggcagtgggtctgggacctcat actctctcacaatcagcagcatggaggctgaagatgctgccacttattactgccaacagtggagtagtaacccgctcacgtt cggtgctgggaccaagctggagctgaaacatcatcaccatcatcattaataa Blina-D4 (SEQ ID NO: 2)
atgggctggtcttgcatcatcctgttcctcgtggccaccgccaccggcgtccacagcgccatccagctcacccagagcccc tcgagcttgagtgcctcggtgggagaccgggtcactatcacctgccgagccagtcagggcatctcctccgcccttgcctgg taccagcagaagcccgggaaggcccccaagctgctgatctacgacgctagtagtctggagagtggcgtgccttcgcgctt ctcgggcagtgggagtggcaccgacttcaccttgaccatctccagtctacagccggaagatttcgcgacctactactgtcag caattcaactcttatccatacactttcggccaggggacaaagctggagatcaagggcggggcgggagtggcggcggag ggtccggaggcgggggctccgaggtgcaactagtccagagcggagccgaggtgaagaagcccggggagagtctaaa gatctcttgcaagggctccggttactccttctcgagttcctggatcgggtgggtgcgacagatgccgggcaagggcctgga gtggatgggcattatctaccccgacgactccgatacccgttatagtccatcgttccagggacaggtgaccatttccgccgac aagtctatcagaaccgcctatctgcagtggtccagtctgaaggcctctgacactgccatgtattattgcgccaggcacgttac gatgatctgggggtgatcatcgacttctggggccagggcacactcgtaaccgtcagttctggaggtggtggatccgatat caaactgcagcagtcaggggctgaactggcaagacctggggcctcagtgaagatgtcctgcaagacttctggctacacctt tactaggtacacgatgcactgggtaaaacagaggcctggacagggtctggaatggattggatacattaatcctagccgtgg ttatactaattacaatcagaagttcaaggacaaggccacattgactacagacaaatcctccagcacagcctacatgcaactg agcagcctgacatctgaggactctgcagtctattactgtgcaagatattatgatgatcattactgccttgactactggggccaa ggcaccactctcacagtctcctcagtcgaaggtggaagtggaggttctggtggaagtggaggttcaggtggagtcgacga
```

-continued cgccgccattcagctgacccagtctccagcaatcatgtctgcatctccaggggagaaggtcaccatgacctgcagagcca gttcaagtgtaagttacatgaactggtaccagcagaagtcaggcacctcccccaaaagatggatttatgacacatccaaagt ggcttctggagtcccttatcgcttcagtggcagtgggtctgggacctcatactctctcacaatcagcagcatggaggctgaa gatgctgccacttattactgccaacagtggagtagtaacccgctcacgttcggtgctgggaccaagctggagctgaaacat catcaccatcatcattaa Ss1.HL.CD3 (SEQ ID NO: 3)
atggccttaccagtgaccgccttgctcctgccgctggccttgctgctccacgccgccaggccgggatcccaggtacaactg cagcagtctgggcctgagctggagaagcctggcgcttcagtgaagatatcctgcaaggcttctggttactcattcactggct acaccatgaactgggtgaagcagagccatggaaagagccttgagtggattggacttattactccttacaatggtgcttctagc tacaaccagaagttcaggggcaaggccacattaactgtagacaagtcatccagcacagcctacatggacctcctcagtctg acatctgaagactctgcagtctatttctgtgcaagggggggttacgacgggaggggttttgactactggggccaagggacc acggtcaccgtctcctcaggtggaggcggttcaggcggcggtggctctagcggtggcggatcggacatcgagctcactc agtctccagcaatcatgtctgcatctccaggggagaaggtcaccatgacctgcagtgccagctcaagtgtaagttacatgca ctggtaccagcagaagtcaggcacctcccccaaaagatggatttacgacacatccaaactggcttctggagtcccaggtcg cttcagtggcagtgggtctggaaactcttactctctcacaatcagcagcgtggaggctgaagacgacgcaacttattactgc cagcagtggagtaagcaccctctcacgtacggtgctgggacaaagttggaaatcaaaggaggtggtggatccgatatcaa actgcagcagtcaggggctgaactggcaagacctggggcctcagtgaagatgtcctgcaagacttctggctacacctttac taggtacacgatgcactgggtaaaacagaggcctggacagggtctggaatggattggatacattaatcctagccgtggttat actaattacaatcagaagttcaaggacaaggccacattgactacagacaaatcctccagcacagcctacatgcaactgagc agcctgacatctgaggactctgcagtctattactgtgcaagatattatgatgatcattactgccttgactactggggccaaggc accactctcacagtctcctcagtcgaaggtggaagtggaggttctggtggaagtggaggttcaggtggagtcgacgacgc cgccattcagctgacccagtctccagcaatcatgtctgcatctccaggggagaaggtcaccatgacctgcagagccagttc aagtgtaagttacatgaactggtaccagcagaagtcaggcacctcccccaaaagatggatttatgacacatccaaagtggct tctggagtcccttatcgcttcagtggcagtgggtctgggacctcatactctctcacaatcagcagcatggaggctgaagatg ctgccacttattactgccaacagtggagtagtaacccgctcacgttcggtgctgggaccaagctggagctgaaacatcatca ccatcatcattaataa Ss1.LH.CD3 (SEQ ID NO: 4)
Atggccttaccagtgaccgccttgctcctgccgctggccttgctgctccacgccgccaggccgggatccgacatcgagct cactcagtctccagcaatcatgtctgcatctccaggggagaaggtcaccatgacctgcagtgccagctcaagtgtaagttac atgcactggtaccagcagaagtcaggcacctcccccaaaagatggatttacgacacatccaaactggcttctggagtccca ggtcgcttcagtggcagtgggtctggaaactcttactctctcacaatcagcagcgtggaggctgaagacgacgcaacttatt actgccagcagtggagtaagcaccctctcacgtacggtgctgggacaaagttggaaatcaaaggtggtggtggttctggc ggcggcggctccggtggtggtggttctcaggtacaactgcagcagtctgggcctgagctggagaagcctggcgcttcagt gaagatatcctgcaaggcttctggttactcattcactggctacaccatgaactgggtgaagcagagccatggaaagagcctt gagtggattggacttattactccttacaatggtgcttctagctacaaccagaagttcaggggcaaggccacattaactgtaga caagtcatccagcacagcctacatggacctcctcagtctgacatctgaagactctgcagtctatttctgtgcaaggggggtt acgacgggaggggttttgactactggggccaagggaccacggtcaccgtctcctcaggaggtggtggatccgatatcaaa ctgcagcagtcaggggctgaactggcaagacctggggcctcagtgaagatgtcctgcaagacttctggctacacctttact aggtacacgatgcactgggtaaaacagaggcctggacagggtctggaatggattggatacattaatcctagccgtggttat actaattacaatcagaagttcaaggacaaggccacattgactacagacaaatcctccagcacagcctacatgcaactgagc agcctgacatctgaggactctgcagtctattactgtgcaagatattatgatgatcattactgccttgactactggggccaaggc accactctcacagtctcctcagtcgaaggtggaagtggaggttctggtggaagtggaggttcaggtggagtcgacgacgc -continued cgccattcagctgacccagtctccagcaatcatgtctgcatctccaggggagaaggtcaccatgacctgcagagccagttc aagtgtaagttacatgaactggtaccagcagaagtcaggcacctcccccaaaagatggatttatgacacatccaaagtggct tctggagtcccttatcgcttcagtggcagtgggtctgggacctcatactctctcacaatcagcagcatggaggctgaagatg ctgccacttattactgccaacagtggagtagtaacccgctcacgttcggtgctgggaccaagctggagctgaaacatcatca ccatcatcattaataa cMet.CD3 (SEQ ID NO: 5)
atgctgctgctggtgaccagcctgctgctgtgtgagctgccccaccccgcctactgctgatcccgacatccagatgaccc agagccccagcagcgtgagcgccagcgtgggcgaccgggtgaccatcacctgccgggccagccagggcatcaacac ctggctggcctggtatcagcagaagcccggcaaggcccccaagctgctgatcctacgcgccagcagcctgaagagcgg cgtgcccagccggtttagcggctctggctctggcgccgacttcaccctgaccatcagcagcctgcagcccgaggacttcg ccacctactactgccagcaggccaacagcttcccccctgacctttggcggcggaacaaaggtggagatcaagggcagcac ctccggcagcggcaagcctggcagcggcgagggcagcaccaagggccaggtgcagctggtgcagagcggagccga ggtgaagaagcctggcgcctccgtcaaggtgtcctgcgaggccagcggctacaccttccagctacggcttcagctgg gtgcggcaggcaccaggccaggcctcgaatggatgggctggatcagcgccagcaacggcaacacctactacgccca gaagctgcagggcagggtcaccatgaccaccgacaccagcaccagcagcgcctacatggaactgcgcgagcctgagaa gcgacgacaccgccgtgtactactgcgccagggtgtacgccgactacgccgattactggggccagggcaccctggtgac cgtgagcagcggaggtggtggatccgatatcaaactgcagcagtcaggggctgaactggcaagacctggggcctcagtg aagatgtcctgcaagacttctggctacacctttactaggtacacgatgcactgggtaaaacagaggcctggacagggtctg gaatggattggatacattaatcctagccgtggttatactaattacaatcagaagttcaaggacaaggccacattgactacaga caaatcctccagcacagcctacatgcaactgagcagcctgacatctgaggactctgcagtctattactgtgcaagatattatg atgatcattactgccttgactactggggccaaggcaccactctcacagtctcctcagtcgaaggtggaagtggaggttctgg tggaagtggaggttcaggtggagtcgacgacgccgccattcagctgacccagtctccagcaatcatgtctgcatctccagg ggagaaggtcaccatgacctgcagagccagttcaagtgtaagttacatgaactggtaccagcagaagtcaggcacctccc ccaaaagatggatttatgacacatccaaagtggcttctggagtcccttatcgcttcagtggcagtgggtctgggacctcatac tctctcacaatcagcagcatggaggctgaagatgctgccacttattactgccaacagtggagtagtaacccgctcacgttcg gtgctgggaccaagctggagctgaaacatcatcaccatcatcattaataa PSCA.CD3 (SEQ ID NO: 6)
atggcgctaccggtgaccgcactcctgctgccactcgccctcctgctccacgccgcccgccccgatatccagctgacccca tcaccgtcgtccctgtctgcctccgtgggcgaccgggtgacgatcacctgtagtgcctcgagcagtgtacggttcatccac tggtaccaacagaagcccggcaaggcaccaaagcggctgatctacgacaccagcaagctggcgtctggggtcccagc aggttctcgggaagtggtagtggcacagacttcactctcaccatcagttcactccagccggaggactttgccacctactattg ccagcagtggtcctcgtccccctttaccttcggcagggaacaaaggtggaaattaagggttcgacctccggggggggct ccggtgggggctccggcggggggggctcatcggaggttcagctggtggagagcggcggcggcctggtgcagcccgg cgggagtctgcggctgtcctgtgccgccagcggcttcaacatcaaggactactacattcactgggtgcggcaagccccag gcaagggtctgagtgggtggcttggattgaccctgaaaacggcgacactgagttcgtgccaaaattccaggggcggc gaccatctccgccgacacctccaagaatacggcctacctgcagatgaactccctgcgcgccgaagacacagcggtctact actgcaagacagggggtttctggggccagggcaccctcgtgaccgtttcgagtgccgccggcggaggtggtggatccga tatcaaactgcagcagtcaggggctgaactggcaagacctggggcctcagtgaagatgtcctgcaagacttctggctacac ctttactaggtacacgatgcactgggtaaaacagaggcctggacagggtctggaatggattggatacattaatcctagccgt ggttatactaattacaatcagaagttcaaggacaaggccacattgactacagacaaatcctccagcacagcctacatgcaac tgagcagcctgacatctgaggactctgcagtctattactgtgcaagatattatgatgatcattactgccttgactactggggcc aaggcaccactctcacagtctcctcagtcgaaggtggaagtggaggttctggtggaagtggaggttcaggtggagtcgac gacgccgccattcagctgacccagtctccagcaatcatgtctgcatctccaggggagaaggtcaccatgacctgcagagc cagttcaagtgtaagttacatgaactggtaccagcagaagtcaggcacctcccccaaaagatggatttatgacacatccaaa gtggcttctggagtcccttatcgcttcagtggcagtgggtctgggacctcatactctctcacaatcagcagcatggaggctga agatgctgccacttattactgccaacagtggagtagtaacccgctcacgttcggtgctgggaccaagctggagctgaaaca tcatcaccatcatcattaataa GD2-CD3 (SEQ ID NO: 7)
atggagtttgggctgagctggcttttttcttgtggctattttaaaaggtgtccagtgctctagagatattttgctgacccaaactcc actctccctgcctgtcagtcttggagatcaagcctccatctcttgcagatctagtcagagtcttgtacaccgtaatggaaacac ctatttacattggtacctgcagaagccaggccagtctccaaagctcctgattcacaaagtttccaaccgattttctggggtccc agacaggttcagtggcagtggatcagggacagatttcacactcaagatcagcagagtggaggctgaggatctgggagttt atttctgttctcaaagtacacatgttcctccgctcacgttcggtgctgggaccaagctggagctgaaacgggctgatgctgca ccaactgtatccatcttcccaggctcgggcggtggtgggtcgggtggcgaggtgaagcttcagcagtctggacctagcctg gtggagcctggcgcttcagtgatgatatcctgcaaggcttctggttcctcattcactggctacaacatgaactgggtgaggca gaacattggaaagagccttgaatggattggagctattgatccttactatggtggaactagctacaaccagaagttcaagggc agggccacattgactgtagacaaatcgtccagcacagcctacatgcacctcaagagcctgacatctgaggactctgcagtc tattactgtgtaagcggaatggagtactggggtcaaggaacctcagtcaccgtctcctcagccaaaacgacacccccatca gtctatggaggtggtggatccgatatcaaactgcagcagtcaggggctgaactggcaagacctggggcctcagtgaagat gtcctgcaagacttctggctacacctttactaggtacacgatgcactgggtaaaacagaggcctggacagggtctggaatg gattggatacattaatcctagccgtggttatactaattacaatcagaagttcaaggacaaggccacattgactacagacaaat cctccagcacagcctacatgcaactgagcagcctgacatctgaggactctgcagtctattactgtgcaagatattatgatgat cattactgccttgactactggggccaaggcaccactctcacagtctcctcagtcgaaggtggaagtggaggttctggtggaa gtggaggttcaggtggagtcgacgacgccgccattcagctgacccagtctccagcaatcatgtctgcatctccaggggag aaggtcaccatgacctgcagagccagttcaagtgtaagttacatgaactggtaccagcagaagtcaggcacctcccccaa aagatggatttatgacacatccaaagtggcttctggagtcccttatcgcttcagtggcagtgggtctgggacctcatactctct cacaatcagcagcatggaggctgaagatgctgccacttattactgccaacagtggagtagtaacccgctcacgttcggtgct gggaccaagctggagctgaaacatcatcaccatcatcattaataa D4-27H5 VL1 (D4-VL1) (SEQ ID NO: 8)
Atgggctggtcttgcatcatcctgttcctcgtggccaccgccaccggcgtccacagcgccatccagctcacccagagccc ctcgagcttgagtgcctcggtgggagaccgggtcactatcacctgccgagccagtcagggcatctcctccgcccttgcctg gtaccagcagaagcccggaaggcccccaagctgctgatctacgacgctagtagtctggagagtggcgtgccttcgcgc ttctcgggcagtgggagtggcaccgacttcaccttgaccatctccagtctacagccggaagatttcgcgacctactactgtc agcaattcaactcttatccatacttttcggccaggggacaaagctggagatcaagggcggggcgggagtggcggcgg agggtccggaggcggggctccgaggtgcaactagtccagagcggagccgaggtgaagaagcccggggagagtccta aagatctcttgcaagggctccggttactccttctcgagttcctggatcgggtgggtgcgacagatgccgggcaagggcctg gagtggatgggcattatctaccccgacgactccgatacccgttatagtccatcgttccagggacaggtgaccatttccgccg acaagtctatcagaaccgcctatctgcagtggtccagtctgaaggcctctgacactgccatgtattattgcgccaggcacgtt acgatgatctgggggtgatcatcgacttctggggccagggcacactcgtaaccgtcagttcggaggtggtggatcccag GTG cag ctc gtg gag TCC ggc GGC ggc GTT GTC cag CCT GGC cgc TCG ctg cgc ctg tca tgc GCC GCT TCG ggt ttc ACG ttc agg TCG TAC GGG atg cac tgg GTC AGG cag GCG CCG gga AAA GGC CTG gag tgg GTG GCT atc ATC tgg TAC GAC ggc TCC aag aag AAT TAT GCT gac TCC GTC aag gga CGG ttc ACA atc tcg CGT GAT aac tcg aag aac acc CTC TAC CTG cag atg AAT TCC CTC AGA GCC

```
GAA gac ACA GCC gtg TAT TAT tgc GCC AGG ggc ACC ggc tat aac tgg TTC

GAT CCA tgg ggc cag GGG ACC ctg GTT acc GTC tcc tcc GGA GGG GGG GGT agt gag atc gtg ctg acc cag tcg CCT CGC ACC CTG tcc CTG tcc CCT GGG gag CGC gcc ACC CTC tcg tgc AGG GCA tcg cag TCC gtc agt TCC TCC TAT ctg GCC tgg tac CAG cag aaa CCT ggc cag GCA cca AGG CTG ctg ATC tac GGA GCT tcc TCG AGG GCA ACC GGG ATC CCC gac AGA TTT tcc GGA agc GGA AGT GGC ACA gac ttc ACC ctg acc ATC AGT AGG CTT GAC CCC gaa GAT ttc GCC GTG tac TAT tgc cag cag tac GGC TCC TCC ccc atc acc ttc ggc cag GGC ACA AGA ctg gag atc aag cac CAT cac cac cac cac TAA TAA gcggccgc
```

D4-27H5 VL2 (D4-VL2) (SEQ ID NO: 9)
```
Atgggctggtcttgcatcatcctgttcctcgtggccaccgccaccggcgtccacagcgccatccagctcacccagagccc ctcgagcttgagtgcctcggtgggagaccgggtcactatcacctgccgagccagtcagggcatctcctccgcccttgcctg gtaccagcagaagcccggaaggccccccaagctgctgatctacgacgctagtagtctggagagtggcgtgccttcgcgc ttctcgggcagtgggagtggcaccgacttcaccttgaccatctccagtctacagccggaagatttcgcgacctactactgtc agcaattcaactcttatccatacactttcggccaggggacaaagctggagatcaagggcggggcgggagtggcggcgg agggtccggaggcgggggctccgaggtgcaactagtccagagcggagccgaggtgaagaagcccggggagagtcta aagatctcttgcaagggctccggttactccttctcgagttcctggatcgggtgggtgcgacagatgccgggcaagggcctg gagtggatgggcattatctaccccgacgactccgatacccgttatagtccatcgttccagggacaggtgaccatttccgccg acaagtctatcagaaccgcctatctgcagtggtccagtctgaaggcctctgacactgccatgtattattgcgccaggcacgtt acgatgatctgggggggtgatcatcgacttctggggccagggcacactcgtaaccgtcagttcggaggtggtggatccCA
```

```
G GTA CAG ctg GTC GAG tcc GGT ggg GGC gtg GTC cag CCC ggc CGG tcc

CTG CGC CTG TCG tgc GCT GCC TCC ggc TTT ACC ttc CGG TCG TAT GGC atg CAT tgg gtg cgc cag GCC CCC GGG aag ggg ctg gag tgg GTC gcc ATT ATC tgg tac gat GGC TCC AAG aag aac TAC gct GAT TCG GTT aag ggc cgc TTC ACC att AGT CGG GAT aat TCG aag aat ACG CTG TAT CTC CAG atg aac TCC ctg AGG GCC GAG gac act gcc GTG TAC TAC tgc gcc CGG GGC ACA GGC TAT aac tgg ttc gat ccc tgg GGT cag ggc ACC CTA gtg ACC GTC TCG TCT GGG GGC GGA ggg TCA GAT att ctc atg ACA cag TCG ccc TCT AGT CTT tcc GCC tcc gtg GGG GAC CGC GTG acc atc ACA tgc AGA GCT TCC CAG GGG atc tcc TCT GCG CTG gcc tgg TAT cag cag aag ccc GGG aag GCA CCC AAG ctg CTC ATC TAT TAC GCT tct TCG CTG CAA AGT GGG gtg ccg TCC CGC TTC tcc gga AGC ggc TCC ggc ACG GAC tac acc CTC acc atc tcc TCC CTG CAG CCT GAG GAT ttc GCC acc TAT tac tgc cag cag TAT tac TCC acg ctg ACC TTC GGA GGA GGC ACG AAA GTG gag atc aag CAC cac cac cac cac cac TAA TAA gcggccgc
```

D4-28F11 (D4-F11) (SEQ ID NO: 10)
```
Atgggctggtcttgcatcatcctgttcctcgtggccaccgccaccggcgtccacagcgccatccagctcacccagagccc ctcgagcttgagtgcctcggtgggagaccgggtcactatcacctgccgagccagtcagggcatctcctccgcccttgcctg gtaccagcagaagcccggaaggccccccaagctgctgatctacgacgctagtagtctggagagtggcgtgccttcgcgc ttctcgggcagtgggagtggcaccgacttcaccttgaccatctccagtctacagccggaagatttcgcgacctactactgtc agcaattcaactcttatccatacactttcggccaggggacaaagctggagatcaagggcggggcgggagtggcggcgg agggtccggaggcgggggctccgaggtgcaactagtccagagcggagccgaggtgaagaagcccggggagagtcta aagatctcttgcaagggctccggttactccttctcgagttcctggatcgggtgggtgcgacagatgccgggcaagggcctg
```

-continued gagtggatgggcattatctaccccgacgactccgatacccgttatagtccatcgttccagggacaggtgaccatttccgccg acaagtctatcagaaccgcctatctgcagtggtccagtctgaaggcctctgacactgccatgtattattgcgccaggcacgtt acgatgatctggggggtgatcatcgacttctggggccagggcacactcgtaaccgtcagttcggaggtggtggatcccag GTC cag ctg GTT gag TCT GGT GGC GGA gtg gtc cag CCC ggc CGG TCT CTC CGC ctg TCC tgc GCC GCT tcc GGG ttc AAG TTC TCC ggc TAC gga atg cac tgg gtg AGG cag GCG CCA GGT aag GGG CTC GAG tgg GTC GCG gtg ATA tgg TAT gac GGT AGC aag aag tat tac gtg gac AGT GTG AAA ggc CGC TTT acc atc TCA CGC GAC AAT TCT aag aac acc ctg TAC CTC CAG atg aac TCC ctg CGC gct gag GAC ACG GCG GTG TAC tac TGC GCT AGG cag atg GGG tac tgg cac TTC gac CTT tgg ggc AGG GGT acc CTG GTG acc gtc TCA TCC GGC ggc ggc GGG TCT gag ATC GTT CTG ACC CAA AGT CCG gcc ACA ctg tcc CTC TCC CCA GGA gag cgc GCT ACG CTT AGC tgc CGC gcc tcc cag AGC GTG TCC tcc tac ctg gca tgg TAT cag cag aag CCG GGG cag GCG CCT CGA ctg CTG atc tac gac gcc TCG aac CGC GCG ACA GGT atc ccc gcg CGC ttc AGC GGC TCC GGT TCG GGG ACT GAT ttc acc ctg ACC atc tcc TCC CTC GAG cct gag GAT ttc GCA gtg tac tac tgc cag cag aga TCC AAT tgg ccc CCC CTC acc ttc ggc GGG GGA acc aag GTG gag atc aag cac cac cac cac CAT cac TAATAA D4-DIVHv5 (D4-Hv5) (SEQ ID NO: 11)
Atgggctggtcttgcatcatcctgttcctcgtggccaccgccaccggcgtccacagcgccatccagctcacccagagccc ctcgagcttgagtgcctcggtgggagaccgggtcactatcacctgccgagccagtcagggcatctcctccgcccttgcctg gtaccagcagaagcccgggaaggccccccaagctgctgatctacgacgctagtagtctggagagtggcgtgccttcgcgc ttctcgggcagtgggagtggcaccgacttcaccttgaccatctccagtctacagccggaagatttcgcgacctactactgtc agcaattcaactcttatccatacactttcggccaggggacaaagctggagatcaagggcgggggcggggagtggcggcgg agggtccggaggcgggggctccgaggtgcaactagtccagagcggagccgaggtgaagaagcccggggagagtcta aagatctcttgcaagggctccggttactccttctcgagttcctggatcgggtgggtgcgacagatgccgggcaagggcctg gagtggatgggcattatctaccccgacgactccgatacccgttatagtccatcgttccagggacaggtgaccatttccgccg acaagtctatcagaaccgcctatctgcagtggtccagtctgaaggcctctgacactgccatgtattattgcgccaggcacgtt acgatgatctggggggtgatcatcgacttctggggccagggcacactcgtaaccgtcagttcggaggtggtggatcccag gtt cag ctg gtg cag tcc ggc gcc gag gtg aag aag ccg ggc gct tct gtg aag gtc agc tgt aaa gcc agt ggc tac aca ttc acc agg tac act atg cac tgg gtg cgc cag gca ccc ggg cag ggg ctg gaa tgg atc ggg tac atc aat cct tcc cgc ggt tat act aac tat aat caa aag ttc aaa gac cgc gtg aca att acg acc gat aag agt tca tcc acc gct tac tta cag atg aac tcc ctc aag aca gag gac acc gcc gtg tac tac tgt gcc cgc tac tac gac gac cat tac tgc ctg gac tac tgg ggc cag ggg acc acc gta acc gtc agt agt ggc ggg ggc ggc agt cag atc gtg ctg acc cag agt ccg gcg acc ctg agt ctg tct cct ggt gag cgc gca acg ctg acg tgc tca gcc tcc tcg agt gcc tct tat atg aac tgg tac cag cag aag ccc ggc aag gcc cct aag cgc tgg atc tac gac acc tcg aag cta gct tcg ggc gtc ccc tcc cgg ttc tcg ggc tcg ggg tcg ggc acg gac tat tct ctg acc atc aac agt ctg gag gca gag gac gcc gca acc tac tac tgc cag cag tgg agt tcg aat cct ttc acg ttt ggg cag ggg acc aag gtg gaa atc aaa cac cat cac cac cat cac TAA TAA gcggccgc D4-DIVHv6 (D4-Hv6) (SEQ ID NO: 12)
Atgggctggtcttgcatcatcctgttcctcgtggccaccgccaccggcgtccacagcgccatccagctcacccagagccc ctcgagcttgagtgcctcggtgggagaccgggtcactatcacctgccgagccagtcagggcatctcctccgcccttgcctg -continued gtaccagcagaagcccgggaaggccccaagctgctgatctacgacgctagtagtctggagagtggcgtgccttcgcgc ttctcgggcagtggagtggcaccgacttcaccttgaccatctccagtctacagccggaagatttcgcgacctactactgtc agcaattcaactcttatccatacactttcggccaggggacaaagctggagatcaagggcgggggcgggagtggcggcgg agggtccggaggcggggctccgaggtgcaactagtccagagcggagccgaggtgaagaagcccggggagagtcta aagatctcttgcaagggctccggttactccttctcgagttcctggatcgggtgggtgcgacagatgccgggcaagggcctg gagtggatgggcattatctaccccgacgactccgataccgttatagtccatcgttccagggacaggtgaccatttccgccg acaagtctatcagaaccgcctatctgcagtggtccagtctgaaggcctctgacactgccatgtattattgcgccaggcacgtt acgatgatctgggggtgatcatcgacttctggggccagggcacactcgtaaccgtcagttcggaggtggtggatcccag gttcagctggtgcagtccggcgccgaggtgaagaagccgggcgcttctgtgaaggtcagctgtaaagccagtggctaca cattcaccaggtacactatgcactgggtgcgccaggcacccgggcagggctggaatggatcgggtacatcaatccttcc cgcggttatactaactatGCtcaaaagttcCaagaccgcgtgacaattacgaccgataagagttcatccaccgcttacttac agatgaactccctcaagacagaggacaccgccgtgtactactgtgcccgctactacgacgaccattactgcctggactact ggggccaggggaccaccgtaaccgtcagtagtggcggggcggcagtcagatcgtgctgacccagagtccggcgacc ctgagtctgtctcctggtgagcgcgcaacgctgacgtgctcagcctcctcgagtgcctcttatatgaactggtaccagcaga agcccggcaaggcccctaagcgctggatctacgacacctcgaagctagcttcgggcgtcccctcccggttctcgggctcg gggtcgggcacggactattctctgaccatcaacagtctggaggcagaggacgccgcaacctactactgccagcagtgga gttcgaatcctacacgtttgggcaggggaccaaggtggaaatcaaacaccatcaccaccatcacTAATAAgcggcc gc D4-DIVHv7 (D4-Hv7) (SEQ ID NO: 13)
Atgggctggtcttgcatcatcctgttcctcgtggccaccgccaccggcgtccacagcgccatccagctcacccagagccc ctcgagcttgagtgcctcggtgggagaccgggtcactatcacctgccgagccagtcagggcatctcctccgcccttgcctg gtaccagcagaagcccgggaaggccccaagctgctgatctacgacgctagtagtctggagagtggcgtgccttcgcgc ttctcgggcagtggagtggcaccgacttcaccttgaccatctccagtctacagccggaagatttcgcgacctactactgtc agcaattcaactcttatccatacactttcggccaggggacaaagctggagatcaagggcgggggcgggagtggcggcgg agggtccggaggcggggctccgaggtgcaactagtccagagcggagccgaggtgaagaagcccggggagagtcta aagatctcttgcaagggctccggttactccttctcgagttcctggatcgggtgggtgcgacagatgccgggcaagggcctg gagtggatgggcattatctaccccgacgactccgataccgttatagtccatcgttccagggacaggtgaccatttccgccg acaagtctatcagaaccgcctatctgcagtggtccagtctgaaggcctctgacactgccatgtattattgcgccaggcacgtt acgatgatctgggggtgatcatcgacttctggggccagggcacactcgtaaccgtcagttcggaggtggtggatcccag gttcagctggtgcagtccggcgccgaggtgaagaagccgggcgcttctgtgaaggtcagctgtaaagccagtggctaca cattcaccaggtacactatgcactgggtgcgccaggcacccgggcagggctggaatggatcgggtacatcaatccttcc cgcggttatactaactataatcaaaagGtcaaagaccgcTtgacaattacgaccgataagagttcatccaccgcttacttac agatgaactccctcaagacagaggacaccgccgtgtactactgtgcccgctactacgacgaccattactgcctggactact ggggccaggggaccaccgtaaccgtcagtagtggcggggcggcagtcagatcgtgctgacccagagtccggcgacc ctgagtctgtctcctggtgagcgcgcaacgctgacgtgctcagcctcctcgagtgcctcttatatgaactggtaccagcaga agcccggcaaggcccctaagcgctggatctacgacacctcgaagctagcttcgggcgtcccctcccggttctcgggctcg gggtcgggcacggactattctctgaccatcaacagtctggaggcagaggacgccgcaacctactactgccagcagtgga gttcgaatcctttcacgtttgggcaggggaccaaggtggaaatcaaacaccatcaccaccatcacTAATAAgcggcc gc Blina-27H VL1 (Blina-VL1) (SEQ ID NO: 14)
atgggatggagctgtatcatcctcttcttggtagcaacagctacaggtgtccactccgactacaaagatgatgacgataagg atatccagctgacccagtctccagcttctttggctgtgtctctagggcagagggccaccatctcctgcaaggccagccaaag -continued

```
tgttgattatgatggtgatagttatttgaactggtaccaacagattccaggacagccacccaaactcctcatctatgatgcatcc aatctagtttctgggatcccacccaggtttagtggcagtgggtctgggacagacttcaccctcaacatccatcctgtggagaa ggtggatgctgcaacctatcactgtcagcaaagtactgaggatccgtggacgttcggtggagggaccaagctcgagatca aaggtggtggtggttctggcggcggcggctccggtggtggtggttctcaggtgcagctgcagcagtctgggctgagctg gtgaggcctgggtcctcagtgaagatttcctgcaaggcttctggctatgcattcagtagctactggatgaactgggtgaagc agaggcctggacagggtcttgagtggattggacagatttggcctggagatggtgatactaactacaatggaaagttcaagg gtaaagccactctgactgcagacgaatcctccagcacagcctacatgcaactcagcagcctagcatctgaggactctgcg gtctatttctgtgcaagacgggagactacgacggtaggccgttattactatgctatggactactggggccaagggaccacg gtcaccgtctcctccggaggtggtggatcccag GTG cag ctc gtg gag TCC ggc GGC ggc GTT GTC cag CCT GGC cgc TCG ctg cgc ctg tca tgc GCC GCT TCG ggt ttc ACG ttc agg TCG TAC GGG atg cac tgg GTC AGG cag GCG CCG gga AAA GGC CTG gag tgg GTG GCT atc ATC tgg TAC GAC ggc TCC aag aag AAT TAT GCT gac TCC GTC aag gga CGG ttc ACA atc tcg CGT GAT aac tcg aag aac acc CTC TAC CTG cag atg AAT TCC CTC AGA GCC GAA gac ACA GCC gtg TAT TAT tgc GCC AGG ggc ACC ggc tat aac tgg TTC GAT CCA tgg ggc cag GGG ACC ctg GTT acc GTC tcc tcc GGA GGG GGG GGT agt gag atc gtg ctg acc cag tcg CCT CGC ACC CTG tcc CTG tcc CCT GGG gag CGC gcc ACC CTC tcg tgc AGG GCA tcg cag TCC gtc agt TCC TCC TAT ctg GCC tgg tac CAG cag aaa CCT ggc cag GCA cca AGG CTG ctg ATC tac GGA GCT tcc TCG AGG GCA ACC GGG ATC CCC gac AGA TTT tcc GGA agc GGA AGT GGC ACA gac ttc ACC ctg acc ATC AGT AGG CTT GAC CCC gaa GAT ttc GCC GTG tac TAT tgc cag cag tac GGC TCC TCC ccc atc acc ttc ggc cag GGC ACA AGA ctg gag atc aag cac CAT cac cac cac cac TAA TAA gcggccgc
```

Blina-27H VL2 (Blina-VL2) (SEQ ID NO: 15)

```
atgggatggagctgtatcatcctcttcttggtagcaacagctacaggtgtccactccgactacaaagatgatgacgataagg atatccagctgacccagtctccagcttattggctgtgtctctagggcagagggccaccatctcctgcaaggccagcaaag tgttgattatgatggtgatagttatttgaactggtaccaacagattccaggacagccacccaaactcctcatctatgatgcatcc aatctagtttctgggatcccacccaggtttagtggcagtgggtctgggacagacttcaccctcaacatccatcctgtggagaa ggtggatgctgcaacctatcactgtcagcaaagtactgaggatccgtggacgttcggtggagggaccaagctcgagatca aaggtggtggtggttctggcggcggcggctccggtggtggtggttctcaggtgcagctgcagcagtctgggctgagctg gtgaggcctgggtcctcagtgaagatttcctgcaaggcttctggctatgcattcagtagctactggatgaactgggtgaagc agaggcctggacagggtcttgagtggattggacagatttggcctggagatggtgatactaactacaatggaaagttcaagg gtaaagccactctgactgcagacgaatcctccagcacagcctacatgcaactcagcagcctagcatctgaggactctgcg gtctatttctgtgcaagacgggagactacgacggtaggccgttattactatgctatggactactggggccaagggaccacg gtcaccgtctcctccggaggtggtggatccCAG GTA CAG ctg GTC GAG tcc GGT ggg GGC gtg GTC cag CCC ggc CGG tcc CTG CGC CTG TCG tgc GCT GCC TCC ggc TTT ACC ttc CGG TCG TAT GGC atg CAT tgg gtg cgc cag GCC CCC GGG aag ggg ctg gag tgg GTC gcc ATT ATC tgg tac gat GGC TCC AAG aag aac TAC gct GAT TCG GTT aag ggc cgc TTC ACC att AGT CGG GAT aat TCG aag aat ACG CTG TAT CTC CAG atg aac TCC ctg AGG GCC GAG gac act gcc GTG TAC TAC tgc gcc CGG GGC ACA GGC TAT aac tgg ttc gat ccc tgg GGT cag ggc ACC CTA gtg ACC
```

```
GTC TCG TCT GGG GGC GGA ggg TCA GAT att ctc atg ACA cag TCG ccc TCT

AGT CTT tcc GCC tcc gtg GGG GAC CGC GTG acc atc ACA tgc AGA GCT TCC

CAG GGG atc tcc TCT GCG CTG gcc tgg TAT cag cag aag ccc GGG aag GCA

CCC AAG ctg CTC ATC TAT TAC GCT tct TCG CTG CAA AGT GGG gtg ccg

TCC CGC TTC tcc gga AGC ggc TCC ggc ACG GAC tac acc CTC acc atc tcc TCC

CTG CAG CCT GAG GAT ttc GCC acc TAT tac tgc cag cag TAT tac TCC acg ctg

ACC TTC GGA GGA GGC ACG AAA GTG gag atc aag CAC cac cac cac cac cac

TAA TAA gcggccgc
```

Blina-28F11 (Blina-F11) (SEQ ID NO: 16)
atgggatggagctgtatcatcctcttcttggtagcaacagctacaggtgtccactccgactacaaagatgatgacgataagg atatccagctgacccagtctccagcttctttggctgtgtctctagggcagagggccaccatctcctgcaaggccagccaaag tgttgattatgatggtgatagttatttgaactggtaccaacagattccaggacagccacccaaactcctcatctatgatgcatcc aatctagtttctggatcccacccaggtttagtggcagtgggtctgggacagacttcaccctcaacatccatcctgtggagaa ggtggatgctgcaacctatcactgtcagcaaagtactgaggatccgtggacgttcggtggagggaccaagctcgagatca aaggtggtggtggttctggcggcggcggctccggtggtggtggttctcaggtgcagctgcagcagtctggggctgagctg gtgaggcctgggtcctcagtgaagatttcctgcaaggcttctggctatgcattcagtagctactggatgaactgggtgaagc agaggcctggacagggtcttgagtggattggacagatttggcctggagatggtgatactaactacaatggaaagttcaagg gtaaagccactctgactgcagacgaatcctccagcacagcctacatgcaactcagcagcctagcatctgaggactctgcg gtctatttctgtgcaagacgggagactacgacggtaggccgttattactatgctatggactactggggccaagggaccacg gtcaccgtctcctccggaggtggtggatcccag GTC cag ctg GTT gag TCT GGT GGC GGA gtg gtc cag CCC ggc CGG TCT CTC CGC ctg TCC tgc GCC GCT tcc GGG ttc AAG TTC TCC ggc TAC gga atg cac tgg gtg AGG cag GCG CCA GGT aag GGG CTC GAG tgg GTC GCG gtg ATA tgg TAT gac GGT AGC aag aag tat tac gtg gac AGT GTG AAA ggc CGC TTT acc atc TCA CGC GAC AAT TCT aag aac acc ctg TAC CTC CAG atg aac TCC ctg CGC gct gag GAC ACG GCG GTG TAC tac TGC GCT AGG cag atg GGG tac tgg cac TTC gac CTT tgg ggc AGG GGT acc CTG GTG acc gtc TCA TCC GGC ggc ggc GGG TCT gag ATC GTT CTG ACC CAA AGT CCG gcc ACA ctg tcc CTC TCC CCA GGA gag cgc GCT ACG CTT AGC tgc CGC gcc tcc cag AGC GTG TCC tcc tac ctg gca tgg TAT cag cag aag CCG GGG cag GCG CCT CGA ctg CTG atc tac gac gcc TCG aac CGC GCG ACA GGT atc ccc gcg CGC ttc AGC GGC TCC GGT TCG GGG ACT GAT ttc acc ctg ACC atc tcc TCC CTC GAG cct gag GAT ttc GCA gtg tac tac tgc cag cag aga TCC AAT tgg ccc CCC CTC acc ttc ggc GGG GGA acc aag GTG gag atc aag cac cac cac cac CAT cac TAATAA Blina-DIVHv5 (Blina-Hv5) (SEQ ID NO: 17)
atgggatggagctgtatcatcctcttcttggtagcaacagctacaggtgtccactccgactacaaagatgatgacgataagg atatccagctgacccagtctccagcttctttggctgtgtctctagggcagagggccaccatctcctgcaaggccagccaaag tgttgattatgatggtgatagttatttgaactggtaccaacagattccaggacagccacccaaactcctcatctatgatgcatcc aatctagtttctggatcccacccaggtttagtggcagtgggtctgggacagacttcaccctcaacatccatcctgtggagaa ggtggatgctgcaacctatcactgtcagcaaagtactgaggatccgtggacgttcggtggagggaccaagctcgagatca aaggtggtggtggttctggcggcggcggctccggtggtggtggttctcaggtgcagctgcagcagtctggggctgagctg gtgaggcctgggtcctcagtgaagatttcctgcaaggcttctggctatgcattcagtagctactggatgaactgggtgaagc agaggcctggacagggtcttgagtggattggacagatttggcctggagatggtgatactaactacaatggaaagttcaagg -continued

```
gtaaagccactctgactgcagacgaatcctccagcacagcctacatgcaactcagcagcctagcatctgaggactctgcg gtctatttctgtgcaagacgggagactacgacggtaggccgttattactatgctatggactactggggccaagggaccacg gtcaccgtctcctccggaggtggtggatcccag gtt cag ctg gtg cag tcc ggc gcc gag gtg aag aag ccg ggc gct tct gtg aag gtc agc tgt aaa gcc agt ggc tac aca ttc acc agg tac act atg cac tgg gtg cgc cag gca ccc ggg cag ggg ctg gaa tgg atc ggg tac atc aat cct tcc cgc ggt tat act aac tat aat caa aag ttc aaa gac cgc gtg aca att acg acc gat aag agt tca tcc acc gct tac tta cag atg aac tcc ctc aag aca gag gac acc gcc gtg tac tac tgt gcc cgc tac tac gac gac cat tac tgc ctg gac tac tgg ggc cag ggg acc acc gta acc gtc agt agt ggc ggg ggc ggc agt cag atc gtg ctg acc cag agt ccg gcg acc ctg agt ctg tct cct ggt gag cgc gca acg ctg acg tgc tca gcc tcc tcg agt gcc tct tat atg aac tgg tac cag cag aag ccc ggc aag gcc cct aag cgc tgg atc tac gac acc tcg aag cta gct tcg gcc gtc ccc tcc cgg ttc tcg ggc tcg ggg tcg ggc acg gac tat tct ctg acc atc aac agt ctg gag gca gag gac gcc gca acc tac tac tgc cag cag tgg agt tcg aat cct ttc acg ttt ggg cag ggg acc aag gtg gaa atc aaa cac cat cac cac cat cac TAA TAA gcggccgc
```

Blina-DIVHv6 (Blina-Hv6) (SEQ ID NO: 18)

```
atgggatggagctgtatcatcctcttcttggtagcaacagctacaggtgtccactccgactacaaagatgatgacgataagg atatccagctgacccagtctccagcttctttggctgtgtctctagggcagagggccaccatctcctgcaaggccagccaaag tgttgattatgatggtgatagttatttgaactggtaccaacagattccaggacagccacccaaactcctcatctatgatgcatcc aatctagtnctgggatcccacccaggtttagtggcagtgggtctgggacagacttcaccctcaacatccatcctgtggagaa ggtggatgctgcaacctatcactgtcagcaaagtactgaggatccgtggacgttcggtggagggaccaagctcgagatca aaggtggtggtggttctggcggcggcggctccggtggtggtggttctcaggtgcagctgcagcagtctggggctgagctg gtgaggcctgggtcctcagtgaagatttcctgcaaggcttctggctatgcattcagtagctactggatgaactgggtgaagc agaggcctggacagggtcttgagtggattggacagatttggcctggagatggtgatactaactacaatggaaagttcaagg gtaaagccactctgactgcagacgaatcctccagcacagcctacatgcaactcagcagcctagcatctgaggactctgcg gtctatttctgtgcaagacgggagactacgacggtaggccgttattactatgctatggactactggggccaagggaccacg gtcaccgtctcctccggaggtggtggatcccaggttcagctggtgcagtccggcgccgaggtgaagaagccgggcgctt ctgtgaaggtcagctgtaaagccagtggctacacattcaccaggtacactatgcactgggtgcgccaggcacccgggcag gggctggaatggatcgggtacatcaatccttcccgcggttatactaactatGCtcaaaagttcCaagaccgcgtgacaatt acgaccgataagagttcatccaccgcttacttacagatgaactccctcaagacagaggacaccgccgtgtactactgtgcc cgctactacgacgaccattactgcctggactactggggccaggggaccaccgtaaccgtcagtagtggcgggggcggca gtcagatcgtgctgacccagagtccggcgaccctgagtctgtctcctggtgagcgcgcaacgctgacgtgctcagcctcct cgagtgcctcttatatgaactggtaccagcagaagcccggcaaggcccctaagcgctggatctacgacacctcgaagcta gcttcgggcgtcccctcccggttctcgggctcggggtcgggcacggactattctctgaccatcaacagtctggaggcaga ggacgccgcaacctactactgccagcagtggagttcgaatcctttcacgtttgggcaggggaccaaggtggaaatcaaac accatcaccaccatcacTAATAAgcggccgc
```

Blina-DIVHv7 (Blina-Hv7) (SEQ ID NO: 19):

```
atgggatggagctgtatcatcctcttcttggtagcaacagctacaggtgtccactccgactacaaagatgatgacgataagg atatccagctgacccagtctccagcttctttggctgtgtctctagggcagagggccaccatctcctgcaaggccagccaaag tgttgattatgatggtgatagttatttgaactggtaccaacagattccaggacagccacccaaactcctcatctatgatgcatcc aatctagtttctgggatcccacccaggtttagtggcagtgggtctgggacagacttcaccctcaacatccatcctgtggagaa ggtggatgctgcaacctatcactgtcagcaaagtactgaggatccgtggacgttcggtggagggaccaagctcgagatca aaggtggtggtggttctggcggcggcggctccggtggtggtggttctcaggtgcagctgcagcagtctggggctgagctg
```

-continued gtgaggcctgggtcctcagtgaagatttcctgcaaggcttctggctatgcattcagtagctactggatgaactgggtgaagc agaggcctggacagggtcttgagtggattggacagatttggcctggagatggtgatactaactacaatggaaagttcaagg gtaaagccactctgactgcagacgaatcctccagcacagcctacatgcaactcagcagcctagcatctgaggactctgcg gtctatttctgtgcaagacgggagactacgacggtaggccgttattactatgctatggactactggggccaagggaccacg gtcaccgtctcctccggaggtggtggatcccaggttcagctggtgcagtccggcgccgaggtgaagaagccgggcgctt ctgtgaaggtcagctgtaaagccagtggctacacattcaccaggtacactatgcactgggtgcgccaggcacccgggcag gggctggaatggatcgggtacatcaatccttcccgcggttatactaactataatcaaaagGtcaaagaccgcTtgacaatt acgaccgataagagttcatccaccgcttacttacagatgaactccctcaagacagaggacaccgccgtgtactactgtgcc cgctactacgacgaccattactgcctggactactggggccaggggaccaccgtaaccgtcagtagtggcggggcggca gtcagatcgtgctgacccagagtccggcgaccctgagtctgtctcctggtgagcgcgcaacgctgacgtgctcagcctcct cgagtgcctcttatatgaactggtaccagcagaagcccggcaaggcccctaagcgctggatctacgacacctcgaagcta gcttcgggcgtccctcccggttctcgggctcggggtcgggcacggactattctctgaccatcaacagtctggaggcaga ggacgccgcaacctactactgccagcagtggagttcgaatcctttcacgtttgggcaggggaccaaggtggaaatcaaac accatcaccaccatcacTAATAAgcggccgc D4(19)-BBz ORF (SEQ ID NO: 20):
atgggctggtcttgcatcatcctgttcctcgtggccaccgccaccggcgtccacagcgccatccagctcacccagagcccc tcgagcttgagtgcctcggtgggagaccgggtcactatcacctgccgagccagtcagggcatctcctccgcccttgcctgg taccagcagaagcccgggaaggcccccaagctgctgatctacgacgctagtagtctggagagtggcgtgccttcgcgctt ctcgggcagtgggagtggcaccgacttcaccttgaccatctccagtctacagccggaagatttcgcgacctactactgtcag caattcaactcttatccatacactttcggccaggggacaaagctggagatcaagggcggggcgggagtggcggcggag ggtccggaggcgggggctccgaggtgcaactagtccagagcggagccgaggtgaagaagcccggggagagtctaaa gatctcttgcaagggctccggttactccttctcgagttcctggatcggtgggtgcgacagatgccgggcaagggcctgga gtggatgggcattatctaccccgacgactccgatacccgttatagtccatcgttccagggacaggtgaccatttccgccgac aagtctatcagaaccgcctatctgcagtggtccagtctgaaggcctctgacactgccatgtattattgcgccaggcacgttac gatgatctgggggtgatcatcgacttctggggccagggcacactcgtaaccgtcagttctgcggccgcaaccacgacgc cagcgccgcgaccaccaacaccggcgccaccatcgcgtcgcagcccctgtccctgcgcccagaggcgtgccggcca gcggcggggggcgcagtgcacacgaggggctggacttcgcctgtgatatctacatctgggcgcccttggccgggactt gtggggtccttctcctgtcactggttatcaccctttactgcaaacggggcagaaagaaactcctgtatatattcaaacaaccat ttatgagaccagtacaaactactcaagaggaagatggctgtagctgccgatttccagaagaagaagaaggaggatgtgaa ctgagagtgaagttcagcaggagcgcagacgcccccgcgtacaagcagggccagaaccagctctataacgagctcaat ctaggacgaagagaggagtacgacgttttggacaagagacgtggccgggaccctgagatggggggaaagccgagaag gaagaaccctcaggaaggcctgtacaatgaactgcagaaagataagatggcggaggcctacagtgagattgggatgaaa ggcgagcgccggagggcaaggggcacgatggcctttaccagggtctcagtacagccaccaaggacacctacgacgc ccttcacatgcaggccctgccccctcgctaataa 12B(19)-BBZ ORF (SEQ ID NO: 21):
atggggtggtcgtgcatcatcctgtttctggtggccacagcaaccggcgtgcacagtgagattgtgctgacccaaagcccg gacttccagtccgtgacccccaaggagaaggttaccatcacgtgccgcgcctctgaaagcgtggacacgttcgggatctc cttcatgaattggtttcagcagaagccagatcagtcacccaaactcctgatccacgccgccagtaatcagggctcaggcgtc ccgtccaggttctctggcagtggctccggtactgacttcaccttaaccatcaactctctggaggcagaggacgccgccacat -continued

```
acttctgccaacagagcaaggaggtgcccttcaccttcggaggtgggaccaaggtcgaaatcaagggagggggggggt ccggcggcggcggatccggaggcggcggcagcgaggtgcagctcgtcgagagtggggcggactggtgcaaccag ggggctctctgcggctgagctgcgctgcctccggattcacattctcctcgtcctggatgaactgggttcgccaggcccccg gcaaaggcctggagtgggtcggcagaatctacccaggcgacggggacacgaactacaacggcaagttcaagggccgg ttcacaatctcgcgcgacgactcaaaaaacagcctgtatctccagatgaactccctgaaaaccgaggacaccgccgtgtatt actgtgcacgcagcggctttatcaccaccgttctggacttcgattattggggccagggtaccctggtgacggtaagttcggc ggccgcaaccacgacgccagcgccgcgaccaccaacaccggcgcccaccatcgcgtcgcagcccctgtccctgcgcc cagaggcgtgccggccagcggcggggggcgcagtgcacacgaggggctggacttcgcctgtgatatctacatctggg cgcccttggccgggacttgtggggtccttctcctgtcactggttatcacccctttactgcaaacggggcagaaagaaactcctg tatatattcaaacaaccatttatgagaccagtacaaactactcaagaggaagatggctgtagctgccgatttccagaagaaga agaaggaggatgtgaactgagagtgaagttcagcaggagcgcagacgcccccgcgtacaagcagggccagaaccagc tctataacgagctcaatctaggacgaagagaggagtacgacgttttggacaagagacgtggccgggaccctgagatggg gggaaagccgagaaggaagaaccctcaggaaggcctgtacaatgaactgcagaaagataagatggcggaggcctaca gtgagattgggatgaaaggcgagcgccggaggggcaaggggcacgatggcctttaccagggtctcagtacagccacca aggacacctacgacgcccttcacatgcaggccctgccccctcgctaataa Blina.19BBZ ORF (SEQ ID NO: 22):
atgggatggagctgtatcatcctcttcttggtagcaacagctacaggtgtccactccgactacaaagatgatgacgataagg atatccagctgacccagtctccagcttctttggctgtgtctctagggcagagggccaccatctcctgcaaggccagccaaag tgttgattatgatggtgatagttatttgaactggtaccaacagattccaggacagccacccaaactcctcatctatgatgcatcc aatctagtttctgggatcccacccaggtttagtggcagtgggtctgggacagacttcaccctcaacatccatcctgtggagaa ggtggatgctgcaacctatcactgtcagcaaagtactgaggatccgtggacgttcggtggagggaccaagctcgagatca aaggtggtggtggttctggcggcggcggctccggtggtggtggttctcaggtgcagctgcagcagtctggggctgagctg gtgaggcctgggtcctcagtgaagatttcctgcaaggcttctggctatgcattcagtagctactggatgaactgggtgaagc agaggcctggacagggtcttgagtggattggacagatttggcctggagatggtgatactaactacaatggaaagttcaagg gtaaagccactctgactgcagacgaatcctccagcacagcctacatgcaactcagcagcctagcatctgaggactctgcg gtctatttctgtgcaagacgggagactacgacggtaggccgttattactatgctatggactactggggccaagggaccacg gtcaccgtctcctccgcggccgcaaccacgacgccagcgccgcgaccaccaacaccggcgcccaccatcgcgtcgca gcccctgtccctgcgcccagaggcgtgccggccagcggcggggggcgcagtgcacacgaggggctggacttcgcct gtgatatctacatctgggcgcccttggccgggacttgtggggtccttctcctgtcactggttatcacccctttactgcaaacggg gcagaaagaaactcctgtatatattcaaacaaccatttatgagaccagtacaaactactcaagaggaagatggctgtagctg ccgatttccagaagaagaagaaggaggatgtgaactgagagtgaagttcagcaggagcgcagacgcccccgcgtacaa gcagggccagaaccagctctataacgagctcaatctaggacgaagagaggagtacgacgatggacaagagacgtggc cgggaccctgagatgggggaaagccgagaaggaagaaccctcaggaaggcctgtacaatgaactgcagaaagataa gatggcggaggcctacagtgagattgggatgaaaggcgagcgccggaggggcaaggggcacgatggcctttaccagg gtctcagtacagccaccaaggacacctacgacgcccttcacatgcaggccctgccccctcgctaataa
```

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An ex vivo or in vitro method of generating a modified T cell, comprising introducing into a T cell a composition comprising
   (a) a first RNA molecule encoding a chimeric antigen receptor (CAR), wherein the CAR comprises an antigen binding domain, a transmembrane domain, and a CD3 zeta signaling domain; and
   (b) a second RNA molecule encoding a bispecific antibody, wherein the bispecific antibody comprises a first antigen recognition domain that recognizes the same antigen as the antigen binding domain of the CAR, and a second antigen recognition domain that recognizes CD3 wherein the bispecific antibody encoded by the second RNA molecule is secreted by the cell.

2. The method of claim 1, wherein the CAR further comprises a costimulatory signaling region.

3. An ex vivo or in vitro method of enhancing an anti-tumor activity of a T cell, comprising introducing into a T cell a composition comprising
   (a) a first RNA molecule encoding a chimeric antigen receptor (CAR), wherein the CAR comprises an antigen binding domain, a transmembrane domain, and a CD3 zeta signaling domain; and
   (b) a second RNA molecule encoding a bispecific antibody, wherein the bispecific antibody comprises a first antigen recognition domain that recognizes the same antigen as the antigen binding domain of the CAR, and a second antigen recognition domain that recognizes CD3,
   wherein the bispecific antibody encoded by the second RNA is secreted by the cell, and wherein the secreted bispecific antibody further stimulates the modified T cell and non-modified bystander T cells to specifically recognize tumor cells.

4. The ex vivo or in vitro method of claim 3, wherein the antigen binding domain of the CAR binds CD19, CD20, CD22, ROR1, mesothelin, CD33/IL3Ra, c-Met, PSMA, Glycolipid F77, EGFRvIII, or GD-2.

5. The ex vivo or in vitro method of claim 3, wherein the bispecific antibody is encoded by a nucleic acid comprising a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

6. The ex vivo or in vitro method of claim 3, wherein the CAR comprises a polypeptide encoded by the nucleic acid sequence selected from the group consisting of SEQ ID NO: 20, SEQ ID NO: 21, and SEQ ID NO: 22.

7. A T cell genetically modified to express a CAR and a bispecific antibody, wherein:
   (a) the CAR comprises an antigen binding domain, a transmembrane domain, and a CD3 zeta signaling domain; and
   (b) the bispecific antibody comprises a first antigen recognition domain that recognizes the same antigen as the antigen binding domain of the CAR, and a second antigen recognition domain that recognizes CD3,
   (c) the bispecific antibody is secreted by the cell; and
   (d) the secreted bispecific antibody further stimulates the modified T cell and non-modified bystander T cells to specifically recognize tumor cells.

8. The T cell of claim 7, wherein the bispecific antibody comprises:
   (a) a human antibody, or an antigen-binding fragment thereof, or
   (b) a humanized antibody, or an antigen-binding fragment thereof.

9. The T cell of claim 7, wherein the CAR further comprises a costimulatory signaling region.

10. A method of treating cancer in a human, comprising administering to the human the T cell of claim 7.

11. An ex vivo or in vitro method of enhancing an anti-tumor activity of a T cell, comprising introducing into a T cell a composition comprising
   (a) a first lentiviral vector encoding a chimeric antigen receptor (CAR), wherein the CAR comprises an antigen binding domain, a transmembrane domain, and a CD3 zeta signaling domain; and
   (b) a second lentiviral vector encoding a bispecific antibody, wherein the bispecific antibody comprises a first antigen recognition domain that recognizes the same antigen as the antigen binding domain of the CAR, and a second antigen recognition domain that recognizes CD3,
   wherein the bispecific antibody encoded by the second lentiviral vector is secreted by the cell, and wherein the secreted bispecific antibody further stimulates the modified T cell and non-modified bystander T cells to specifically recognize tumor cells.

12. The method of claim 11, wherein the CAR further comprises a costimulatory signaling region.

13. The ex vivo or in vitro method of claim 11, wherein the antigen binding domain of the CAR binds CD19, CD20, CD22, ROR1, mesothelin, CD33/IL3Ra, c-Met, PSMA, Glycolipid F77, EGFRvIII, or GD-2.

14. The ex vivo or in vitro method of claim 11, wherein the bispecific antibody is encoded by a nucleic acid comprising a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

15. The ex vivo or in vitro method of claim 11, wherein the CAR comprises a polypeptide encoded by the nucleic acid sequence selected from the group consisting of SEQ ID NO: 20, SEQ ID NO: 21, and SEQ ID NO: 22.

16. An ex vivo or in vitro method of generating a modified T cell, comprising introducing into a T cell a composition comprising
   (a) a first lentiviral vector encoding a chimeric antigen receptor (CAR), wherein the CAR comprises an antigen binding domain, a transmembrane domain, and a CD3 zeta signaling domain; and
   (b) a second lentiviral vector encoding a bispecific antibody, wherein the bispecific antibody comprises a first antigen recognition domain that recognizes the same antigen as the antigen binding domain of the CAR, and a second antigen recognition domain that recognizes CD3 wherein the bispecific antibody encoded by the second lentiviral vector is secreted by the cell.

* * * * *

SEQUENCE LISTING

<160> NUMBER OF SEQ ID NOS: 22

<210> SEQ ID NO 1
<211> LENGTH: 1605
<212> TYPE: DNA
<213> ORGANISM: Artificial
<220> FEATURE:
<223> OTHER INFORMATION: Chemically synthesized

<400> SEQUENCE: 1

| | | | | | |
|---|---|---|---|---|---|
| atgggatgga | gctgtatcat | cctcttcttg | gtagcaacag | ctacaggtgt | ccactccgac | 60 |
| tacaaagatg | atgacgataa | ggatatccag | ctgacccagt | ctccagcttc | tttggctgtg | 120 |
| tctctagggc | agagggccac | catctcctgc | aaggccagcc | aaagtgttga | ttatgatggt | 180 |
| gatagttatt | tgaactggta | ccaacagatt | ccaggacagc | cacccaaact | cctcatctat | 240 |
| gatgcatcca | atctagtttc | tgggatccca | cccaggttta | gtggcagtgg | gtctgggaca | 300 |
| gacttcaccc | tcaacatcca | tcctgtggag | aaggtggatg | ctgcaaccta | tcactgtcag | 360 |
| caaagtactg | aggatccgtg | gacgttcggt | ggagggacca | agctcgagat | caaaggtggt | 420 |
| ggtggttctg | gcggcggcgg | ctccggtggt | ggtggttctc | aggtgcagct | gcagcagtct | 480 |
| ggggctgagc | tggtgaggcc | tgggtcctca | gtgaagattt | cctgcaaggc | ttctggctat | 540 |
| gcattcagta | gctactggat | gaactgggtg | aagcagaggc | ctggacaggg | tcttgagtgg | 600 |
| attggacaga | tttggcctgg | agatggtgat | actaactaca | atggaaagtt | caagggtaaa | 660 |
| gccactctga | ctgcagacga | atcctccagc | acagcctaca | tgcaactcag | cagcctagca | 720 |
| tctgaggact | ctgcggtcta | tttctgtgca | agacgggaga | ctacgacggt | aggccgttat | 780 |
| tactatgcta | tggactactg | gggccaaggg | accacggtca | ccgtctcctc | cggaggtggt | 840 |
| ggatccgata | tcaaactgca | gcagtcaggg | gctgaactgg | caagacctgg | ggcctcagtg | 900 |
| aagatgtcct | gcaagacttc | tggctacacc | tttactaggt | acacgatgca | ctgggtaaaa | 960 |
| cagaggcctg | acagggtct | ggaatggatt | ggatacatta | atcctagccg | tggttatact | 1020 |
| aattacaatc | agaagttcaa | ggacaaggcc | acattgacta | cagacaaatc | ctccagcaca | 1080 |
| gcctacatgc | aactgagcag | cctgacatct | gaggactctg | cagtctatta | ctgtgcaaga | 1140 |
| tattatgatg | atcattactg | ccttgactac | tggggccaag | gcaccactct | cacagtctcc | 1200 |
| tcagtcgaag | gtggaagtgg | aggttctggt | ggaagtggag | gttcaggtgg | agtcgacgac | 1260 |
| gccgccattc | agctgaccca | gtctccagca | atcatgtctg | catctccagg | ggagaaggtc | 1320 |
| accatgacct | gcagagccag | ttcaagtgta | agttacatga | actggtacca | gcagaagtca | 1380 |
| ggcacctccc | ccaaaagatg | gatttatgac | acatccaaag | tggcttctgg | agtcccttat | 1440 |
| cgcttcagtg | gcagtgggtc | tgggacctca | tactctctca | caatcagcag | catggaggct | 1500 |
| gaagatgctg | ccacttatta | ctgccaacag | tggagtagta | acccgctcac | gttcggtgct | 1560 |
| gggaccaagc | tggagctgaa | acatcatcac | catcatcatt | aataa | | 1605 |

<210> SEQ ID NO 2
<211> LENGTH: 1557
<212> TYPE: DNA
<213> ORGANISM: Artificial
<220> FEATURE:
<223> OTHER INFORMATION: Chemically synthesized

<400> SEQUENCE: 2

| | | | | | |
|---|---|---|---|---|---|
| atgggctggt | cttgcatcat | cctgttcctc | gtggccaccg | ccaccggcgt | ccacagcgcc | 60 |
| atccagctca | cccagagccc | ctcgagcttg | agtgcctcgg | tgggagaccg | ggtcactatc | 120 |

```
acctgccgag ccagtcaggg catctcctcc gcccttgcct ggtaccagca gaagcccggg      180 aaggcccccca agctgctgat ctacgacgct agtagtctgg agagtggcgt gccttcgcgc      240
ttctcgggca gtgggagtgg caccgacttc accttgacca tctccagtct acagccggaa      300
gatttcgcga cctactactg tcagcaattc aactcttatc catacacttt cggccagggg      360
acaaagctgg agatcaaggg cggggggcggg agtggcggcg gagggtccgg aggcggggc      420 tccgaggtgc aactagtcca gagcggagcc gaggtgaaga agcccgggga gagtctaaag      480
atctcttgca agggctccgg ttactccttc tcgagttcct ggatcgggtg ggtgcgacag      540
atgccgggca agggcctgga gtggatgggc attatctacc ccgacgactc cgataccccgt      600 tatagtccat cgttccaggg acaggtgacc atttccgccg acaagtctat cagaaccgcc      660
tatctgcagt ggtccagtct gaaggcctct gacactgcca tgtattattg cgccaggcac      720
gttacgatga tctgggggt gatcatcgac ttctggggcc agggcacact cgtaaccgtc      780
agttctggag gtggtggatc cgatatcaaa ctgcagcagt caggggctga actggcaaga      840
cctggggcct cagtgaagat gtcctgcaag acttctggct acacctttac taggtacacg      900
atgcactggg taaaacagag gcctggacag ggtctggaat ggattggata cattaatcct      960
agccgtggtt atactaatta caatcagaag ttcaaggaca aggccacatt gactacagac     1020
aaatcctcca gcacagccta catgcaactg agcagcctga catctgagga ctctgcagtc     1080
tattactgtg caagatatta tgatgatcat tactgccttg actactgggg ccaaggcacc     1140
actctcacag tctcctcagt cgaaggtgga agtggaggtt ctggtggaag tggaggttca     1200
ggtggagtcg acgacgccgc cattcagctg acccagtctc cagcaatcat gtctgcatct     1260
ccaggggaga aggtcaccat gacctgcaga gccagttcaa gtgtaagtta catgaactgg     1320
taccagcaga agtcaggcac ctcccccaaa agatggattt atgacacatc caaagtggct     1380
tctggagtcc cttatcgctt cagtggcagt gggtctggga cctcatactc tctcacaatc     1440
agcagcatgg aggctgaaga tgctgccact tattactgcc aacagtggag tagtaacccg     1500
ctcacgttcg gtgctgggac caagctggag ctgaaacatc atcaccatca tcattaa       1557

<210> SEQ ID NO 3
<211> LENGTH: 1563
<212> TYPE: DNA
<213> ORGANISM: Artificial
<220> FEATURE:
<223> OTHER INFORMATION: Chemically synthesized

<400> SEQUENCE: 3
atggccttac cagtgaccgc cttgctcctg ccgctggcct tgctgctcca cgccgccagg       60
ccgggatccc aggtacaact gcagcagtct gggcctgagc tggagaagcc tggcgcttca      120
gtgaagatat cctgcaaggc ttctggttac tcattcactg gctacaccat gaactgggtg      180
aagcagagcc atgaaagag ccttgagtgg attggactta ttactcctta caatggtgct      240
tctagctaca accagaagtt caggggcaag gccacattaa ctgtagacaa gtcatccagc      300
acagcctaca tggacctcct cagtctgaca tctgaagact ctgcagtcta tttctgtgca      360
agggggggtt acgacgggag gggttttgac tactgggggcc aagggaccac ggtcaccgtc      420
tcctcaggtg gaggcggttc aggcggcggt ggctctagcg gtggcggatc ggacatcgag      480
ctcactcagt ctccagcaat catgtctgca tctccagggg agaaggtcac catgacctgc      540
agtgccagct caagtgtaag ttacatgcac tggtaccagc agaagtcagg cacctccccc      600
aaaagatgga tttacgacac atccaaactg gcttctggag tcccaggtcg cttcagtggc      660
```

| | |
|---|---|
| agtgggtctg gaaactctta ctctctcaca atcagcagcg tggaggctga agacgacgca | 720 |
| acttattact gccagcagtg gagtaagcac cctctcacgt acggtgctgg gacaaagttg | 780 |
| gaaatcaaag gaggtggtgg atccgatatc aaactgcagc agtcaggggc tgaactggca | 840 |
| agacctgggg cctcagtgaa gatgtcctgc aagacttctg gctacacctt tactaggtac | 900 |
| acgatgcact gggtaaaaca gaggcctgga cagggtctgg aatggattgg atacattaat | 960 |
| cctagccgtg gttatactaa ttacaatcag aagttcaagg acaaggccac attgactaca | 1020 |
| gacaaatcct ccagcacagc ctacatgcaa ctgagcagcc tgacatctga ggactctgca | 1080 |
| gtctattact gtgcaagata ttatgatgat cattactgcc ttgactactg ggccaaggc | 1140 |
| accactctca cagtctcctc agtcgaaggt ggaagtggag gttctggtgg aagtggaggt | 1200 |
| tcaggtggag tcgacgacgc cgccattcag ctgacccagt ctccagcaat catgtctgca | 1260 |
| tctccagggg agaaggtcac catgacctgc agagccagtt caagtgtaag ttacatgaac | 1320 |
| tggtaccagc agaagtcagg cacctccccc aaaagatgga tttatgacac atccaaagtg | 1380 |
| gcttctggag tcccttatcg cttcagtggc agtgggtctg ggacctcata ctctctcaca | 1440 |
| atcagcagca tggaggctga agatgctgcc acttattact gccaacagtg gagtagtaac | 1500 |
| ccgctcacgt tcggtgctgg gaccaagctg gagctgaaac atcatcacca tcatcattaa | 1560 |
| taa | 1563 |

<210> SEQ ID NO 4
<211> LENGTH: 1563
<212> TYPE: DNA
<213> ORGANISM: Artificial
<220> FEATURE:
<223> OTHER INFORMATION: Chemically synthesized

<400> SEQUENCE: 4

| | |
|---|---|
| atggcctac cagtgaccgc cttgctcctg ccgctggcct tgctgctcca cgccgccagg | 60 |
| ccgggatccg acatcgagct cactcagtct ccagcaatca tgtctgcatc tccaggggag | 120 |
| aaggtcacca tgacctgcag tgccagctca agtgtaagtt acatgcactg gtaccagcag | 180 |
| aagtcaggca cctcccccaa aagatggatt tacgacacat ccaaactggc ttctggagtc | 240 |
| ccaggtcgct tcagtggcag tgggtctgga aactcttact ctctcacaat cagcagcgtg | 300 |
| gaggctgaag acgacgcaac ttattactgc cagcagtgga gtaagcaccc tctcacgtac | 360 |
| ggtgctggga caaagttgga aatcaaaggt ggtggtggtt ctggcggcgg cggctccggt | 420 |
| ggtggtggtt ctcaggtaca actgcagcag tctgggcctg agctggagaa gcctggcgct | 480 |
| tcagtgaaga tatcctgcaa ggcttctggt tactcattca ctggctacac catgaactgg | 540 |
| gtgaagcaga gccatggaaa gagccttgag tggattggac ttattactcc ttacaatggt | 600 |
| gcttctagct acaaccagaa gttcagtggc aaggccacat taactgtaga caagtcatcc | 660 |
| agcacagcct acatggacct cctcagtctg acatctgaag actctgcagt ctatttctgt | 720 |
| gcaaggggg gttacgacgg agggggtttt gactactggg gccagggac cacggtcacc | 780 |
| gtctcctcag gaggtggtgg atccgatatc aaactgcagc agtcaggggc tgaactggca | 840 |
| agacctgggg cctcagtgaa gatgtcctgc aagacttctg gctacacctt tactaggtac | 900 |
| acgatgcact gggtaaaaca gaggcctgga cagggtctgg aatggattgg atacattaat | 960 |
| cctagccgtg gttatactaa ttacaatcag aagttcaagg acaaggccac attgactaca | 1020 |
| gacaaatcct ccagcacagc ctacatgcaa ctgagcagcc tgacatctga ggactctgca | 1080 |
| gtctattact gtgcaagata ttatgatgat cattactgcc ttgactactg ggccaaggc | 1140 |

| | | |
|---|---|---|
| accactctca cagtctcctc agtcgaaggt ggaagtggag gttctggtgg aagtggaggt | 1200 |
| tcaggtggag tcgacgacgc cgccattcag ctgacccagt ctccagcaat catgtctgca | 1260 |
| tctccagggg agaaggtcac catgacctgc agagccagtt caagtgtaag ttacatgaac | 1320 |
| tggtaccagc agaagtcagg cacctccccc aaaagatgga tttatgacac atccaaagtg | 1380 |
| gcttctggag tcccttatcg cttcagtggc agtgggtctg ggacctcata ctctctcaca | 1440 |
| atcagcagca tggaggctga agatgctgcc acttattact gccaacagtg gagtagtaac | 1500 |
| ccgctcacgt tcggtgctgg gaccaagctg gagctgaaac atcatcacca tcatcattaa | 1560 |
| taa | 1563 |

<210> SEQ ID NO 5
<211> LENGTH: 1566
<212> TYPE: DNA
<213> ORGANISM: Artificial
<220> FEATURE:
<223> OTHER INFORMATION: Chemically synthesized

<400> SEQUENCE: 5

| | | |
|---|---|---|
| atgctgctgc tggtgaccag cctgctgctg tgtgagctgc cccacccgc ctttctgctg | 60 |
| atccccgaca tccagatgac ccagagcccc agcagcgtga cgccagcgt gggcgaccgg | 120 |
| gtgaccatca cctgccgggc cagccagggc atcaacacct ggctggcctg gtatcagcag | 180 |
| aagcccggca aggcccccaa gctgctgatc tacgccgcca gcagcctgaa gagcggcgtg | 240 |
| cccagccggt ttagcggctc tggctctggc gccgacttca ccctgaccat cagcagcctg | 300 |
| cagcccgagg acttcgccac ctactactgc cagcaggcca cagcttcccc ctgacctttt | 360 |
| ggcggcggaa caaaggtgga gatcaagggc agcacctccg gcagcggcaa gcctggcagc | 420 |
| ggcgagggca gcaccaaggg ccaggtgcag ctggtgcaga gcggagccga ggtgaagaag | 480 |
| cctggcgcct ccgtcaaggt gtcctgcgag gccagcggct acaccttcac cagctacggc | 540 |
| ttcagctggg tgcggcaggc accaggccag ggcctcgaat ggatgggctg gatcagcgcc | 600 |
| agcaacggca acacctacta cgcccagaag ctgcagggca gggtcaccat gaccaccgac | 660 |
| accagcacca gcgcgcccta catggaactg cggagcctga aagcgacga caccgccgtg | 720 |
| tactactgcg ccagggtgta cgccgactac gccgattact ggggccaggg caccctggtg | 780 |
| accgtgagca gcggaggtgg tggatccgat atcaaactgc agcagtcagg gctgaactg | 840 |
| gcaagacctg gggcctcagt gaagatgtcc tgcaagactt ctggctacac ctttactagg | 900 |
| tacacgatgc actgggtaaa acagaggcct ggacagggtc tggaatggat tggatacatt | 960 |
| aatcctagcc gtggttatac taattacaat cagaagttca aggacaaggc cacattgact | 1020 |
| acagacaaat cctccagcac agcctacatg caactgagca gcctgacatc tgaggactct | 1080 |
| gcagtctatt actgtgcaag atattatgat gatcattact gccttgacta ctggggccaa | 1140 |
| ggcaccactc tcacagtctc ctcagtcgaa ggtggaagtg gaggttctgg tggaagtgga | 1200 |
| ggttcaggtg gagtcgacga cgccgccatt cagctgaccc agtctccagc aatcatgtct | 1260 |
| gcatctccag gggagaaggt caccatgacc tgcagagcca gttcaagtgt aagttacatg | 1320 |
| aactggtacc agcagaagtc aggcacctcc cccaaaagat ggatttatga cacatccaaa | 1380 |
| gtggcttctg gagtccctta tcgcttcagt ggcagtgggt ctgggacctc atactctctc | 1440 |
| acaatcagca gcatggaggc tgaagatgct gccacttatt actgccaaca gtggagtagt | 1500 |
| aacccgctca cgttcggtgc tgggaccaag ctggagctga acatcatca ccatcatcat | 1560 |
| taataa | 1566 |

<210> SEQ ID NO 6
<211> LENGTH: 1554
<212> TYPE: DNA
<213> ORGANISM: Artificial
<220> FEATURE:
<223> OTHER INFORMATION: Chemically synthesized

<400> SEQUENCE: 6

| | | | | | |
|---|---|---|---|---|---|
| atggcgctac | cggtgaccgc | actcctgctg | ccactcgccc | tcctgctcca | cgccgcccgc | 60 |
| cccgatatcc | agctgaccca | atcaccgtcg | tccctgtctg | cctccgtggg | cgaccgggtg | 120 |
| acgatcacct | gtagtgcctc | gagcagtgta | cggttcatcc | actggtacca | acagaagccc | 180 |
| ggcaaggcac | caaagcggct | gatctacgac | accagcaagc | tggcgtctgg | ggtgcccagc | 240 |
| aggttctcgg | gaagtggtag | tggcacagac | ttcactctca | ccatcagttc | actccagccg | 300 |
| gaggactttg | ccacctacta | ttgccagcag | tggtcctcgt | cccccttac | cttcggccag | 360 |
| ggaacaaagg | tggaaattaa | gggttcgacc | tccggggggg | gctccggtgg | gggctccggc | 420 |
| ggggggggct | catcggaggt | tcagctggtg | gagagcggcg | gcggcctggt | gcagcccggc | 480 |
| gggagtctgc | ggctgtcctg | tgccgccagc | ggcttcaaca | tcaaggacta | ctacattcac | 540 |
| tgggtgcggc | aagccccagg | caagggtctg | gagtgggtgg | cttggattga | ccctgaaaac | 600 |
| ggcgacactg | agttcgtgcc | aaaattccag | gggcgggcga | ccatctccgc | cgacacctcc | 660 |
| aagaatacgg | cctacctgca | gatgaactcc | ctgcgcgccg | aagacacagc | ggtctactac | 720 |
| tgcaagacag | ggggttttctg | gggccagggc | accctcgtga | ccgtttcgag | tgccgccggc | 780 |
| ggaggtggtg | gatccgatat | caaactgcag | cagtcagggg | ctgaactggc | aagacctggg | 840 |
| gcctcagtga | agatgtcctg | caagacttct | ggctacacct | ttactaggta | cacgatgcac | 900 |
| tgggtaaaac | agaggcctgg | acagggtctg | aatggattg | gatacattaa | tcctagccgt | 960 |
| ggttatacta | attacaatca | gaagttcaag | gacaaggcca | cattgactac | agacaaatcc | 1020 |
| tccagcacag | cctacatgca | actgagcagc | ctgacatctg | aggactctgc | agtctattac | 1080 |
| tgtgcaagat | attatgatga | tcattactgc | cttgactact | ggggccaagg | caccactctc | 1140 |
| acagtctcct | cagtcgaagg | tggaagtgga | ggttctggtg | aagtggagg | ttcaggtgga | 1200 |
| gtcgacgacg | ccgccattca | gctgacccag | tctccagcaa | tcatgtctgc | atctccaggg | 1260 |
| gagaaggtca | ccatgacctg | cagagccagt | tcaagtgtaa | gttacatgaa | ctggtaccag | 1320 |
| cagaagtcag | gcacctcccc | caaaagatgg | atttatgaca | catccaaagt | ggcttctgga | 1380 |
| gtcccttatc | gcttcagtgg | cagtgggtct | gggacctcat | actctctcac | aatcagcagc | 1440 |
| atggaggctg | aagatgctgc | cacttattac | tgccaacagt | ggagtagtaa | cccgctcacg | 1500 |
| ttcggtgctg | ggaccaagct | ggagctgaaa | catcatcacc | atcatcatta | ataa | 1554 |

<210> SEQ ID NO 7
<211> LENGTH: 1605
<212> TYPE: DNA
<213> ORGANISM: Artificial
<220> FEATURE:
<223> OTHER INFORMATION: Chemically synthesized

<400> SEQUENCE: 7

| | | | | | |
|---|---|---|---|---|---|
| atggagtttg | ggctgagctg | cttttttctt | gtggctattt | taaaggtgt | ccagtgctct | 60 |
| agagatattt | tgctgaccca | aactccactc | tccctgcctg | tcagtcttgg | agatcaagcc | 120 |
| tccatctctt | gcagatctag | tcagagtctt | gtacaccgta | atggaaacac | ctatttacat | 180 |
| tggtacctgc | agaagccagg | ccagtctcca | aagctcctga | ttcacaaagt | ttccaaccga | 240 |

| | |
|---|---|
| ttttctgggg tcccagacag gttcagtggc agtggatcag ggacagattt cacactcaag | 300 |
| atcagcagag tggaggctga ggatctggga gtttatttct gttctcaaag tacacatgtt | 360 |
| cctccgctca cgttcggtgc tgggaccaag ctggagctga acgggctga tgctgcacca | 420 |
| actgtatcca tcttcccagg ctcgggcggt ggtgggtcgg gtggcgaggt gaagcttcag | 480 |
| cagtctggac ctagcctggt ggagcctggc gcttcagtga tgatatcctg caaggcttct | 540 |
| ggttcctcat tcactggcta caacatgaac tgggtgaggc agaacattgg aaagagcctt | 600 |
| gaatggattg gagctattga tccttactat ggtggaacta gctacaacca gaagttcaag | 660 |
| ggcagggcca cattgactgt agacaaatcg tccagcacag cctacatgca cctcaagagc | 720 |
| ctgacatctg aggactctgc agtctattac tgtgtaagcg gaatggagta ctggggtcaa | 780 |
| ggaacctcag tcaccgtctc ctcagccaaa acgacacccc catcagtcta tggaggtggt | 840 |
| ggatccgata tcaaactgca gcagtcaggg gctgaactgg caagacctgg ggcctcagtg | 900 |
| aagatgtcct gcaagacttc tggctacacc tttactaggt acacgatgca ctgggtaaaa | 960 |
| cagaggcctg gacagggtct ggaatggatt ggatacatta atcctagccg tggttatact | 1020 |
| aattacaatc agaagttcaa ggacaaggcc acattgacta cagacaaatc ctccagcaca | 1080 |
| gcctacatgc aactgagcag cctgacatct gaggactctg cagtctatta ctgtgcaaga | 1140 |
| tattatgatg atcattactg ccttgactac tggggccaag gcaccactct cacagtctcc | 1200 |
| tcagtcgaag gtggaagtgg aggttctggt ggaagtggag gttcaggtgg agtcgacgac | 1260 |
| gccgccattc agctgaccca gtctccagca atcatgtctg catctccagg ggagaaggtc | 1320 |
| accatgacct gcagagccag ttcaagtgta agttacatga actggtacca gcagaagtca | 1380 |
| ggcacctccc ccaaaagatg gatttatgac acatccaaag tggcttctgg agtcccttat | 1440 |
| cgcttcagtg gcagtgggtc tgggacctca tactctctca caatcagcag catggaggct | 1500 |
| gaagatgctg ccacttatta ctgccaacag tggagtagta cccgctcac gttcggtgct | 1560 |
| gggaccaagc tggagctgaa acatcatcac catcatcatt aataa | 1605 |

<210> SEQ ID NO 8
<211> LENGTH: 1525
<212> TYPE: DNA
<213> ORGANISM: Artificial
<220> FEATURE:
<223> OTHER INFORMATION: Chemically synthesized

<400> SEQUENCE: 8

| | |
|---|---|
| atgggctggt cttgcatcat cctgttcctc gtggccaccg ccaccggcgt ccacagcgcc | 60 |
| atccagctca cccagagccc ctcgagcttg agtgcctcgg tgggagaccg ggtcactatc | 120 |
| acctgccgag ccagtcaggg catctcctcc gcccttgcct ggtaccagca gaagcccggg | 180 |
| aaggccccca agctgctgat ctacgacgct agtagtctgg agagtggcgt gccttcgcgc | 240 |
| ttctcgggca gtgggagtgg caccgacttc accttgacca tctccagtct acagccggaa | 300 |
| gatttcgcga cctactactg tcagcaattc aactcttatc catacacttt cggccagggg | 360 |
| acaaagctgg agatcaaggg cggggggcggg agtggcggcg gagggtccgg aggcgggggc | 420 |
| tccgaggtgc aactagtcca gagcggagcc gaggtgaaga gcccggggga gagtctaaag | 480 |
| atctcttgca agggctccgg ttactccttc tcgagttcct ggatcgggtg ggtgcgacag | 540 |
| atgccgggca agggcctgga gtggatgggc attatctacc ccgacgactc cgataccgt | 600 |
| tatagtccat cgttccaggg acaggtgacc atttccgccg acaagtctat cagaaccgcc | 660 |
| tatctgcagt ggtccagtct gaaggcctct gacactgcca tgtattattg cgccaggcac | 720 |

| | |
|---|---|
| gttacgatga tctgggggt gatcatcgac ttctggggcc agggcacact cgtaaccgtc | 780 |
| agttcggagg tggtggatcc caggtgcagc tcgtggagtc cggcggcggc gttgtccagc | 840 |
| ctggccgctc gctgcgcctg tcatgcgccg cttcgggttt cacgttcagg tcgtacggga | 900 |
| tgcactgggt caggcaggcg ccgggaaaag gcctggagtg ggtggctatc atctggtacg | 960 |
| acggctccaa gaagaattat gctgactccg tcaagggacg gttcacaatc tcgcgtgata | 1020 |
| actcgaagaa caccctctac ctgcagatga attccctcag agccgaagac acagccgtgt | 1080 |
| attattgcgc caggggcacc ggctataact ggttcgatcc atggggccag ggacccctgg | 1140 |
| ttaccgtctc ctccggaggg gggggtagtg agatcgtgct gacccagtcg cctcgcaccc | 1200 |
| tgtccctgtc ccctggggag cgcgccaccc tctcgtgcag ggcatcgcag tccgtcagtt | 1260 |
| cctcctatct ggcctggtac cagcagaaac ctggccaggc accaaggctg ctgatctacg | 1320 |
| gagcttcctc gagggcaacc gggatccccg acagattttc cggaagcgga agtggcacag | 1380 |
| acttcaccct gaccatcagt aggcttgacc ccgaagattt cgccgtgtac tattgccagc | 1440 |
| agtacggctc ctcccccatc accttcggcc agggcacaag actggagatc aagcaccatc | 1500 |
| accaccacca ctaataagcg gccgc | 1525 |

<210> SEQ ID NO 9
<211> LENGTH: 1519
<212> TYPE: DNA
<213> ORGANISM: Artificial
<220> FEATURE:
<223> OTHER INFORMATION: Chemically synthesized

<400> SEQUENCE: 9

| | |
|---|---|
| atgggctggt cttgcatcat cctgttcctc gtggccaccg ccaccggcgt ccacagcgcc | 60 |
| atccagctca cccagagccc ctcgagcttg agtgcctcgg tgggagaccg ggtcactatc | 120 |
| acctgccgag ccagtcaggg catctcctcc gcccttgcct ggtaccagca gaagcccggg | 180 |
| aaggccccca agctgctgat ctacgacgct agtagtctgg agagtggcgt gccttcgcgc | 240 |
| ttctcgggca gtgggagtgg caccgacttc accttgacca tctccagtct acagccggaa | 300 |
| gatttcgcga cctactactg tcagcaattc aactcttatc catacacttt cggccagggg | 360 |
| acaaagctgg agatcaaggg cggggcgggc agtggcggcg gagggtccgg aggcggggc | 420 |
| tccgaggtgc aactagtcca gagcggagcc gaggtgaaga gcccgggga gagtctaaag | 480 |
| atctcttgca agggctccgg ttactccttc tcgagttcct ggatcgggtg ggtgcgacag | 540 |
| atgccgggca agggcctgga gtggatgggc attatctacc ccgacgactc cgataccgt | 600 |
| tatagtccat cgttccaggg acaggtgacc atttccgccg acaagtctat cagaaccgcc | 660 |
| tatctgcagt ggtccagtct gaaggcctct gacactgcca tgtattattg cgccaggcac | 720 |
| gttacgatga tctgggggt gatcatcgac ttctggggcc agggcacact cgtaaccgtc | 780 |
| agttcggagg tggtggatcc caggtacagc tggtcgagtc cggtggggc gtggtccagc | 840 |
| ccggccggtc cctgcgcctg tcgtgcgctg cctccggctt taccttccgg tcgtatggca | 900 |
| tgcattgggt gcgccaggcc cccgggaagg gctggagtg gtcgccatt atctggtacg | 960 |
| atggctccaa gaagaactac gctgattcgg ttaaggccg cttcaccatt agtcgggata | 1020 |
| attcgaagaa tacgctgtat ctccagatga actccctgag ggccgaggac actgccgtgt | 1080 |
| actactgcgc ccggggcaca ggctataact ggttcgatcc ctggggtcag gcaccctag | 1140 |
| tgaccgtctc gtctggggc ggagggtcag atattctcat gacacagtcg ccctctagtc | 1200 |
| tttccgcctc cgtggggac cgcgtgacca tcacatgcag agcttcccag gggatctcct | 1260 |

| | |
|---|---|
| ctgcgctggc ctggtatcag cagaagcccg ggaaggcacc caagctgctc atctattacg | 1320 |
| cttcttcgct gcaaagtggg gtgccgtccc gcttctccgg aagcggctcc ggcacggact | 1380 |
| acaccctcac catctcctcc ctgcagcctg aggatttcgc cacctattac tgccagcagt | 1440 |
| attactccac gctgaccttc ggaggaggca cgaaagtgga gatcaagcac caccaccacc | 1500 |
| accactaata agcggccgc | 1519 |

<210> SEQ ID NO 10
<211> LENGTH: 1517
<212> TYPE: DNA
<213> ORGANISM: Artificial
<220> FEATURE:
<223> OTHER INFORMATION: Chemically synthesized

<400> SEQUENCE: 10

| | |
|---|---|
| atgggctggt cttgcatcat cctgttcctc gtggccaccg ccaccggcgt ccacagcgcc | 60 |
| atccagctca cccagagccc ctcgagcttg agtgcctcgg tgggagaccg ggtcactatc | 120 |
| acctgccgag ccagtcaggg catctcctcc gcccttgcct ggtaccagca gaagcccggg | 180 |
| aaggccccca gctgctgat ctacgacgct agtagtctgg agagtggcgt gccttcgcgc | 240 |
| ttctcgggca gtgggagtgg caccgacttc accttgacca tctccagtct acagccggaa | 300 |
| gatttcgcga cctactactg tcagcaattc aactcttatc catacacttt cggccagggg | 360 |
| acaaagctgg agatcaaggg cggggcgggg agtggcggcg agggtccgg aggcgggggc | 420 |
| tccgaggtgc aactagtcca gagcggagcc gaggtgaaga gcccgggga gagtctaaag | 480 |
| atctcttgca agggctccgg ttactccttc tcgagttcct ggatcgggtg ggtgcgacag | 540 |
| atgccgggca agggcctgga gtggatgggc attatctacc ccgacgactc cgataccgt | 600 |
| tatagtccat cgttccaggg acaggtgacc atttccgccg acaagtctat cagaaccgcc | 660 |
| tatctgcagt ggtccagtct gaaggcctct gacactgcca tgtattattg cgccaggcac | 720 |
| gttacgatga tctgggggt gatcatcgac ttctggggcc agggcacact cgtaaccgtc | 780 |
| agttcggagg tggtggatcc caggtccagc tggttgagtc tggtggcgga gtggtccagc | 840 |
| ccggccggtc tctccgcctg tcctgcgccg cttccgggtt caagttctcc ggctacggaa | 900 |
| tgcactgggt gaggcaggcg ccaggtaagg ggctcgagtg ggtcgcggtg atatggtatg | 960 |
| acggtagcaa gaagtattac gtggacagtg tgaaaggccg ctttaccatc tcacgcgaca | 1020 |
| attctaagaa caccctgtac ctccagatga actccctgcg cgctgaggac acggcggtgt | 1080 |
| actactgcgc taggcagatg gggtactggc acttcgacct ttggggcagg gtaccctgg | 1140 |
| tgaccgtctc atccggcggc ggcgggtctg agatcgttct gacccaaagt ccggccacac | 1200 |
| tgtccctctc cccaggagag cgcgctacgc ttagctgccg cgcctcccag agcgtgtcct | 1260 |
| cctacctggc atggtatcag cagaagccgg ggcaggcgcc tcgactgctg atctacgacg | 1320 |
| cctcgaaccg cgcgacaggt atccccgcgc gcttcagcgg ctccggttcg gggactgatt | 1380 |
| tcaccctgac catctcctcc ctcgagcctg aggatttcgc agtgtactac tgccagcaga | 1440 |
| gatccaattg gccccccctc accttcggcg ggggaaccaa ggtggagatc aagcaccacc | 1500 |
| accaccatca ctaataa | 1517 |

<210> SEQ ID NO 11
<211> LENGTH: 1522
<212> TYPE: DNA
<213> ORGANISM: Artificial
<220> FEATURE:
<223> OTHER INFORMATION: Chemically synthesized

<400> SEQUENCE: 11

```
atgggctggt cttgcatcat cctgttcctc gtggccaccg ccaccggcgt ccacagcgcc      60
atccagctca cccagagccc ctcgagcttg agtgcctcgg tgggagaccg ggtcactatc     120
acctgccgag ccagtcaggg catctcctcc gcccttgcct ggtaccagca gaagcccggg     180
aaggccccca agctgctgat ctacgacgct agtagtctgg agagtggcgt gccttcgcgc     240
ttctcgggca gtgggagtgg caccgacttc accttgacca tctccagtct acagccggaa     300
gatttcgcga cctactactg tcagcaattc aactcttatc catacacttt cggccagggg     360
acaaagctgg agatcaaggg cggggcgggg agtggcggcg agggtccgg aggcggggc      420
tccgaggtgc aactagtcca gagcggagcc gaggtgaaga gcccgggga gagtctaaag     480
atctcttgca agggctccgg ttactccttc tcgagttcct ggatcgggtg ggtgcgacag     540
atgccgggca agggcctgga gtggatgggc attatctacc ccgacgactc cgataccgt     600
tatagtccat cgttccaggg acaggtgacc atttccgccg acaagtctat cagaaccgcc     660
tatctgcagt ggtccagtct gaaggcctct gacactgcca tgtattattg cgccaggcac     720
gttacgatga tctgggggt gatcatcgac ttctggggcc agggcacact cgtaaccgtc     780
agttcggagg tggtggatcc caggttcagc tggtgcagtc cggcgccgag gtgaagaagc     840
cgggcgcttc tgtgaaggtc agctgtaaag ccagtggcta cacattcacc aggtacacta     900
tgcactgggt gcgccaggca cccgggcagg gctggaatg gatcgggtac atcaatcctt     960
cccgcggtta ctaactat aatcaaaagt tcaaagaccg cgtgacaatt acgaccgata    1020
agagttcatc caccgcttac ttacagatga actccctcaa gacagaggac accgccgtgt    1080
actactgtgc ccgctactac gacgaccatt actgcctgga ctactggggc caggggacca    1140
ccgtaaccgt cagtagtggc gggggcggca gtcagatcgt gctgacccag agtccggcga    1200
ccctgagtct gtctcctggt gagcgcgcaa cgctgacgtg ctcagcctcc tcgagtgcct    1260
cttatatgaa ctggtaccag cagaagcccg gcaaggcccc taagcgctgg atctacgaca    1320
cctcgaagct agcttcgggc gtcccctccc ggttctcggg ctcggggtcg gcacggact     1380
attctctgac catcaacagt ctggaggcag aggacgccgc aacctactac tgccagcagt    1440
ggagttcgaa tccttttcacg tttgggcagg ggaccaaggt ggaaatcaaa caccatcacc    1500
accatcacta taagcggcc gc                                              1522
```

<210> SEQ ID NO 12
<211> LENGTH: 1522
<212> TYPE: DNA
<213> ORGANISM: Artificial
<220> FEATURE:
<223> OTHER INFORMATION: Chemically synthesized

<400> SEQUENCE: 12

```
atgggctggt cttgcatcat cctgttcctc gtggccaccg ccaccggcgt ccacagcgcc      60
atccagctca cccagagccc ctcgagcttg agtgcctcgg tgggagaccg ggtcactatc     120
acctgccgag ccagtcaggg catctcctcc gcccttgcct ggtaccagca gaagcccggg     180
aaggccccca agctgctgat ctacgacgct agtagtctgg agagtggcgt gccttcgcgc     240
ttctcgggca gtgggagtgg caccgacttc accttgacca tctccagtct acagccggaa     300
gatttcgcga cctactactg tcagcaattc aactcttatc catacacttt cggccagggg     360
acaaagctgg agatcaaggg cggggcgggg agtggcggcg agggtccgg aggcggggc      420
tccgaggtgc aactagtcca gagcggagcc gaggtgaaga gcccgggga gagtctaaag     480
```

```
atctcttgca agggctccgg ttactccttc tcgagttcct ggatcgggtg ggtgcgacag    540
atgccgggca agggcctgga gtggatgggc attatctacc ccgacgactc cgatacccgt    600
tatagtccat cgttccaggg acaggtgacc atttccgccg acaagtctat cagaaccgcc    660
tatctgcagt ggtccagtct gaaggcctct gacactgcca tgtattattg cgccaggcac    720
gttacgatga tctggggggt gatcatcgac ttctggggcc agggcacact cgtaaccgtc    780
agttcggagg tggtggatcc caggttcagc tggtgcagtc cggcgccgag gtgaagaagc    840
cgggcgcttc tgtgaaggtc agctgtaaag ccagtggcta cattcacc aggtacacta    900 tgcactgggt cgccaggca cccgggcagg gctggaatg gatcgggtac atcaatcctt    960
cccgcggtta tactaactat gctcaaaagt tccaagaccg cgtgacaatt acgaccgata   1020
agagttcatc caccgcttac ttacagatga actccctcaa gacagaggac accgccgtgt   1080
actactgtgc ccgctactac gacgaccatt actgcctgga ctactgggggc aggggacca   1140 ccgtaaccgt cagtagtggc ggggggcggca gtcagatcgt gctgacccag agtccggcga   1200
ccctgagtct gtctcctggt gagcgcgcaa cgctgacgtg ctcagcctcc tcgagtgcct   1260
cttatatgaa ctggtaccag cagaagcccg gcaaggcccc taagcgctgg atctacgaca   1320
cctcgaagct agcttcgggc gtcccctccc ggttctcggg ctcggggtcg ggcacggact   1380
attctctgac catcaacagt ctggaggcag aggacgccgc aacctactac tgccagcagt   1440
ggagttcgaa tccttcacg tttgggcagg ggaccaaggt ggaaatcaaa caccatcacc   1500
accatcacta ataagcggcc gc                                            1522

<210> SEQ ID NO 13
<211> LENGTH: 1522
<212> TYPE: DNA
<213> ORGANISM: Artificial
<220> FEATURE:
<223> OTHER INFORMATION: Chemically synthesized

<400> SEQUENCE: 13
atgggctggt cttgcatcat cctgttcctc gtggccaccg ccaccggcgt ccacagcgcc     60
atccagctca cccagagccc ctcgagcttg agtgcctcgg tgggagaccg ggtcactatc    120
acctgccgag ccagtcaggg catctcctcc gcccttgcct ggtaccagca gaagcccggg    180
aaggccccca agctgctgat ctacgacgct agtagtctgg agagtggcgt gccttcgcgc    240
ttctcgggca gtgggagtgg caccgacttc accttgacca tctccagtct acagccggaa    300
gatttcgcga cctactactg tcagcaattc aactcttatc catacacttt cggccagggg    360
acaaagctgg agatcaaggg cgggggcggg agtggcggcg agggtccgg aggcggggc    420 tccgaggtgc aactagtcca gagcggagcc gaggtgaaga agcccgggga gagtctaaag    480
atctcttgca agggctccgg ttactccttc tcgagttcct ggatcgggtg ggtgcgacag    540
atgccgggca agggcctgga gtggatgggc attatctacc ccgacgactc cgatacccgt    600
tatagtccat cgttccaggg acaggtgacc atttccgccg acaagtctat cagaaccgcc    660
tatctgcagt ggtccagtct gaaggcctct gacactgcca tgtattattg cgccaggcac    720
gttacgatga tctggggggt gatcatcgac ttctggggcc agggcacact cgtaaccgtc    780
agttcggagg tggtggatcc caggttcagc tggtgcagtc cggcgccgag gtgaagaagc    840
cgggcgcttc tgtgaaggtc agctgtaaag ccagtggcta cattcacc aggtacacta    900 tgcactgggt cgccaggca cccgggcagg gctggaatg gatcgggtac atcaatcctt    960
cccgcggtta tactaactat aatcaaaagg tcaaagaccg cttgacaatt acgaccgata   1020
```

```
agagttcatc caccgcttac ttacagatga actccctcaa gacagaggac accgccgtgt    1080
actactgtgc ccgctactac gacgaccatt actgcctgga ctactggggc caggggacca    1140
ccgtaaccgt cagtagtggc gggggcggca gtcagatcgt gctgacccag agtccggcga    1200
ccctgagtct gtctcctggt gagcgcgcaa cgctgacgtg ctcagcctcc tcgagtgcct    1260
cttatatgaa ctggtaccag cagaagcccg gcaaggcccc taagcgctgg atctacgaca    1320
cctcgaagct agcttcgggc gtccctccc ggttctcggg ctcggggtcg ggcacggact    1380
attctctgac catcaacagt ctggaggcag aggacgccgc aacctactac tgccagcagt    1440
ggagttcgaa tccttttcacg tttgggcagg ggaccaaggt ggaaatcaaa caccatcacc    1500
accatcacta taagcggcc gc                                              1522
```

<210> SEQ ID NO 14
<211> LENGTH: 1571
<212> TYPE: DNA
<213> ORGANISM: Artificial
<220> FEATURE:
<223> OTHER INFORMATION: Chemically synthesized

<400> SEQUENCE: 14

```
atgggatgga gctgtatcat cctcttcttg gtagcaacag ctacaggtgt ccactccgac     60
tacaaagatg atgacgataa ggatatccag ctgacccagt ctccagcttc tttggctgtg    120
tctctagggc agagggccac catctcctgc aaggccagcc aaagtgttga ttatgatggt    180
gatagttatt tgaactggta ccaacagatt ccaggacagc cacccaaact cctcatctat    240
gatgcatcca atctagtttc tgggatccca cccaggttta gtggcagtgg gtctgggaca    300
gacttcaccc tcaacatcca tcctgtggag aaggtggatg ctgcaaccta tcactgtcag    360
caaagtactg aggatccgtg gacgttcggt ggagggacca agctcgagat caaaggtggt    420
ggtggttctg gcggcggcgg ctccggtggt ggtggttctc aggtgcagct gcagcagtct    480
ggggctgagc tggtgaggcc tggtcctca gtgaagattt cctgcaaggc ttctggctat    540
gcattcagta gctactggat gaactgggtg aagcagaggc ctggacaggg tcttgagtgg    600
attggacaga tttggcctgg agatggtgat actaactaca atgaaagtt caagggtaaa    660 gccactctga ctgcagacga atcctccagc acagcctaca tgcaactcag cagcctagca    720
tctgaggact ctgcggtcta ttctgtgca agacgggaga ctacgacggt aggccgttat    780
tactatgcta tggactactg gggccaaggg accacggtca ccgtctcctc cggaggtggt    840
ggatcccagg tgcagctcgt ggagtccggc ggcggcgttg tccagcctgg ccgctcgctg    900
cgcctgtcat gcgccgcttc gggtttcacg ttcaggtcgt acgggatgca ctgggtcagg    960
caggcgccgg gaaaaggcct ggagtgggtg gctatcatct ggtacgacgg ctccaagaag   1020
aattatgctg actccgtcaa gggacggttc acaatctcgc gtgataactc gaagaacacc   1080
ctctacctgc agatgaattc cctcagagcc gaagacacag ccgtgtatta ttgcgccagg   1140
ggcaccggct ataactggtt cgatccatgg ggccagggga ccctggttac cgtctcctcc   1200
ggaggggggg gtagtgagat cgtgctgacc cagtcgcctc gcaccctgtc cctgtcccct   1260
ggggagcgcg ccaccctctc gtgcagggca tcgcagtccg tcagttcctc ctatctggcc   1320
tggtaccagc agaaacctgg ccaggcacca aggctgctga tctacggagc ttcctcgagg   1380
gcaacccgga tccccgacag attttccgga agcggaagtg gcacagactt caccctgacc   1440
atcagtaggc ttgaccccga agatttcgcc gtgtactatt gccagcagta cggctcctcc   1500
```
cccatcacct tcggccaggg cacaagactg gagatcaagc accatcacca ccaccactaa    1560
taagcggccg c                                                         1571

<210> SEQ ID NO 15
<211> LENGTH: 1565
<212> TYPE: DNA
<213> ORGANISM: Artificial
<220> FEATURE:
<223> OTHER INFORMATION: Chemically synthesized

<400> SEQUENCE: 15
atgggatgga gctgtatcat cctcttcttg gtagcaacag ctacaggtgt ccactccgac      60
tacaaagatg atgacgataa ggatatccag ctgacccagt ctccagcttc tttggctgtg     120
tctctagggc agagggccac catctcctgc aaggccagcc aaagtgttga ttatgatggt     180
gatagttatt tgaactggta ccaacagatt ccaggacagc acccaaaact cctcatctat     240
gatgcatcca atctagtttc tgggatccca ccaggtttta gtggcagtgg gtctgggaca     300
gacttcaccc tcaacatcca tcctgtggag aaggtggatg ctgcaaccta tcactgtcag     360
caaagtactg aggatccgtg gacgttcggt ggagggacca agctcgagat caaaggtggt     420
ggtggttctg gcggcggcgg ctccggtggt ggtggttctc aggtgcagct gcagcagtct     480
ggggctgagc tggtgaggcc tgggtcctca gtgaagattt cctgcaaggc ttctggctat     540
gcattcagta gctactggat gaactgggtg aagcagaggc ctggacaggg tcttgagtgg     600
attggacaga tttggcctgg agatggtgat actaactaca atggaaagtt caagggtaaa     660
gccactctga ctgcagacga atcctccagc acagcctaca tgcaactcag cagcctagca     720
tctgaggact ctgcggtcta tttctgtgca agacgggaga ctacgacggt aggccgttat     780
tactatgcta tggactactg gggccaaggg accacggtca ccgtctcctc cggaggtggt     840
ggatcccagg tacagctggt cgagtccggt gggggcgtgg tccagcccgg ccggtccctg     900
cgcctgtcgt gcgctgcctc cggctttacc ttccggtcgt atggcatgca ttgggtcgcc     960
caggcccccg ggaaggggct ggagtgggtc gccattatct ggtacgatgg ctccaagaag    1020
aactacgctg attcggttaa gggccgcttc accattagtc gggataattc gaagaatacg    1080
ctgtatctcc agatgaactc cctgagggcc gaggacactg ccgtgtacta ctgcgcccgg    1140
ggcacaggct ataactggtt cgatccctgg ggtcagggca ccctagtgac cgtctcgtct    1200
gggggcggag ggtcagatat tctcatgaca cagtcgccct ctagtctttc cgcctccgtg    1260
ggggaccgcg tgaccatcac atgcagagct cccaggggga tctcctctgc gctggcctgg    1320
tatcagcaga gcccgggaa ggcacccaag ctgctcatct attacgcttc ttcgctgcaa    1380
agtggggtgc cgtcccgctt ctccggaagc ggctccggca cggactacac cctcaccatc    1440
tcctccctgc agcctgagga tttcgccacc tattactgcc agcagtatta ctccacgctg    1500
accttcggag gaggcacgaa agtggagatc aagcaccacc accaccacca ctaataagcg    1560
gccgc                                                                1565

<210> SEQ ID NO 16
<211> LENGTH: 1563
<212> TYPE: DNA
<213> ORGANISM: Artificial
<220> FEATURE:
<223> OTHER INFORMATION: Chemically synthesized

<400> SEQUENCE: 16

```
atgggatgga gctgtatcat cctcttcttg gtagcaacag ctacaggtgt ccactccgac      60
tacaaagatg atgacgataa ggatatccag ctgacccagt ctccagcttc tttggctgtg     120
tctctagggc agagggccac catctcctgc aaggccagcc aaagtgttga ttatgatggt     180
gatagttatt tgaactggta ccaacagatt ccaggacagc cacccaaact cctcatctat     240
gatgcatcca atctagtttc tgggatccca cccaggttta gtggcagtgg gtctgggaca     300
gacttcaccc tcaacatcca tcctgtggag aaggtggatg ctgcaaccta tcactgtcag     360
caaagtactg aggatccgtg gacgttcggt ggagggacca agctcgagat caaaggtggt     420
ggtggttctg gcggcggcgg ctccggtggt ggtggttctc aggtgcagct gcagcagtct     480
ggggctgagc tggtgaggcc tgggtcctca gtgaagattt cctgcaaggc ttctggctat     540
gcattcagta gctactggat gaactgggtg aagcagaggc ctgacagggg tcttgagtgg     600
attggacaga tttggcctgg agatggtgat actaactaca atggaaagtt caagggtaaa     660
gccactctga ctgcagacga atcctccagc acagcctaca tgcaactcag cagcctagca     720
tctgaggact ctgcggtcta tttctgtgca gacggagaa ctacgacggt aggccgttat     780
tactatgcta tggactactg gggccaaggg accacggtca ccgtctcctc cggaggtggt     840
ggatcccagg tccagctggt tgagtctggt ggcggagtgg tccagcccgg ccggtctctc     900
cgcctgtcct gcgccgcttc cgggttcaag ttctccggct acggaatgca ctgggtgagg     960
caggcgccag gtaaggggct cgagtgggtc gcggtgatat ggtatgacgg tagcaagaag    1020
tattacgtgg acagtgtgaa aggccgcttt accatctcac gcgacaattc taagaacacc    1080
ctgtacctcc agatgaactc cctgcgcgct gaggacacgg cggtgtacta ctgcgctagg    1140
cagatggggt actggcactt cgacctttgg gcagggggta ccctggtgac cgtctcatcc    1200
ggcggcggcg ggtctgagat cgttctgacc caaagtccgg ccacactgtc cctctcccca    1260
ggagagcgcg ctacgcttag ctgccgcgcc tcccagagcg tgtcctccta cctggcatgg    1320
tatcagcaga agccggggca ggcgcctcga ctgctgatct acgacgcctc gaaccgcgcg    1380
acaggtatcc ccgcgcgctt cagcggctcc ggttcgggga ctgatttcac cctgaccatc    1440
tcctccctcg agcctgagga tttcgcagtg tactactgcc agcagagatc caattggccc    1500
cccctcacct tcggcggggg aaccaaggtg gagatcaagc accaccacca ccatcactaa    1560
taa                                                                 1563
```

<210> SEQ ID NO 17
<211> LENGTH: 1568
<212> TYPE: DNA
<213> ORGANISM: Artificial
<220> FEATURE:
<223> OTHER INFORMATION: Chemically synthesized

<400> SEQUENCE: 17

```
atgggatgga gctgtatcat cctcttcttg gtagcaacag ctacaggtgt ccactccgac      60
tacaaagatg atgacgataa ggatatccag ctgacccagt ctccagcttc tttggctgtg     120
tctctagggc agagggccac catctcctgc aaggccagcc aaagtgttga ttatgatggt     180
gatagttatt tgaactggta ccaacagatt ccaggacagc cacccaaact cctcatctat     240
gatgcatcca atctagtttc tgggatccca cccaggttta gtggcagtgg gtctgggaca     300
gacttcaccc tcaacatcca tcctgtggag aaggtggatg ctgcaaccta tcactgtcag     360
caaagtactg aggatccgtg gacgttcggt ggagggacca agctcgagat caaaggtggt     420
```

| | |
|---|---|
| ggtggttctg gcggcggcgg ctccggtggt ggtggttctc aggtgcagct gcagcagtct | 480 |
| ggggctgagc tggtgaggcc tgggtcctca gtgaagattt cctgcaaggc ttctggctat | 540 |
| gcattcagta gctactggat gaactgggtg aagcagaggc ctggacaggg tcttgagtgg | 600 |
| attggacaga tttggcctgg agatggtgat actaactaca tggaaagtt caagggtaaa | 660 |
| gccactctga ctgcagacga atcctccagc acagcctaca tgcaactcag cagcctagca | 720 |
| tctgaggact ctgcggtcta tttctgtgca agacgggaga ctacgacggt aggccgttat | 780 |
| tactatgcta tggactactg ggccaagggg accacggtca ccgtctcctc cggaggtggt | 840 |
| ggatcccagg ttcagctggt gcagtccggc gccgaggtga agaagccggg cgcttctgtg | 900 |
| aaggtcagct gtaaagccag tggctacaca ttcaccaggt acactatgca ctgggtgcgc | 960 |
| caggcacccg gcaggggct ggaatggatc gggtacatca atcctcccg cggttatact | 1020 |
| aactataatc aaaagttcaa agaccgcgtg acaattacga ccgataagag ttcatccacc | 1080 |
| gcttacttac agatgaactc cctcaagaca gaggacaccg ccgtgtacta ctgtgcccgc | 1140 |
| tactacgacg accattactg cctggactac tggggccagg gaccaccgt aaccgtcagt | 1200 |
| agtggcgggg gcggcagtca gatcgtgctg acccagagtc cggcgaccct gagtctgtct | 1260 |
| cctggtgagc gcgcaacgct gacgtgctca gcctcctcga gtgcctctta tatgaactgg | 1320 |
| taccagcaga agcccggcaa ggcccctaag cgctggatct acgacacctc gaagctagct | 1380 |
| tcgggcgtcc cctcccggtt ctcgggctcg ggtcgggca cggactattc tctgaccatc | 1440 |
| aacagtctgg aggcagagga cgccgcaacc tactactgcc agcagtggag ttcgaatcct | 1500 |
| ttcacgtttg gcaggggac caaggtggaa atcaaacacc atcaccacca tcactaataa | 1560 |
| gcggccgc | 1568 |

<210> SEQ ID NO 18
<211> LENGTH: 1568
<212> TYPE: DNA
<213> ORGANISM: Artificial
<220> FEATURE:
<223> OTHER INFORMATION: Chemically synthesized

<400> SEQUENCE: 18

| | |
|---|---|
| atgggatgga gctgtatcat cctcttcttg gtagcaacag ctacaggtgt ccactccgac | 60 |
| tacaaagatg atgacgataa ggatatccag ctgacccagt ctccagcttc tttggctgtg | 120 |
| tctctagggc agagggccac catctcctgc aaggccagcc aaagtgttga ttatgatggt | 180 |
| gatagttatt tgaactggta ccaacagatt ccaggacagc acccaaaact cctcatctat | 240 |
| gatgcatcca atctagtttc tgggatccca cccaggttta gtggcagtgg gtctgggaca | 300 |
| gacttcaccc tcaacatcca tcctgtggag aaggtggatg ctgcaaccta tcactgtcag | 360 |
| caaagtactg aggatccgtg gacgttcggt ggagggacca agctcgagat caaaggtggt | 420 |
| ggtggttctg gcggcggcgg ctccggtggt ggtggttctc aggtgcagct gcagcagtct | 480 |
| ggggctgagc tggtgaggcc tgggtcctca gtgaagattt cctgcaaggc ttctggctat | 540 |
| gcattcagta gctactggat gaactgggtg aagcagaggc ctggacaggg tcttgagtgg | 600 |
| attggacaga tttggcctgg agatggtgat actaactaca tggaaagtt caagggtaaa | 660 |
| gccactctga ctgcagacga atcctccagc acagcctaca tgcaactcag cagcctagca | 720 |
| tctgaggact ctgcggtcta tttctgtgca agacgggaga ctacgacggt aggccgttat | 780 |
| tactatgcta tggactactg ggccaagggg accacggtca ccgtctcctc cggaggtggt | 840 |
| ggatcccagg ttcagctggt gcagtccggc gccgaggtga agaagccggg cgcttctgtg | 900 |

| | |
|---|---|
| aaggtcagct gtaaagccag tggctacaca ttcaccaggt acactatgca ctgggtgcgc | 960 |
| caggcacccg gcaggggct ggaatggatc gggtacatca atccttcccg cggttatact | 1020 |
| aactatgctc aaaagttcca agaccgcgtg acaattacga ccgataagag ttcatccacc | 1080 |
| gcttacttac agatgaactc cctcaagaca gaggacaccg ccgtgtacta ctgtgcccgc | 1140 |
| tactacgacg accattactg cctggactac tggggccagg gaccaccgt aaccgtcagt | 1200 |
| agtggcgggg gcggcagtca gatcgtgctg acccagagtc cggcgaccct gagtctgtct | 1260 |
| cctggtgagc gcgcaacgct gacgtgctca gcctcctcga gtgcctctta tatgaactgg | 1320 |
| taccagcaga agcccggcaa ggcccctaag cgctggatct acgacacctc gaagctagct | 1380 |
| tcgggcgtcc cctcccggtt ctcgggctcg ggtcgggca cggactattc tctgaccatc | 1440 |
| aacagtctgg aggcagagga cgccgcaacc tactactgcc agcagtggag ttcgaatcct | 1500 |
| ttcacgtttg gcaggggac caaggtggaa atcaaacacc atcaccacca tcactaataa | 1560 |
| gcggccgc | 1568 |

<210> SEQ ID NO 19
<211> LENGTH: 1568
<212> TYPE: DNA
<213> ORGANISM: Artificial
<220> FEATURE:
<223> OTHER INFORMATION: Chemically synthesized

<400> SEQUENCE: 19

| | |
|---|---|
| atgggatgga gctgtatcat cctcttcttg gtagcaacag ctacaggtgt ccactccgac | 60 |
| tacaaagatg atgacgataa ggatatccag ctgacccagt ctccagcttc tttggctgtg | 120 |
| tctctagggc agagggccac catctcctgc aaggccagcc aaagtgttga ttatgatggt | 180 |
| gatagttatt tgaactggta ccaacagatt ccaggacagc cacccaaact cctcatctat | 240 |
| gatgcatcca atctagtttc tgggatccca cccaggttta gtggcagtgg gtctgggaca | 300 |
| gacttcaccc tcaacatcca tcctgtggag aaggtggatg ctgcaaccta tcactgtcag | 360 |
| caaagtactg aggatccgtg gacgttcggt ggagggacca agctcgagat caaaggtggt | 420 |
| ggtggttctg gcggcggcgg ctccggtggt ggtggttctc aggtgcagct gcagcagtct | 480 |
| ggggctgagc tggtgaggcc tgggtcctca gtgaagattt cctgcaaggc ttctggctat | 540 |
| gcattcagta gctactggat gaactgggtg aagcagaggc ctggacaggg tcttgagtgg | 600 |
| attggacaga tttggcctgg agatggtgat actaactaca tggaaagtt caagggtaaa | 660 |
| gccactctga ctgcagacga atcctccagc acagcctaca tgcaactcag cagcctagca | 720 |
| tctgaggact ctgcggtcta tttctgtgca agacgggaga ctacgacggt aggccgttat | 780 |
| tactatgcta tggactactg gggccaaggg accacggtca ccgtctcctc cggaggtggt | 840 |
| ggatcccagg ttcagctggt gcagtccggc gccgaggtga agaagccggg cgcttctgtg | 900 |
| aaggtcagct gtaaagccag tggctacaca ttcaccaggt acactatgca ctgggtgcgc | 960 |
| caggcacccg gcaggggct ggaatggatc gggtacatca atccttcccg cggttatact | 1020 |
| aactataatc aaaaggtcaa agaccgcttg acaattacga ccgataagag ttcatccacc | 1080 |
| gcttacttac agatgaactc cctcaagaca gaggacaccg ccgtgtacta ctgtgcccgc | 1140 |
| tactacgacg accattactg cctggactac tggggccagg gaccaccgt aaccgtcagt | 1200 |
| agtggcgggg gcggcagtca gatcgtgctg acccagagtc cggcgaccct gagtctgtct | 1260 |
| cctggtgagc gcgcaacgct gacgtgctca gcctcctcga gtgcctctta tatgaactgg | 1320 |
| taccagcaga agcccggcaa ggcccctaag cgctggatct acgacacctc gaagctagct | 1380 |

| | |
|---|---|
| tcgggcgtcc cctcccggtt ctcgggctcg gggtcgggca cggactattc tctgaccatc | 1440 |
| aacagtctgg aggcagagga cgccgcaacc tactactgcc agcagtggag ttcgaatcct | 1500 |
| ttcacgtttg gcaggggac caaggtggaa atcaaacacc atcaccacca tcactaataa | 1560 |
| gcggccgc | 1568 |

<210> SEQ ID NO 20
<211> LENGTH: 1470
<212> TYPE: DNA
<213> ORGANISM: Artificial
<220> FEATURE:
<223> OTHER INFORMATION: Chemically synthesized

<400> SEQUENCE: 20

| | |
|---|---|
| atgggctggt cttgcatcat cctgttcctc gtggccaccg ccaccggcgt ccacagcgcc | 60 |
| atccagctca cccagagccc ctcgagcttg agtgcctcgg tgggagaccg ggtcactatc | 120 |
| acctgccgag ccagtcaggg catctcctcc gcccttgcct ggtaccagca gaagcccggg | 180 |
| aaggcccca agctgctgat ctacgacgct agtagtctgg agagtggcgt gccttcgcgc | 240 |
| ttctcgggca gtgggagtgg caccgacttc accttgacca tctccagtct acagccggaa | 300 |
| gatttcgcga cctactactg tcagcaattc aactcttatc catacacttt cggccagggg | 360 |
| acaaagctgg agatcaaggg cggggcggg agtggcggcg agggtccgg aggcggggc | 420 |
| tccgaggtgc aactagtcca gagcggagcc gaggtgaaga gcccgggga gagtctaaag | 480 |
| atctcttgca agggctccgg ttactccttc tcgagttcct ggatcgggtg ggtgcgacag | 540 |
| atgccgggca agggcctgga gtggatgggc attatctacc ccgacgactc cgatacccgt | 600 |
| tatagtccat cgttccaggg acaggtgacc atttccgccg acaagtctat cagaaccgcc | 660 |
| tatctgcagt ggtccagtct gaaggcctct gacactgcca tgtattattg cgccaggcac | 720 |
| gttacgatga tctgggggt gatcatcgac ttctggggcc agggcacact cgtaaccgtc | 780 |
| agttctgcgg ccgcaaccac gacgccagcg ccgcgaccac caacaccggc gcccaccatc | 840 |
| gcgtcgcagc ccctgtccct cgcccagag gcgtgccggc cagcggcggg gggcgcagtg | 900 |
| cacacgaggg ggctggactt cgcctgtgat atctacatct gggcgccctt ggccgggact | 960 |
| tgtgggtcc ttctcctgtc actggttatc acccttact gcaaacgggg cagaaagaaa | 1020 |
| ctcctgtata tattcaaaca accatttatg agaccagtac aaactactca agaggaagat | 1080 |
| ggctgtagct gccgatttcc agaagaagaa gaaggaggat gtgaactgag agtgaagttc | 1140 |
| agcaggagcg cagacgcccc cgcgtacaag cagggccaga accagctcta taacgagctc | 1200 |
| aatctaggac gaagagagga gtacgacgtt ttggacaaga cgtggccg ggaccctgag | 1260 |
| atgggggaa agccgagaag gaagaaccct caggaaggcc tgtacaatga actgcagaaa | 1320 |
| gataagatgg cggaggccta cagtgagatt gggatgaaag gcgagcgccg gaggggcaag | 1380 |
| gggcacgatg gcctttacca gggtctcagt acagccacca aggacaccta cgacgccctt | 1440 |
| cacatgcagg ccctgccccc tcgctaataa | 1470 |

<210> SEQ ID NO 21
<211> LENGTH: 1482
<212> TYPE: DNA
<213> ORGANISM: Artificial
<220> FEATURE:
<223> OTHER INFORMATION: Chemically synthesized

<400> SEQUENCE: 21

```
atggggtggt cgtgcatcat cctgtttctg gtggccacag caaccggcgt gcacagtgag    60
attgtgctga cccaaagccc ggacttccag tccgtgaccc ccaaggagaa ggttaccatc   120
acgtgccgcg cctctgaaag cgtggacacg ttcgggatct ccttcatgaa ttggtttcag   180
cagaagccag atcagtcacc caaactcctg atccacgccg ccagtaatca gggctcaggc   240
gtcccgtcca ggttctctgg cagtggctcc ggtactgact tcaccttaac catcaactct   300
ctggaggcag aggacgccgc cacatacttc tgccaacaga gcaaggaggt gcccttcacc   360
ttcggaggtg ggaccaaggt cgaaatcaag ggaggggggg gtccggcgg cggcggatcc    420
ggaggcggcg gcagcgaggt gcagctcgtc gagagtgggg gcggactggt gcaaccaggg   480
ggctctctgc ggctgagctg cgctgcctcc ggattcacat tctcctcgtc ctggatgaac   540
tgggttcgcc aggcccccgg caaaggcctg gagtgggtcg gcagaatcta cccaggcgac   600
ggggacacga actacaacgg caagttcaag ggccggttca caatctcgcg cgacgactca   660
aaaaacagcc tgtatctcca gatgaactcc ctgaaaaccg aggacaccgc cgtgtattac   720
tgtgcacgca gcggctttat caccaccgtt ctggacttcg attattgggg ccagggtacc   780
ctggtgacgg taagttcggc ggccgcaacc acgacgccag cgccgcgacc accaacaccg   840
gcgcccacca tcgcgtcgca gccccctgtc ctgcgcccag aggcgtgccg gccagcggcg   900
gggggcgcag tgcacacgag ggggctggac ttcgcctgtg atatctacat ctgggcgccc   960
ttggccggga cttgtggggt ccttctcctg tcactggtta tcaccccttta ctgcaaacgg  1020
ggcagaaaga aactcctgta tatattcaaa caaccattta tgagaccagt acaaactact  1080
caagaggaag atggctgtag ctgccgattt ccagaagaag aagaaggagg atgtgaactg  1140
agagtgaagt tcagcaggag cgcagacgcc cccgcgtaca gcagggcca gaaccagctc  1200
tataacgagc tcaatctagg acgaagagag gagtacgacg ttttggacaa gagacgtggc  1260
cgggaccctg agatgggggg aaagccgaga aggaagaacc tcaggaagg cctgtacaat  1320
gaactgcaga agataagat ggcggaggcc tacagtgaga ttgggatgaa aggcgagcgc  1380
cggaggggca aggggcacga tggcctttac cagggtctca gtacagccac caaggacacc  1440
tacgacgccc ttcacatgca ggccctgccc cctcgctaat aa                    1482
```

<210> SEQ ID NO 22
<211> LENGTH: 1515
<212> TYPE: DNA
<213> ORGANISM: Artificial
<220> FEATURE:
<223> OTHER INFORMATION: Chemically synthesized

<400> SEQUENCE: 22

```
atgggatgga gctgtatcat cctcttcttg gtagcaacag ctacaggtgt ccactccgac    60
tacaaagatg atgacgataa ggatatccag ctgacccagt ctccagcttc tttggctgtg   120
tctctagggc agagggccac catctcctgc aaggccagcc aaagtgttga ttatgatggt   180
gatagttatt tgaactggta ccaacagatt ccaggacagc cacccaaact cctcatctat   240
gatgcatcca atcgagtttc tgggatccca cccaggttta gtggcagtgg gtctgggaca   300
gacttcaccc tcaacatcca tcctgtggag aaggtggatg ctgcaaccta tcactgtcag   360
caaagtactg aggatccgtg gacgttcggt ggagggacca agctcgagat caaaggtggt   420
ggtggttctg gcggcggcgg ctccggtggt ggtggttctc aggtgcagct gcagcagtct   480
ggggctgagc tggtgaggcc tgggtcctca gtgaagattt cctgcaaggc ttctggctat   540
```

-continued

```
gcattcagta gctactggat gaactgggtg aagcagaggc ctggacaggg tcttgagtgg      600
attggacaga tttggcctgg agatggtgat actaactaca atggaaagtt caagggtaaa      660
gccactctga ctgcagacga atcctccagc acagcctaca tgcaactcag cagcctagca      720
tctgaggact ctgcggtcta tttctgtgca agacgggaga ctacgacggt aggccgttat      780
tactatgcta tggactactg gggccaaggg accacggtca ccgtctcctc cgcggccgca      840
accacgacgc cagcgccgcg accaccaaca ccggcgccca ccatcgcgtc gcagcccctg      900
tccctgcgcc cagaggcgtg ccggccagcg gcggggggcg cagtgcacac gagggggctg      960
gacttcgcct gtgatatcta catctgggcg cccttggccg ggacttgtgg ggtccttctc     1020
ctgtcactgg ttatcaccct ttactgcaaa cggggcagaa agaaactcct gtatatattc     1080
aaacaaccat ttatgagacc agtacaaact actcaagagg aagatggctg tagctgccga     1140
tttccagaag aagaagaagg aggatgtgaa ctgagagtga agttcagcag gagcgcagac     1200
gccccgcgt acaagcaggg ccagaaccag ctctataacg agctcaatct aggacgaaga     1260
gaggagtacg acgttttgga caagagacgt ggccgggacc ctgagatggg gggaaagccg     1320
agaaggaaga accctcagga aggcctgtac aatgaactgc agaaagataa gatggcggag     1380
gcctacagtg agattgggat gaaaggcgag cgccggaggg gcaaggggca cgatggcctt     1440
taccagggtc tcagtacagc caccaaggac acctacgacg cccttcacat gcaggccctg     1500
ccccctcgct aataa                                                      1515
```